US012213930B2

(12) United States Patent
Sloan

(10) Patent No.: US 12,213,930 B2
(45) Date of Patent: *Feb. 4, 2025

(54) ADAPTIVE SPEECH AND BIOFEEDBACK CONTROL OF SEXUAL STIMULATION DEVICES

(71) Applicant: Brian Sloan, Mercer Island, WA (US)

(72) Inventor: Brian Sloan, Mercer Island, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/365,158

(22) Filed: Aug. 3, 2023

(65) Prior Publication Data

US 2023/0372190 A1 Nov. 23, 2023

Related U.S. Application Data

(63) Continuation of application No. 17/857,983, filed on Jul. 5, 2022, now Pat. No. 11,771,618, which is a continuation-in-part of application No. 17/857,423, filed on Jul. 5, 2022, now abandoned, which is a continuation-in-part of application No. 17/853,316, filed on Jun. 29, 2022, now Pat. No. 11,540,971, and a continuation-in-part of application No. 17/839,426, filed on Jun. 13, 2022, now Pat. No. 11,596,573, which is a continuation-in-part of application No. 17/737,974, filed on May 5, 2022, now Pat. No. 11,607,366, said application No. 17/853,316 is a
(Continued)

(51) Int. Cl.
*A61H 19/00* (2006.01)
*G06F 16/783* (2019.01)
*G06N 20/00* (2019.01)
*H04N 21/234* (2011.01)
*H04N 21/2387* (2011.01)
*H04N 21/242* (2011.01)

(52) U.S. Cl.
CPC ............. *A61H 19/00* (2013.01); *A61H 19/32* (2013.01); *G06F 16/783* (2019.01); *G06N 20/00* (2019.01); *H04N 21/23418* (2013.01); *H04N 21/2387* (2013.01); *H04N 21/242* (2013.01); *A61H 2201/501* (2013.01); *A61H 2201/5058* (2013.01); *A61H 2230/825* (2013.01)

(58) Field of Classification Search
None
See application file for complete search history.

(56) References Cited

U.S. PATENT DOCUMENTS

| 11,077,014 B2 | 8/2021 | Rossi |
| 2014/0288364 A1 | 9/2014 | Bernard |
| (Continued) | | |

*Primary Examiner* — Thaddeus B Cox
(74) *Attorney, Agent, or Firm* — Boon Intellectual Property Law, PLLC; Brian S. Boon

(57) ABSTRACT

A system and method for adaptive speech and biofeedback control of sexual stimulation devices. In an embodiment, the system and method involve receiving audio from a microphone, processing the audio through an automated speech detection engine to detect speech within the audio, matching the speech to a control command for a sexual stimulation device, generating a control signal for the sexual stimulation device based on the control command, receiving biometric data from a biometric sensor, and adjusting the control signals based on the biometric data before outputting the adjusted control signal for use in operating the sexual stimulation device. In some embodiments, the adjustment to the control signal is made automatically by a machine learning algorithm using the command and biometric data as inputs.

20 Claims, 39 Drawing Sheets

Related U.S. Application Data continuation-in-part of application No. 17/737,974, filed on May 5, 2022, now Pat. No. 11,607,366, which is a continuation-in-part of application No. 17/534,155, filed on Nov. 23, 2021, now Pat. No. 11,478,398, which is a continuation of application No. 16/861,014, filed on Apr. 28, 2020, now Pat. No. 11,185,465, which is a continuation-in-part of application No. 16/214,030, filed on Dec. 7, 2018, now Pat. No. 10,638,174, which is a continuation-in-part of application No. 16/139,550, filed on Sep. 24, 2018, now Pat. No. 10,576,013.

(56) References Cited

U.S. PATENT DOCUMENTS

| | | |
|---|---|---|
| 2015/0305971 A1 | 10/2015 | Davis et al. |
| 2016/0030279 A1 | 2/2016 | Driscoll et al. |
| 2016/0199249 A1 | 7/2016 | Dunham et al. |
| 2016/0300569 A1 | 10/2016 | Zhou et al. |
| 2021/0233530 A1 | 7/2021 | Thomson et al. |
| 2022/0218979 A1 | 7/2022 | Eisenberg |
| 2023/0023794 A1 | 1/2023 | Plasencia et al. |

EEG Control Machine Learning Training Algorithm

STAGE 1 - Training on Curated Data 2410

Train machine learning algorithm using pre-labeled data from other users 2411

STAGE 2 - User-Specific EEG Data Capture & Training Using Visual Tasks 2420

Display EEG training task on computer screen 2421 → Receive and record EEG signal data 2422 → Update visual display of EEG training task 2423 → Associate patterns of EEG signal data with task objectives 2424 (repeat)

→ Use associations to generate direct control signals for device 2425

STAGE 3 - User-Specific EEG Data Capture & Training Using Stimulation Tasks 2430

Provide stimulation & ask user to make mental association (image, feeling, etc.) 2431 → Receive and record EEG signal data 2432 → Receive and record biometric signal data and/or user feedback 2433 → Associate patterns of EEG signal data with stimulation, biometric signal data, and/or user feedback 2434 (repeat)

→ Use associations as labeled training data for machine learning algorithms 2440

Fig. 24

Voice Control Machine Learning Training Algorithm

STAGE 1 - Training on Curated Data 3010

Train machine learning algorithm using pre-labeled data from other users 3011

STAGE 2 - User-Specific Voice Data Capture & Training Using Visual Tasks 3020

Display voice training task on computer screen 3021 → Receive and record voice signal data 3022 → Update visual display of voice training task 3023 → Associate patterns of voice signal data with task objectives 3024 repeat

Use associations to generate direct control signals for device 3025

STAGE 3 - User-Specific Voice Data Capture & Training Using Stimulation Tasks 3030

Provide stimulation & ask user to make mental association (image, feeling, etc.) 3031 → Receive and record voice signal data 3032 → Receive and record biometric signal data and/or user feedback 3033 → Associate patterns of voice signal data with stimulation, biometric signal data, and/or user feedback 3034 repeat

Use associations as labeled training data for machine learning algorithms 3040

Fig. 30

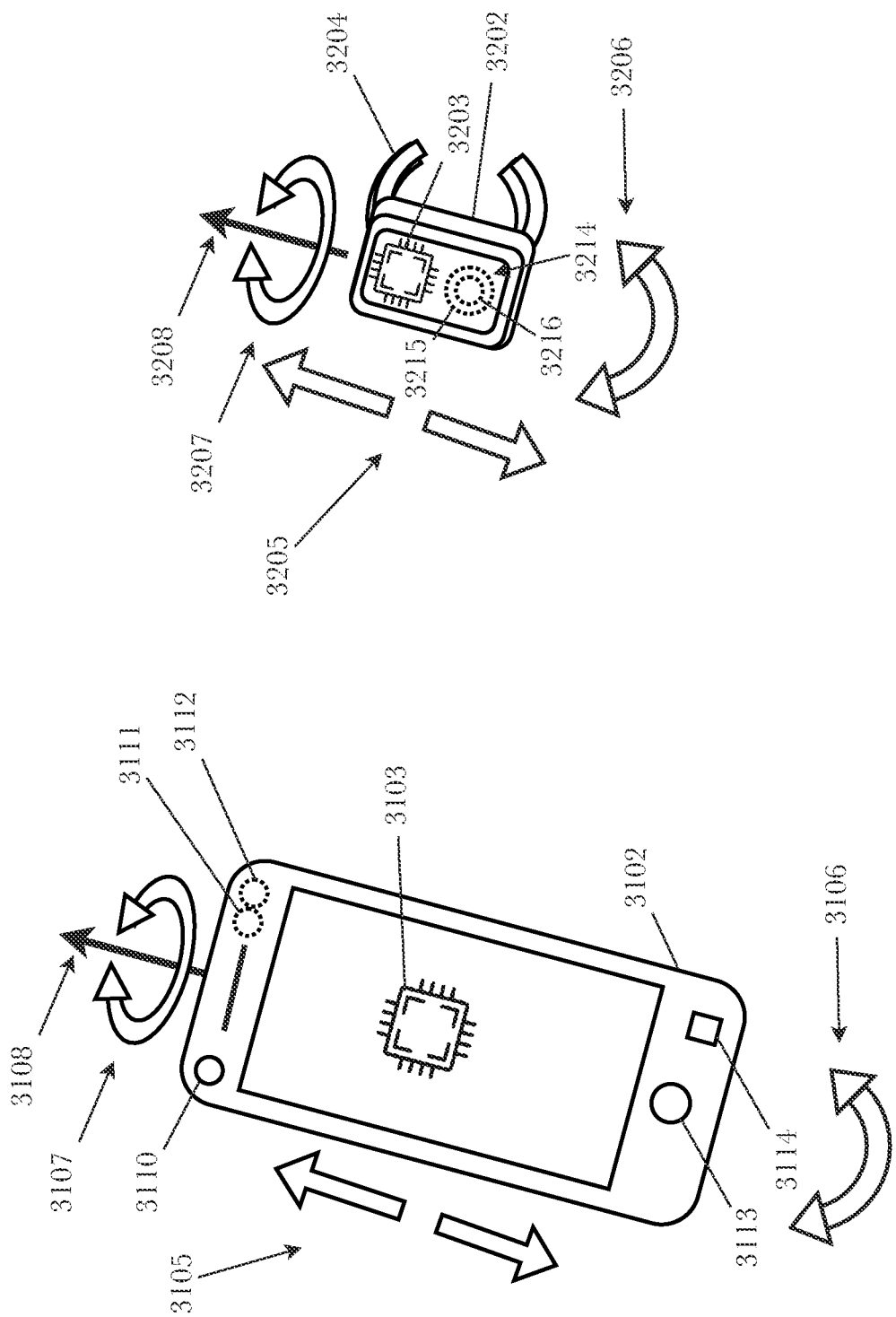

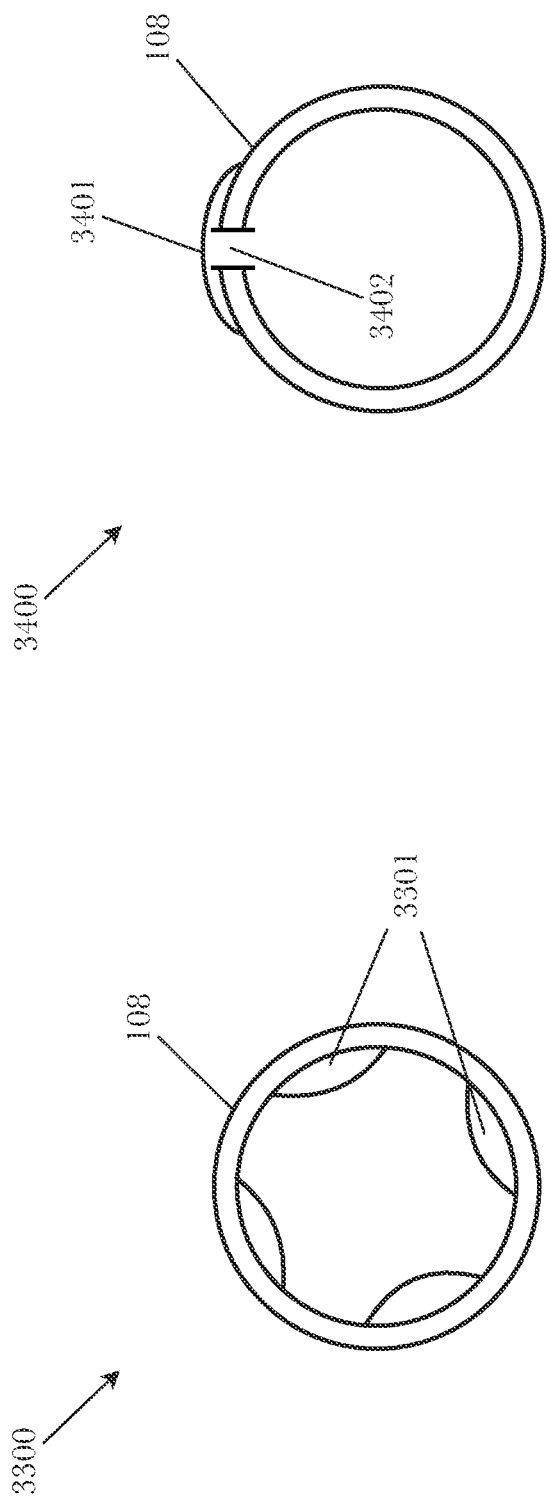

ADAPTIVE SPEECH AND BIOFEEDBACK CONTROL OF SEXUAL STIMULATION DEVICES

CROSS-REFERENCE TO RELATED APPLICATIONS

Priority is claimed in the application data sheet to the following patents or patent applications, each of which is expressly incorporated herein by reference in its entirety:
Ser. No. 17/857,983, now U.S. Pat. No. 11,771,618
Ser. No. 17/857,423, now abandoned
Ser. No. 17/853,316, now U.S. Pat. No. 11,540,971
Ser. No. 17/839,426, now U.S. Pat. No. 11,596,573
Ser. No. 17/737,974, now U.S. Pat. No. 11,607,366
Ser. No. 17/534,155, now U.S. Pat. No. 11,478,398
Ser. No. 16/861,014, now U.S. Pat. No. 11,185,465
Ser. No. 16/214,030, now U.S. Pat. No. 10,638,174
Ser. No. 16/139,550, now U.S. Pat. No. 10,576,013

BACKGROUND OF THE INVENTION

Field of the Art

The present invention is in the field of computer control systems, and more specifically the field of control systems for sexual stimulation devices.

Discussion of the State of the Art

In the field of sexual stimulation devices, control systems are rudimentary, and primarily limited to pre-programmed, selectable stimulation routines. Where customization is possible, it is available only through manual programming of the device. Control systems requiring manipulation of physical or touch-screen controls can be cumbersome or distracting.

What is needed is a system and method for adaptive speech and biofeedback control of sexual stimulation devices.

SUMMARY OF THE INVENTION

Accordingly, the inventor has conceived, and reduced to practice, a system and method for adaptive speech and biofeedback control of sexual stimulation devices. In an embodiment, the system and method involve receiving audio from a microphone, processing the audio through an automated speech detection engine to detect speech within the audio, matching the speech to a control command for a sexual stimulation device, generating a control signal for the sexual stimulation device based on the control command, receiving biometric data from a biometric sensor, and adjusting the control signals based on the biometric data before outputting the adjusted control signal for use in operating the sexual stimulation device. In some embodiments, the adjustment to the control signal is made automatically by a machine learning algorithm using the command and biometric data as inputs.

According to a preferred embodiment, an adaptive speech system for sexual stimulation devices is disclosed, comprising: a computing device comprising a memory and a processor; a microphone connected to the computing device and configured to receive audio and transmit the audio to the computing device; a speech detector comprising a first plurality of programming instructions stored in the memory which, when operating on the processor, causes the computing device to: receive the audio via the microphone; perform automated speech recognition to detect speech in the audio; match the detected speech to one or more commands for a sexual stimulation device; and send the one or more commands to a control signal generator; a voice data manager comprising a second plurality of programming instructions stored in the memory which, when operating on the processor, causes the computing device to determine an association between the speech and a stimulation objective based on a plurality of speech/objective pairs; and a control signal generator comprising a second plurality of programming instructions stored in the memory which, when operating on the processor, causes the computing device to: receive the one or more commands from the speech detector; generate a control signal for the sexual stimulation device corresponding to the one or more commands; receive the association and adjust the control signal based on the association; and output the adjusted control signal for use in operating the sexual stimulation device.

According to a preferred embodiment, a method for adaptive speech of sexual stimulation devices is disclosed, comprising the steps of: using speech detector software operating on a computing device comprising a memory and a processor to: receive audio via a microphone connected to the computing device and configured to receive the audio and transmit the audio to the computing device; perform automated speech recognition to detect speech in the audio; match the detected speech to one or more commands for a sexual stimulation device; and send the one or more commands to a control signal generator application operating on the computing device; using a voice data manager application operating on the computing device to determine an association between the speech and a stimulation objective based on a plurality of speech/objective pairs; and using the control signal generator application operating on the computing device to: receive the one or more commands from the speech detector software; generate a control signal for the sexual stimulation device corresponding to the one or more commands; receive the association and adjust the control signal based on the association; and output the adjusted control signal for use in operating the sexual stimulation device.

According to an aspect of an embodiment, the computing device is incorporated into the sexual stimulation device.

According to an aspect of an embodiment, the microphone is incorporated into the sexual stimulation device.

According to an aspect of an embodiment, wherein: a biometric sensor connected to the computing device and configured to receive biometric data and transmit the biometric data to the computing device; and the voice data manager is further configured to receive the biometric data from the biometric sensor and further adjust the control signal based on the biometric data prior to outputting the adjusted control signal for use in operating the sexual stimulation device.

According to an aspect of an embodiment, the biometric sensor is an external heart rate monitoring device connected to the computing device.

According to an aspect of an embodiment, the computing device is a mobile phone connected wirelessly to the sexual stimulation device.

According to an aspect of an embodiment, the microphone is incorporated into the mobile phone.

According to an aspect of an embodiment, the computing device is a mobile phone connected wirelessly to the sexual stimulation device and wherein the biometric sensor is incorporated into the mobile phone.

According to an aspect of an embodiment, the computing device is a mobile phone connected wirelessly to the sexual stimulation device and wherein the biometric sensor is an external heart rate monitoring device connected to the mobile phone.

According to an aspect of an embodiment, a machine learning algorithm is configured to automatically determine the adjustment to the control signal using the one or more commands and the biometric data as inputs.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

FIG. 24 is an exemplary algorithm for electroencephalograph data capture and machine learning algorithm training for thought-based control of sexual stimulation devices.

FIG. 30 is an exemplary algorithm for voice data capture and machine learning algorithm training for voice-based control of sexual stimulation devices.

FIG. 31 shows an exemplary use of a mobile computing device as a biofeedback-based controller for sexual stimulation devices.

FIG. 32 shows an exemplary use of a smartwatch or fitness tracker as a biofeedback-based controller for sexual stimulation devices.

FIG. 33 and FIG. 34 show exemplary integrations of a penile tumescence sensor into a gripper for use as a biometric feedback device.

DETAILED DESCRIPTION OF THE INVENTION

Figure 1:
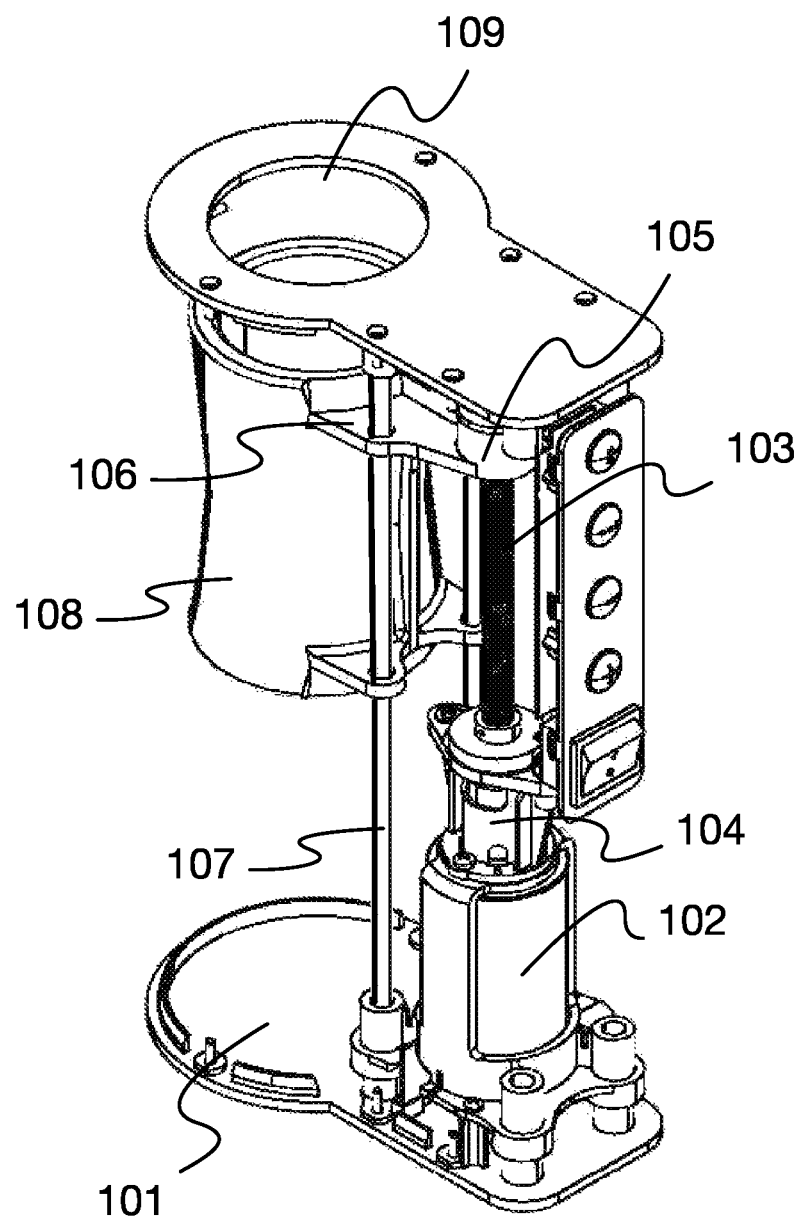
FIG. 1 shows the internal workings of an exemplary sexual stimulation device.

The inventor has conceived, and reduced to practice, a system and method for adaptive speech and biofeedback control of sexual stimulation devices. In an embodiment, the system and method involve receiving audio from a microphone, processing the audio through an automated speech detection engine to detect speech within the audio, matching the speech to a control command for a sexual stimulation device, generating a control signal for the sexual stimulation device based on the control command, receiving biometric data from a biometric sensor, and adjusting the control signals based on the biometric data before outputting the adjusted control signal for use in operating the sexual stimulation device. In some embodiments, the adjustment to the control signal is made automatically by a machine learning algorithm using the command and biometric data as inputs.

This automated generation of control signals from voice commands combined with biometric data acts as a sort of "autopilot" for sexual stimulation devices such that a priori programming or manual programming of the devices either not required at all or is minimal in nature. The device can simply be turned on and stimulation will be automatically customized to the user's preferences with little or no input on the user's part based on biometric data from a biometric sensors or may be used in conjunction with voice commands which are adjusted based on the biometric data. For example, a wearable device such as a smartwatch or fitness tracker may be used to provide heart rate data to a sexual stimulation device and the sexual stimulation device will adjust the intensity of stimulation based on the user's heart rate data (which can be used as a proxy for sexual arousal in this context). The wearable device is wirelessly paired (e.g., via Bluetooth, WiFi, etc.) with the sexual stimulation device. The wearable device has a biometric sensor such as an optical heart rate sensor, capable of detecting the user's heart rate. The user may set an initial intensity of stimulation using an voice control (or a default initial stimulation intensity is selected) and the intensity of stimulation is automatically adjusted by the sexual stimulation device based on the heart rate data from the wearable device. In some embodiments, instead of having a connection between the sexual stimulation device and the biometric sensor, a mobile computing device may be paired with both the sexual stimulation device and the biometric sensor, and may act as the intermediary between the two. In some embodiments, the biometric sensor may be a sensor integrated into the mobile computing device. In some embodiments, the biometric sensor may be a sensor integrated into the sexual stimulation device.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

FIG. 1 shows the internal workings of an exemplary sexual stimulation device 100. The compatible device is a small handheld unit powered by a low voltage, external direct current (DC) power source. Inside the device is a metal framework 101 to which the mechanical parts of the device are attached. Attached to the metal framework 101 is a small DC motor 102 with a motor shaft 103, which drives the stimulation mechanism. A screw shaft 104 is affixed to the motor shaft 103 of the DC motor 102, such that the screw shaft 104 rotates as the motor shaft 103 of the DC motor 102 rotates. The polarity of voltage to the DC motor 102 may be reversed so that the motor shaft 103 of the DC motor 102 rotates both clockwise and counter-clockwise. A flex coupling 105 between the motor shaft 103 of the DC motor 102 and screw shaft 104 compensates for any misalignment between the two during operation. A screw collar 106 is placed around the screw shaft 104 and attached to a bracket 107, which is held in a particular orientation by guide rods 108, such that the screw collar 106 and bracket 107 travel in a linear motion as the screw shaft 104 is turned. Affixed to the bracket 107 is a gripper 109, which travels in a linear motion along with the bracket 107. A hole 110 in the metal framework 101, allows for the insertion of a flexible sleeve as shown in FIG. 2.

Figure 2:
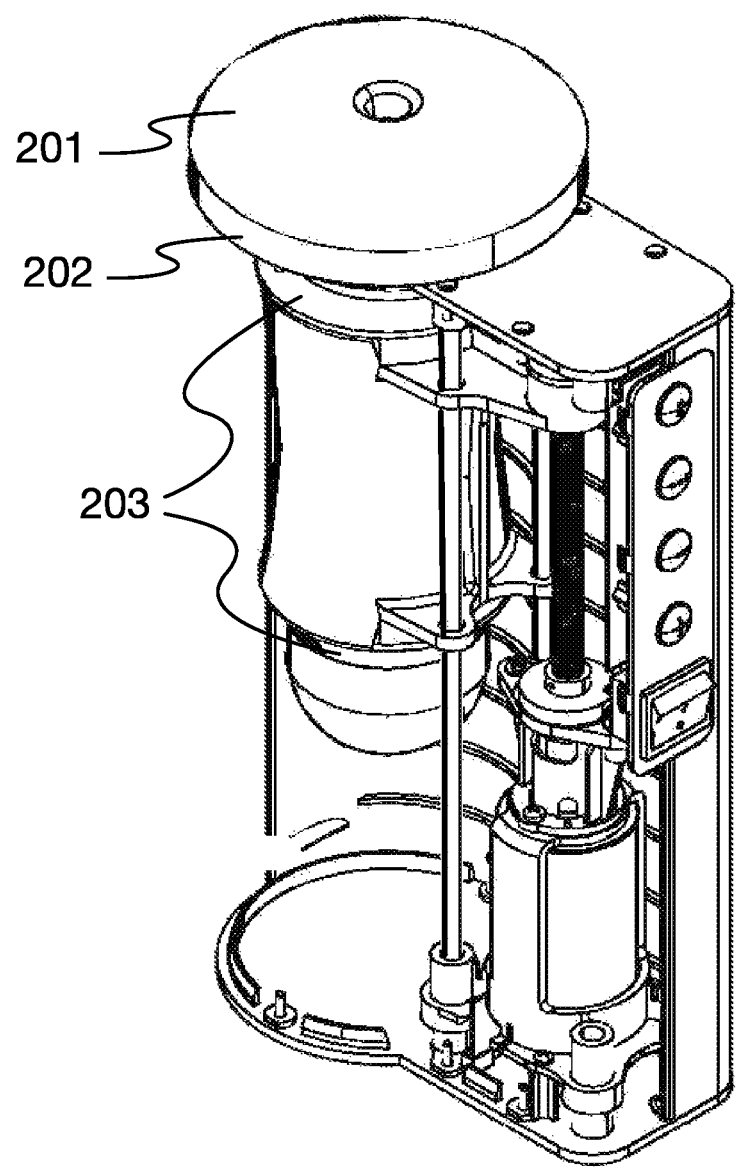
FIG. 2 shows additional components of the internal workings of an exemplary sexual stimulation device.

FIG. 2 shows additional components of the internal workings of an exemplary sexual stimulation device 200. A flexible sleeve 201 made of either thermoplastic elastomer (TPE) or thermoplastic rubber (TPR) is inserted through a large hole 109 in the metal framework 101 and through gripper 108. Sleeve 201 is prevented from accidentally slipping into device 200 by a ridge 202 at the open end of sleeve 201, and is held in the proper position by ridges 203 at both ends of gripper 108. During operation, gripper 108 slides in a reciprocal linear motion 201 providing pressure and motion against the penis inside the sleeve 201 in a manner similar to sexual intercourse or manual masturbation. Depending on the configuration, gripper 108 may either grip sleeve 201 and move sleeve 201 along the penis, or it may slide along the outside of sleeve 201, not moving the sleeve relative to the penis. Also depending on configuration, gripper 108 may be made of rigid, semi-rigid, or compliant materials, and other shapes might be used (e.g., partial tube, ring, half-ring, multiple rings, loops of wire) and may contain rollers or bearings to increase stimulation and reduce friction against the flexible sleeve 201.

Figure 3:
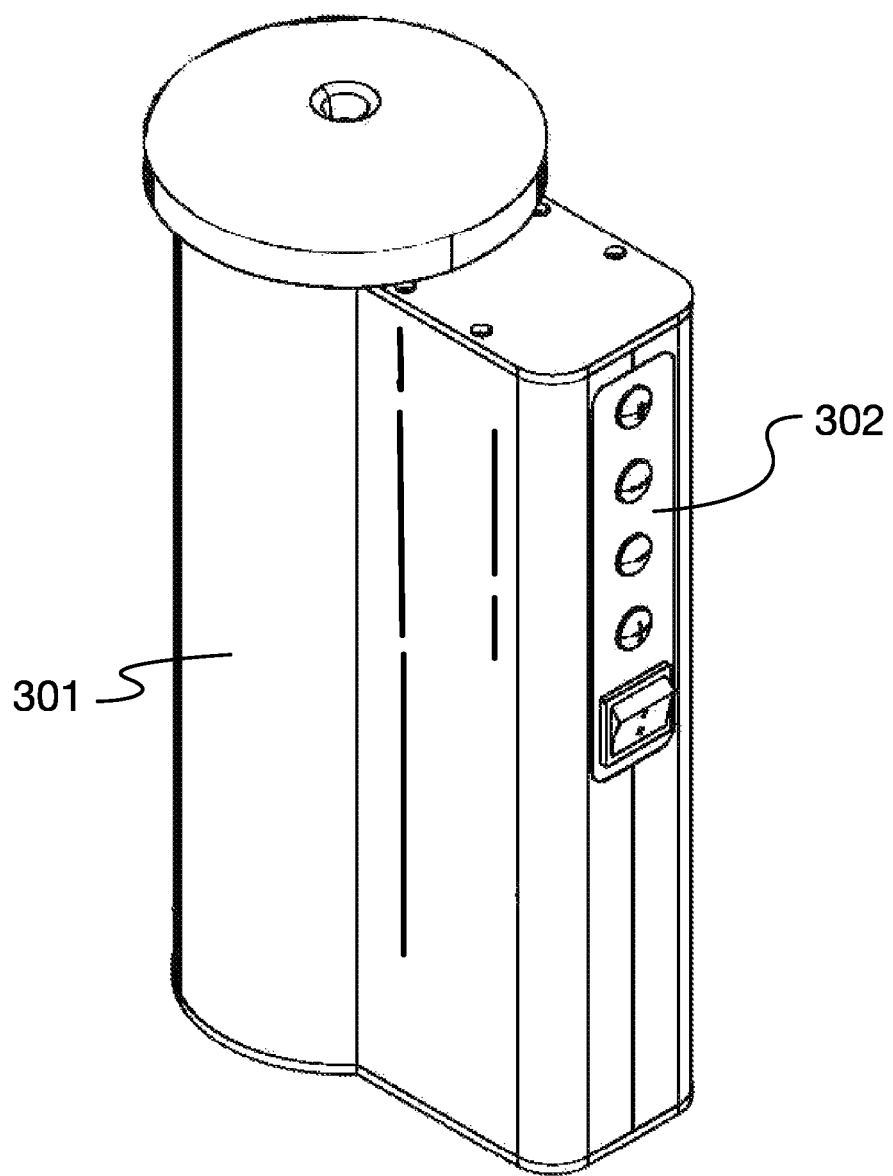
FIG. 3 shows the external structure of an exemplary sexual stimulation device.

FIG. 3 shows the external structure 300 of an exemplary sexual stimulation device. The housing 301 of the device is made of plastic, and is attached to the metal framework in such a way as to provide additional support and structure to the device. User controls 302 in the form of buttons and switches and their associated electronics are built into the housing. The housing has an opening at one end corresponding to the opening 109 in the metal framework 101, into which the flexible sleeve 201 is inserted. The penis is inserted into the sleeve 201 at the end of the device, and is stimulated by the reciprocal linear motion of the gripper 108 inside the device. The user controls the speed, pattern, and location of stimulation using the controls 302 on the outside of the housing 301.

Figure 4:
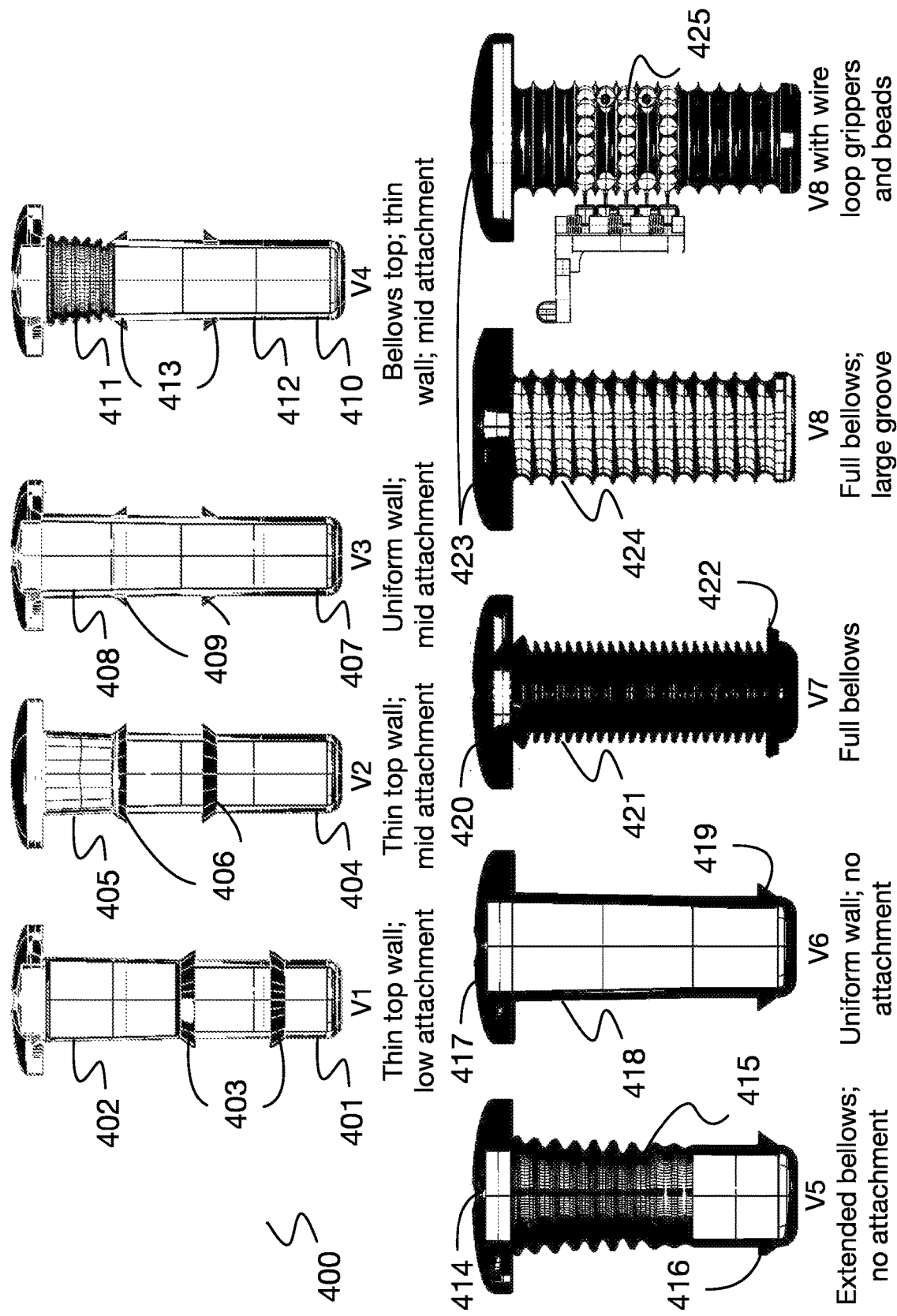
FIG. 4 shows exemplary variations of the sleeve and gripper aspects of an exemplary sexual stimulation device.

FIG. 4 shows exemplary variations 400 of the sleeve 201 and gripper 108 aspects of an exemplary sexual stimulation device. As noted above, different configurations of the sleeve 201 and gripper 108 are possible to allow optimal fit and sensation for penises of different lengths and girths, and to allow the user a choice of pressure, gripper location, and sensation. Sleeve variant one 401 has a thin top wall 402 with a low point of attachment 403 to the gripper 108. Sleeve variant two 404 has a thin top wall 405 with a middle point of attachment 406 to the gripper 108. Sleeve variant three 407 has a uniform wall thickness 408 with a middle point of attachment 409 to the gripper 108. Sleeve variant four 410 has a bellows top 411, a thin wall 412, and a middle point of attachment 413. Sleeve variant five 414 has an extended bellows 415 and no attachment to the gripper 108 other than a stopper at the end 416, allowing the gripper 108 to slide along the outside of the sleeve 414. Sleeve variant six 417 has a uniform wall thickness 418 and no attachment to the gripper 108 other than a stopper at the end 419, allowing the gripper 108 to slide along the outside of the sleeve 417. Sleeve variant seven 420 has a full bellows design 421 and no attachment to the gripper 108 other than a stopper at the end 422, allowing the gripper 108 to slide along the outside of the sleeve 420. Sleeve variant eight 423 has a full bellows design with large grooves 424 into which fits a gripper made of wire loops with beads attached 425.

Figure 5:
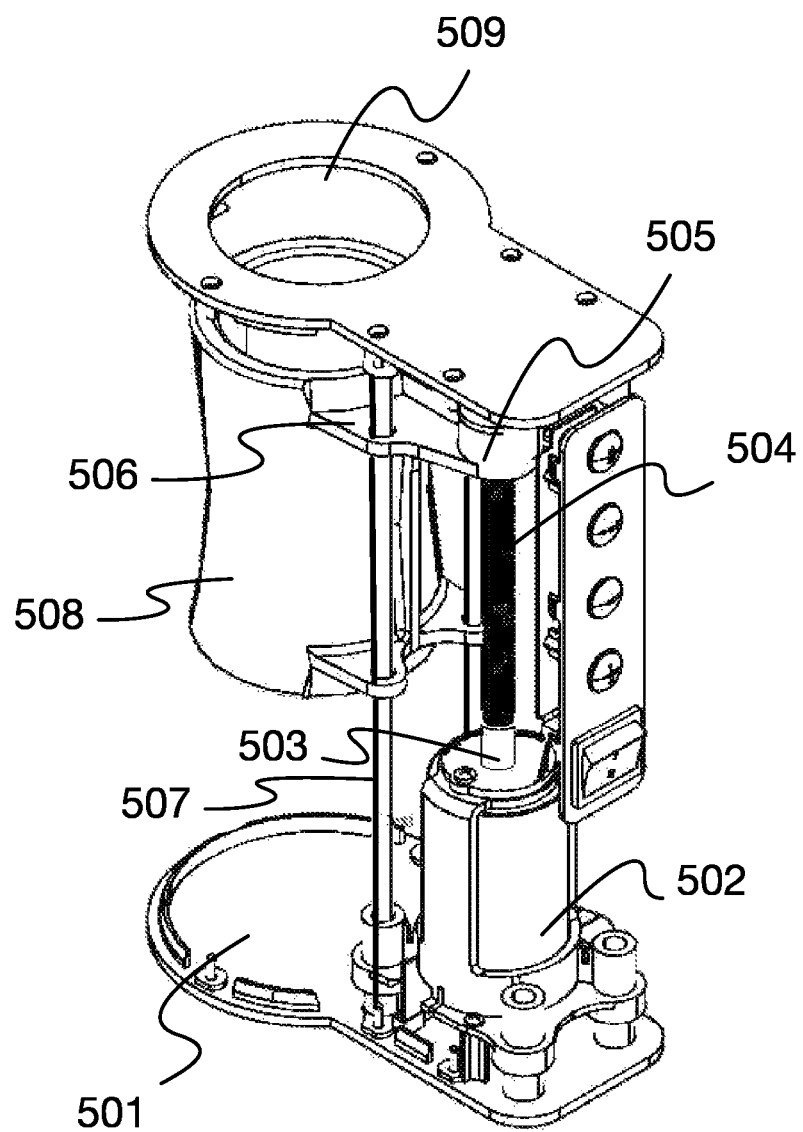
FIG. 5 shows the internal workings of an exemplary sexual stimulation device.
Figure 6:
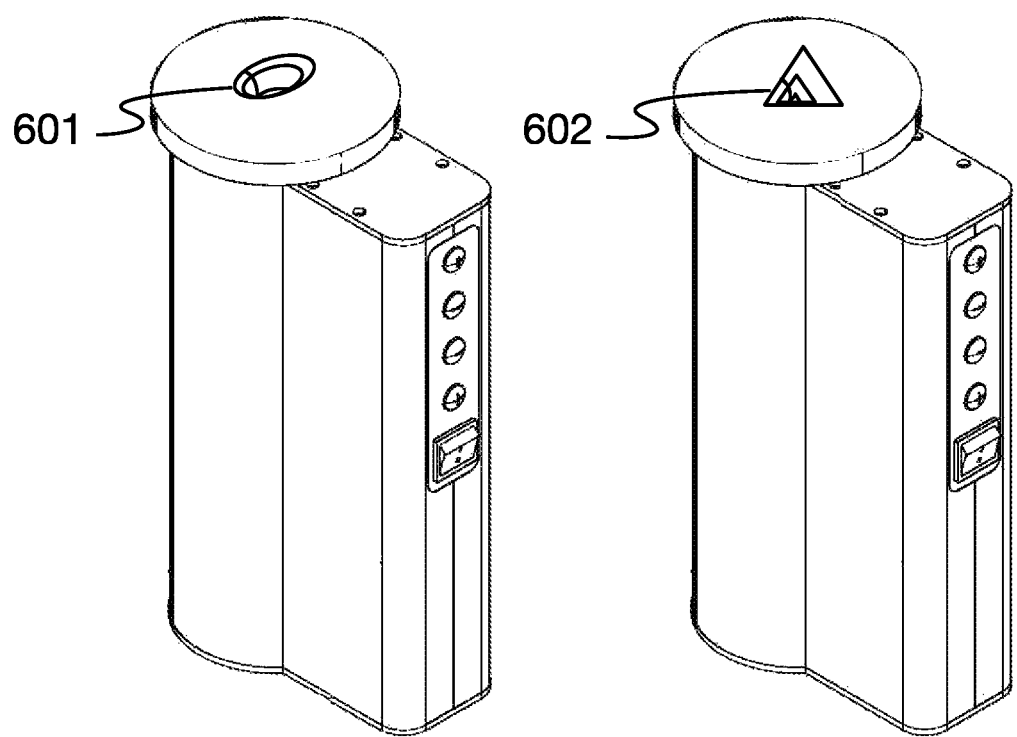
FIG. 6 shows additional exemplary aspects of an exemplary sexual stimulation device.

FIG. 5 shows the internal workings of an exemplary sexual stimulation device 500. The compatible device is a small handheld unit powered by a low voltage, external direct current (DC) power source. Inside the device is a metal framework 501 to which the mechanical parts of the device are attached. Attached to the metal framework 501 is a small DC motor 502 with a motor shaft 503, which drives the stimulation mechanism. A screw shaft 504 is affixed directly to the motor shaft 503 of the DC motor 502, such that the screw shaft 504 rotates as the motor shaft 503 of the DC motor 502 rotates. The polarity of voltage to the DC motor 502 may be reversed so that the motor shaft 503 of the DC motor 502 rotates both clockwise and counter-clockwise. In this embodiment, the flex coupling 105 has been eliminated, allowing the device to be constructed in a more compact form, approximately 2 cm shorter in overall length. A screw collar 505 is placed around the screw shaft 504 and attached to a bracket 506, which is held in a particular orientation by guide rods 507, such that the screw collar 505 and bracket 506 travel in a linear motion as the screw shaft 504 is turned. Affixed to the bracket 506 is a gripper 508, which travels in a linear motion along with the bracket 506. A hole 509 in the metal framework 501, allows for the insertion of a flexible sleeve 201 as previously shown in FIG. 2. FIG. 6 shows additional exemplary variations 600 of the sleeve aspect of an exemplary sexual stimulation device as set forth in another preferred embodiment. In this embodiment, the opening in the sleeve may be other than circular. For example, the opening may be elliptical in shape 601 or triangular in shape 602.

FIG. 6 shows additional exemplary variations of the aspects of an exemplary sexual stimulation device.

Figure 7:
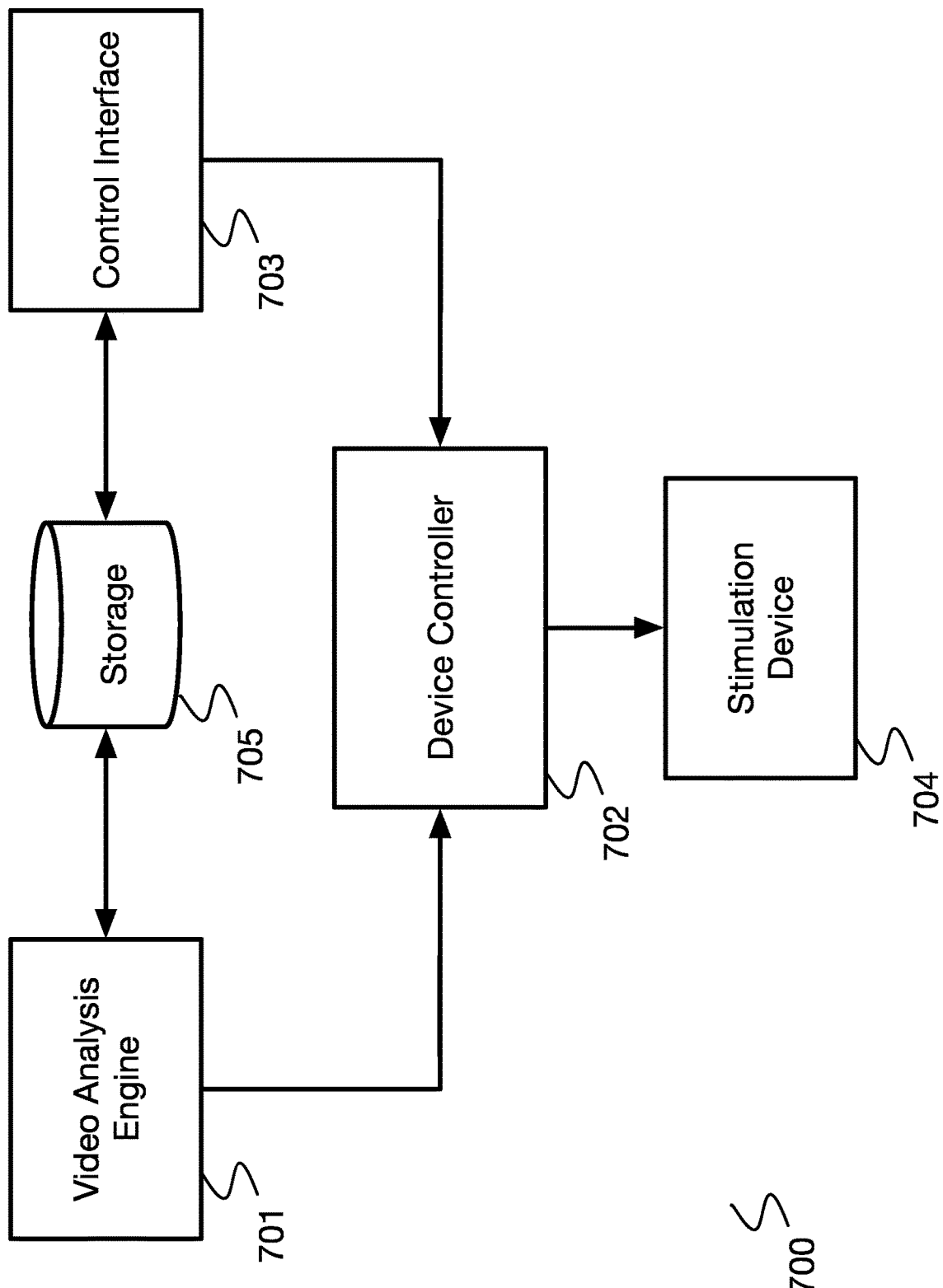
FIG. 7 is a block diagram of an exemplary synchronized video control system for sexual stimulation devices.

FIG. 7 is a block diagram of an exemplary synchronized video control system for sexual stimulation devices 700. In a this embodiment, a video analysis engine 701 inputs a video of sexual activity, parses the video into at least the components of movement corresponding to the sexual activity shown in the video, and outputs signals containing the parsed video information to a device controller 702. A control interface 703 allows the user to enter a profile containing parameters for sexual stimulation device operation or the user's biometric information, stores the user's profile information, and outputs the user's profile information to the device controller 702. The device controller 702 adjusts the signals from the video analysis engine 701 based on the profile information from the control interface 703 and outputs the adjusted signals to a stimulation device 704 such that they are synchronized with the activity shown in the video. In an aspect of an embodiment, the parsed video information from the video analysis engine 701 is stored in a data storage device 705 for later retrieval and use.

Figure 8:
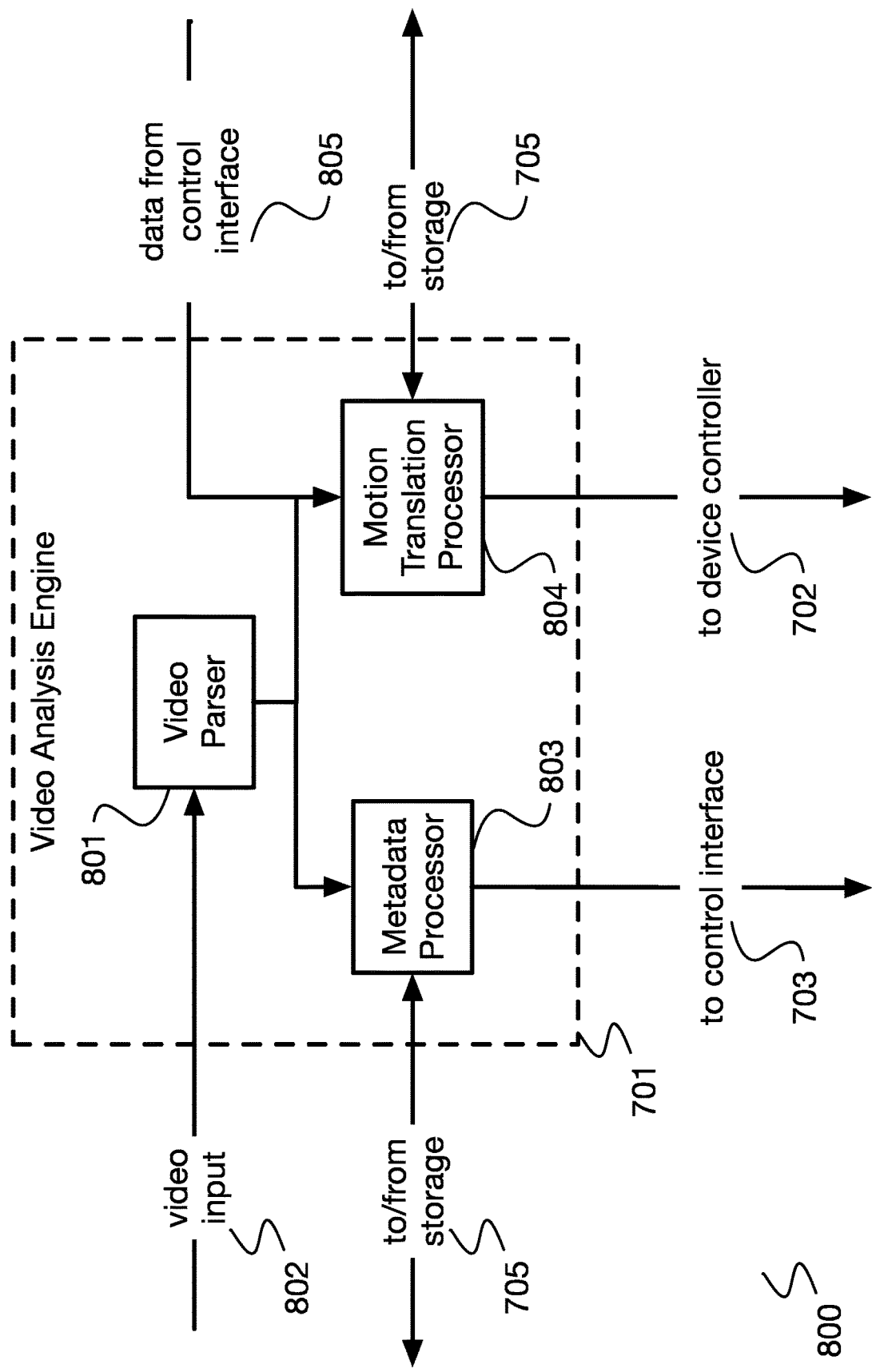
FIG. 8 is a block diagram of the video analysis engine aspect of an exemplary synchronized video control system for sexual stimulation devices.

FIG. 8 is a block diagram 800 the video analysis engine 701 aspect of an exemplary synchronized video control system for sexual stimulation devices. A video parser 801 receives video input 802, sends the video's metadata to a metadata processor 803, which checks to see if the metadata for that video already exists in the data storage device 705. If the metadata already exists, it is read from the data storage device 705 and sent out the control interface 703. If the metadata does not exist, it is formatted, written to the data storage device 705, and sent out to the control interface 703. Simultaneously, the video parser 801 sends the video content to the motion translation processor 804, which checks to see if the control signal data for that video already exists in the data storage device 705. If the control signal data already exists, it is read from the data storage device 705 and sent out the device controller 702. If the control signals do not exist, the motion translation processor 804 uses video processing algorithms and machine learning algorithms to detect sexual activity and to translate the motions in the video to control signals related to movement, pressure, and rhythm, and makes adjustments to the control signals in response to data from the control interface 805. The controls signals are then written to the data storage device 705 and sent out to the device controller 702. In an aspect of an embodiment, the actual video content may also be stored in the data storage device 705.

Figure 9:
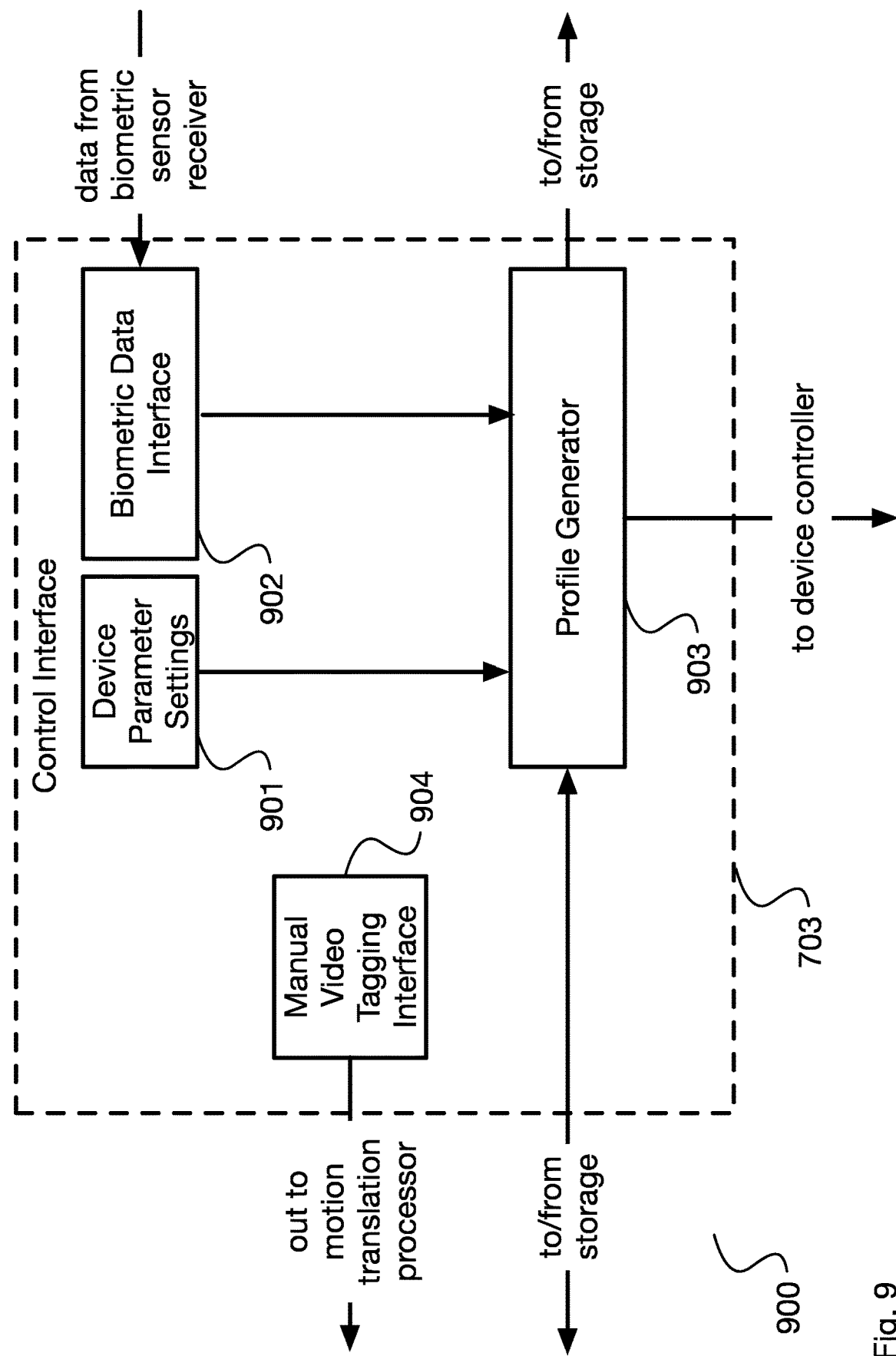
FIG. 9 is a block diagram of the control interface aspect of an exemplary synchronized video control system for sexual stimulation devices.

FIG. 9 is a block diagram 900 of the control interface 703 aspect of an exemplary synchronized video control system for sexual stimulation devices. The user can enter device parameter settings 901 to adjust operation of a compatible device. The user can further enter biometric data manually, or it may be obtained automatically by the biometric data interface 902 from biometric sensor receiver 1004 disclosed in FIG. 10. The parameters and biometric data are sent to a profile generator 903, which creates a profile for the user based on the various inputs. The profile information is saved to the storage device 705, and is sent to the device controller 702. The control interface may contain a manual video tagging interface 904, which allows the user to adjust the sensations received while viewing those videos.

Figure 10:
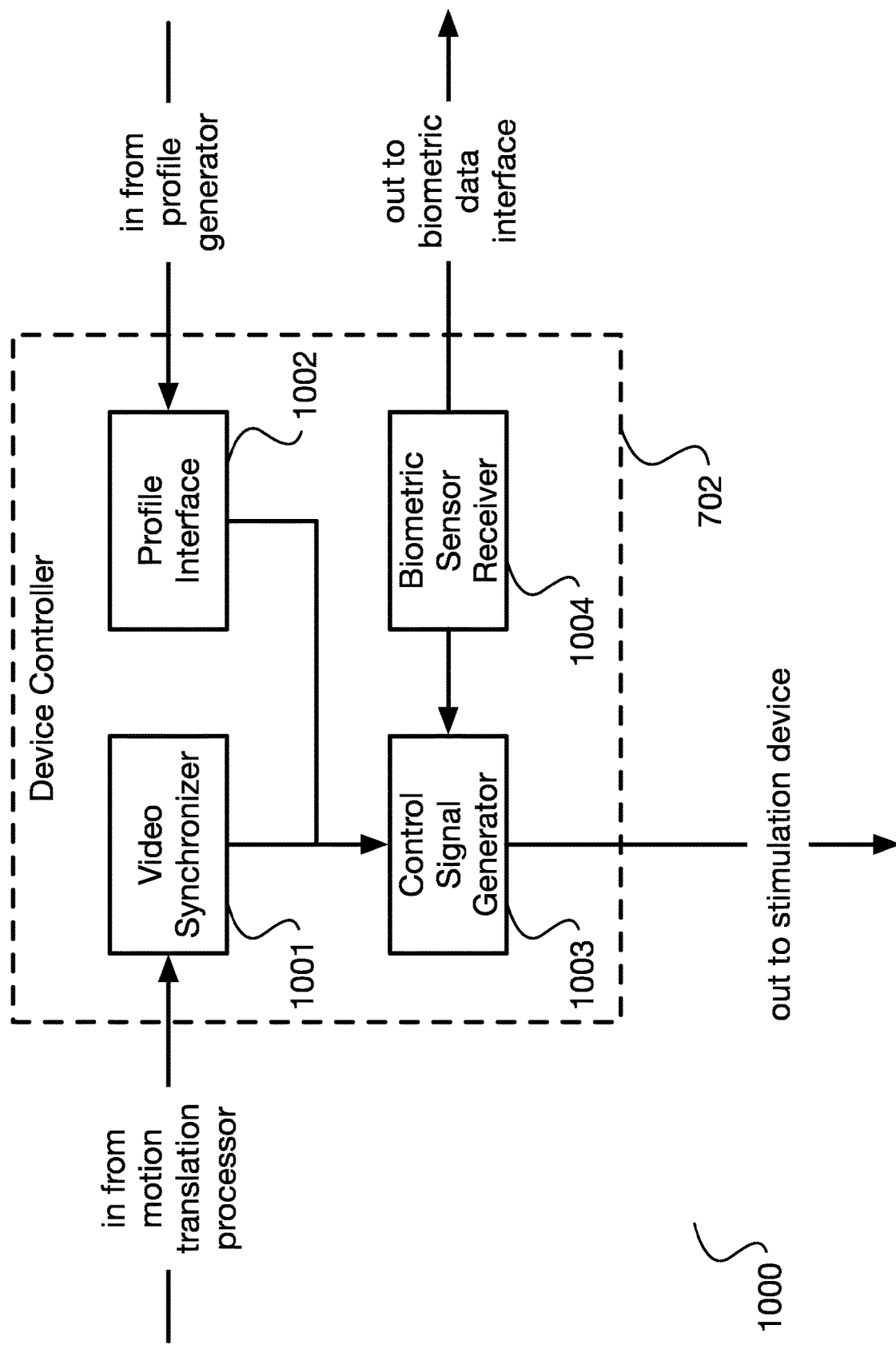
FIG. 10 is a block diagram of the device controller aspect of an exemplary synchronized video control system for sexual stimulation devices.

FIG. 10 is a block diagram 1000 of the device controller 702 aspect of an exemplary synchronized video control system for sexual stimulation devices. Control signals for the video being watched are received from the motion translation processor 804 into the video synchronizer 1001, which adjusts the timing of the signals to correspond with the video being watched. Parameters and biometric data are received into the profile interface 1002 from the profile generator 903. A control signal generator 1003 receives the outputs from both the video synchronizer 1001 and profile interface 1002, and adjusts the synchronized control signals based on the parameters and biometric data, and sends out the adjusted control signal to the stimulation device 704. The device controller may also contain a biometric sensor receiver 1004 that could allow the capture of biometric data from wireless devices such as fitness trackers that monitor heart rate, blood pressure and breathing monitors, and even sensors in the stimulation device itself. The data captured through the biometric sensor receiver could be used for real time feedback to the control signal generator 1003 and for use in improving user experiences by enhancing the user's profile or improving the accuracy of video selection.

Figure 11:
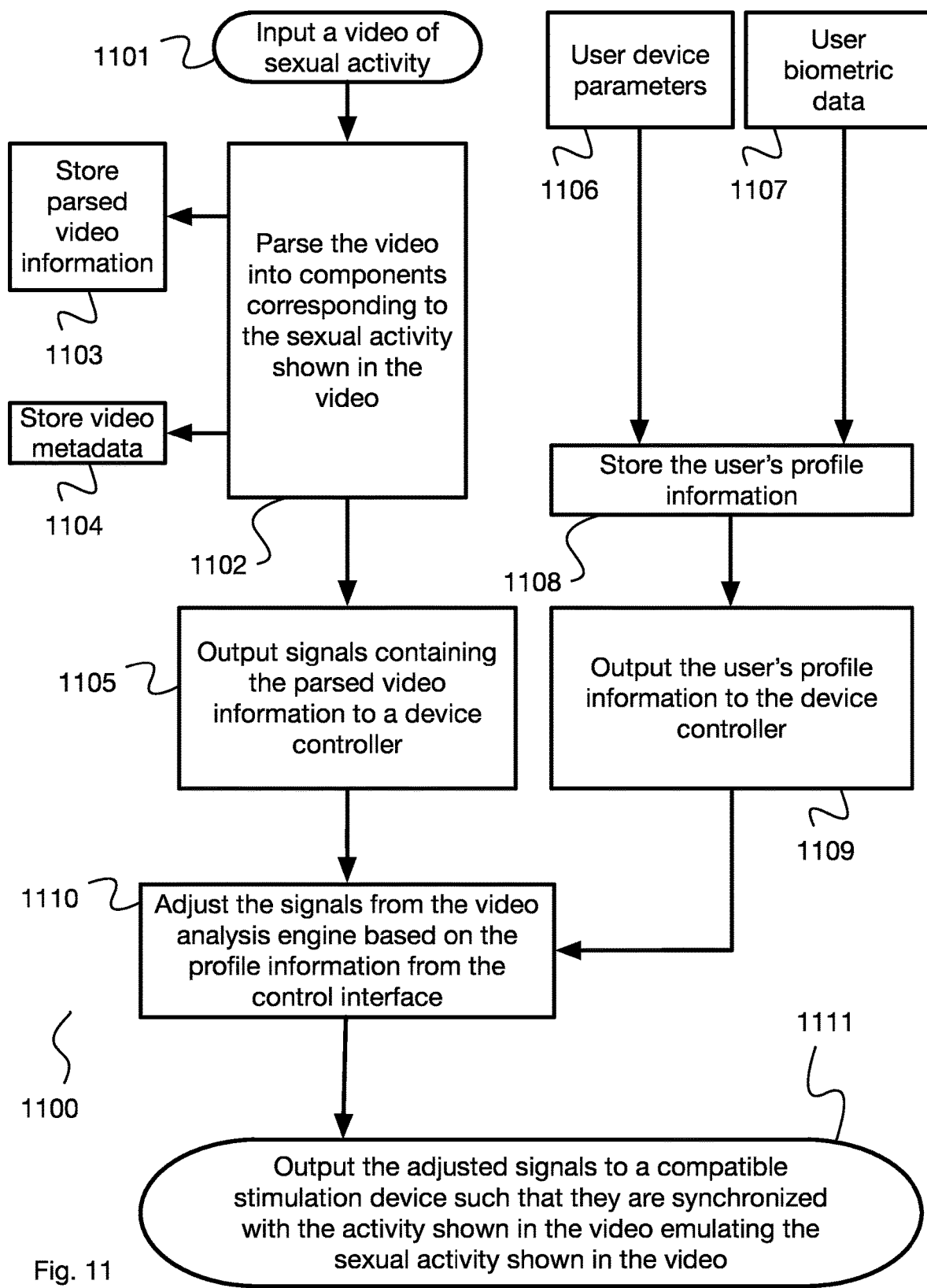
FIG. 11 is a flow diagram showing a method for an exemplary synchronized video control system for sexual stimulation devices.

FIG. 11 is a flow diagram showing a method 1100 for an exemplary synchronized video control system for sexual stimulation devices. According to this method, video of sexual activity would be input into a computer 1101. The computer, using machine learning algorithms, would parse the video into at least one component corresponding to the sexual activity shown in the video 1102. The parsed video information could be stored for later retrieval 1103 and any video metadata could also be stored for later retrieval 1104. Signals containing the parsed video information to a device controller would be output to a device controller 1105. Separately, the user would be allowed to enter a profile in a control interface containing at least parameters for adjusting compatible device operation 1106, and biometric data 1107, which would be stored 1108, and output to the device controller 1109. The signals from the parsed video would be adjusted based on the user's profile information 1110 and output to a compatible device, synchronized with the activity shown in the video, such that the compatible device would emulate the sexual activity shown in the video 1111.

Figure 12:
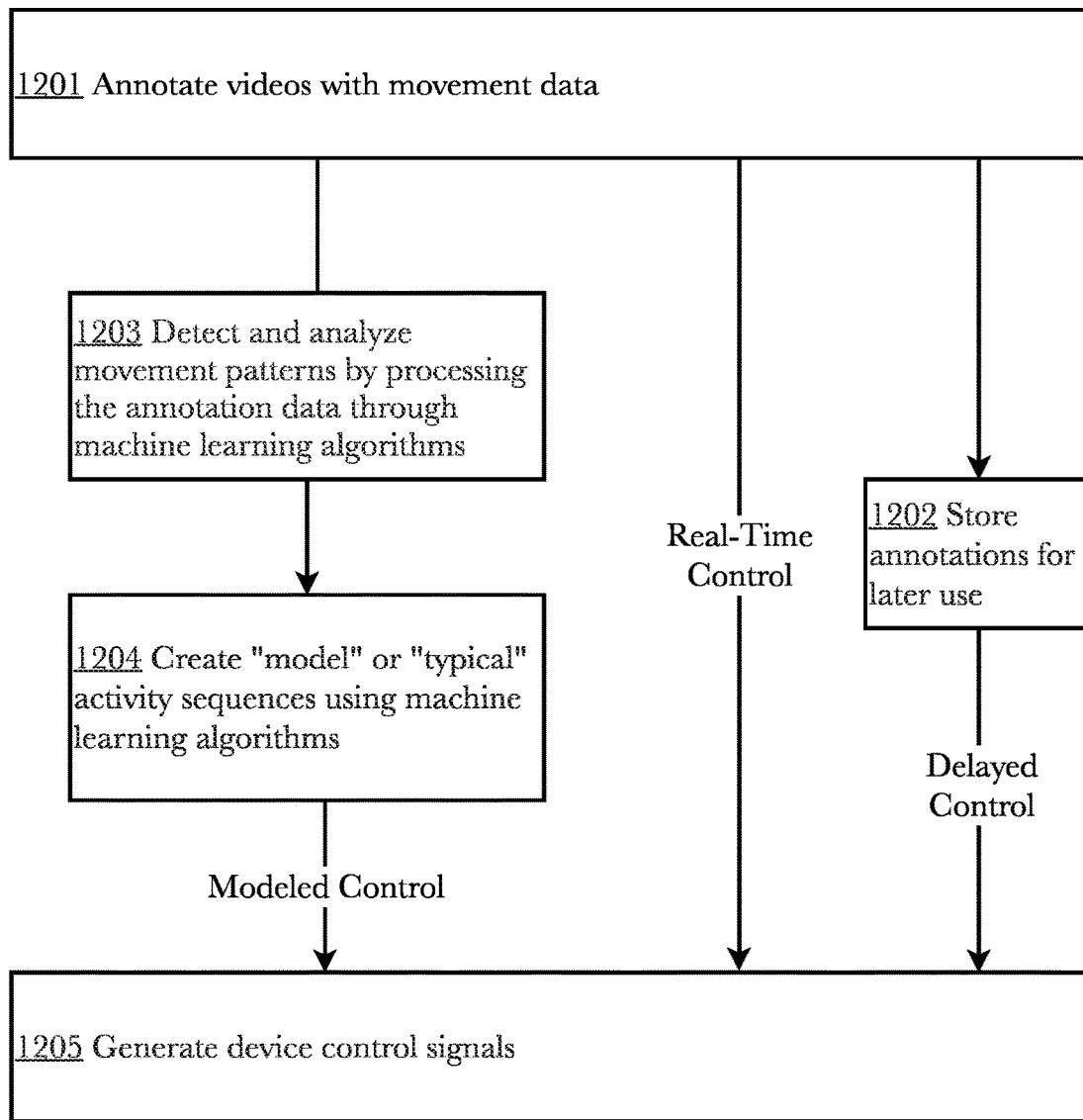
FIG. 12 is a flow diagram showing a method for using annotated video data to control a sexual stimulation device.

FIG. 12 is a flow diagram showing a method for using annotated video data to control a sexual stimulation device. In a first step, videos containing depictions of sexual activity are annotated (or tagged) with data regarding one or more movements shown in the videos 1201. The annotations are associated with playback times in the video, either as metadata incorporated into the video file or as separate files. The annotations (or tags) may be performed manually by a person watching the video or automatically by the video analysis engine 701.

The annotations may be used directly to generate device control signals 1205, such as real-time use wherein the device control signals are generated 1205 immediately or very soon after the annotations are created, or delayed use by storing the annotations for later use 1202 and generating device control signals 1205 from the stored annotations. In this use, the annotations will typically be used to generate control signals for a particular video for which the annotations were made. A single such annotation may be used or some combination of annotations for the same video (e.g., averaging of multiple annotations).

Alternatively, the annotations may be processed through machine learning algorithms to create models of movement patterns and sequences commonly associated with certain videos, or certain sexual activities, persons, etc. In this use, annotations from a plurality of different videos will typically be used. The annotations are processed through a first set of machine learning algorithms to detect and analyze movement patterns typical of certain sexual activities 1203. This first set of machine learning algorithms may use techniques such as clustering to group together similar types of movement patterns. The movement pattern data are then processed through a second set of machine learning algorithms to determine sequencing information 1204 such as how long a pattern is typically held and the probabilities of changing to different patterns after the current pattern. The sequencing information is used to create predictive models of typical or expected sequences of movement patterns, which mimic frequently-seen depictions of sexual activity in the annotated data. The data from these models may then be used to generate device control signals 1205 representing movement patterns and sequences in common sexual activities.

Figure 13:
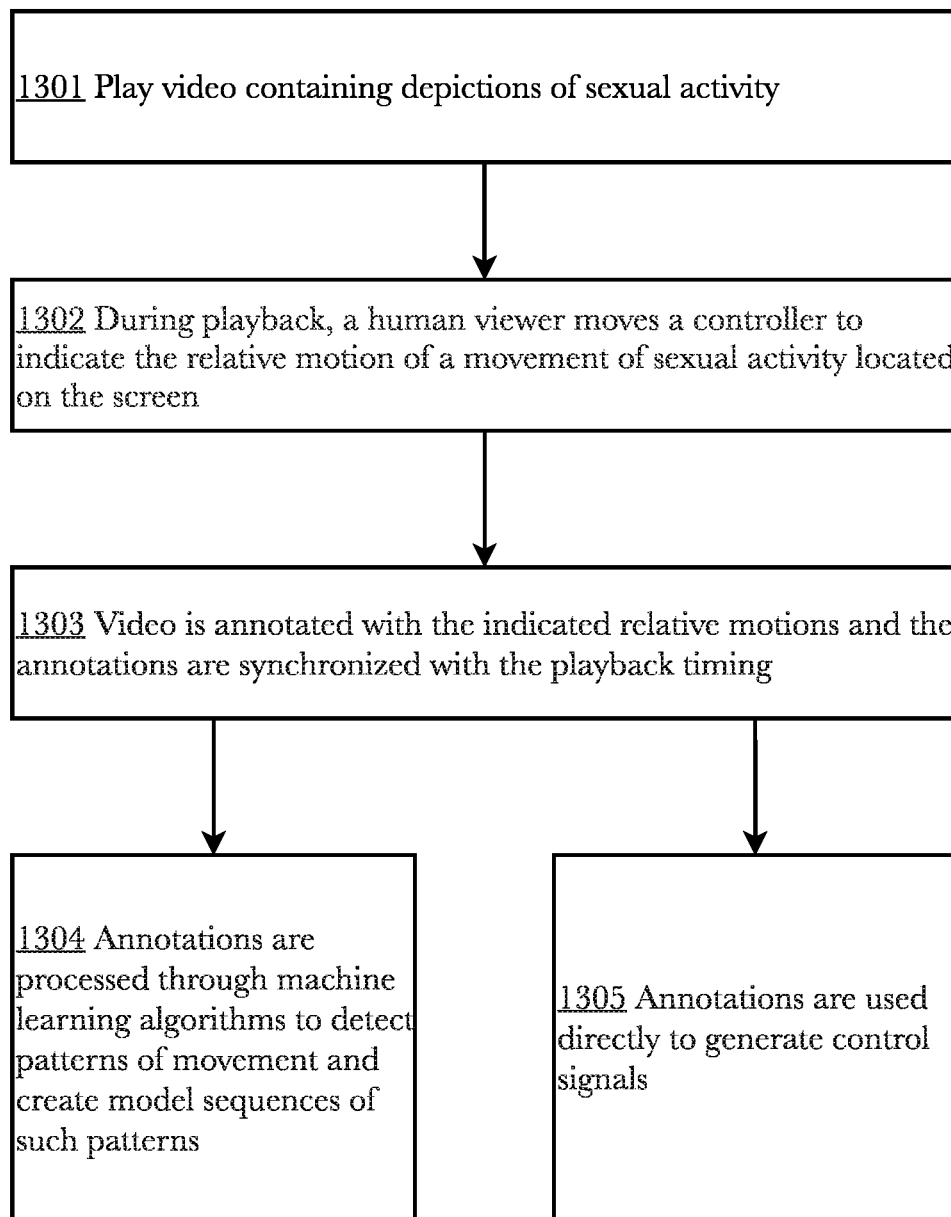
FIG. 13 is a flow diagram showing a method for manual annotation of videos containing depictions of sexual activity.

FIG. 13 is a flow diagram showing a method for manual annotation of videos containing depictions of sexual activity. In a first step, a video is played which contains depictions of sexual activity 1301. During playback, a human viewer moves a controller to indicate the relative motion of a movement of sexual activity located on the screen. The controller may be any device that allows the viewer to input a motion associated with a movement of sexual activity in the video being viewed by the viewer 1302. Ideally, the controller will allow the viewer to simply imitate the motion by mimicking the motion(s) seen in the video (e.g., moving the viewer's hand back and forth) rather than programming in the motion(s) (e.g., by entering a number associated with the motion). The controller may be virtual (e.g., an on-screen slider bar, an on-screen virtual joystick, gestures made in front of a gesture-recognition camera), or the controller may be a physical device (e.g., a physical slider, joystick, wand, mobile phone with an accelerometer, etc.). The controller may allow for linear motions, two-dimensional motions, or three-dimensional motions, and may also allow for rotation or tilting. As the human viewer moves the controller in synchronicity with the movements depicted in the video, annotation data are created that are associated with video playback times 1303. As a simple example, a reciprocal motion depicted in the video may be annotated as tuples, with a series of time stamps representing the video playback time, each associated with a value indicating the relative location of the linear motion in the video at that time. The annotations may be incorporated into the video file as metadata or stored as separate data files. Where the annotations will be used to generate device control data for a particular video, the annotation will typically be associated with the video in some manner. However, where the annotations are to be used as input to machine learning algorithms for generation of models of sexual activity, the annotations may be disassociated with the video from which they are derived. The annotations may then be used to generate control signals 1305, or may be processed through machine learning algorithms to detect patterns of movement and create model sequences of such patterns mimicking the movements of sexual activity associated with certain concepts (e.g., frequently-seen movements represented in a certain type of video, or certain sexual activities, or associated with certain actors and actresses, etc.) 1304.

Figure 14:
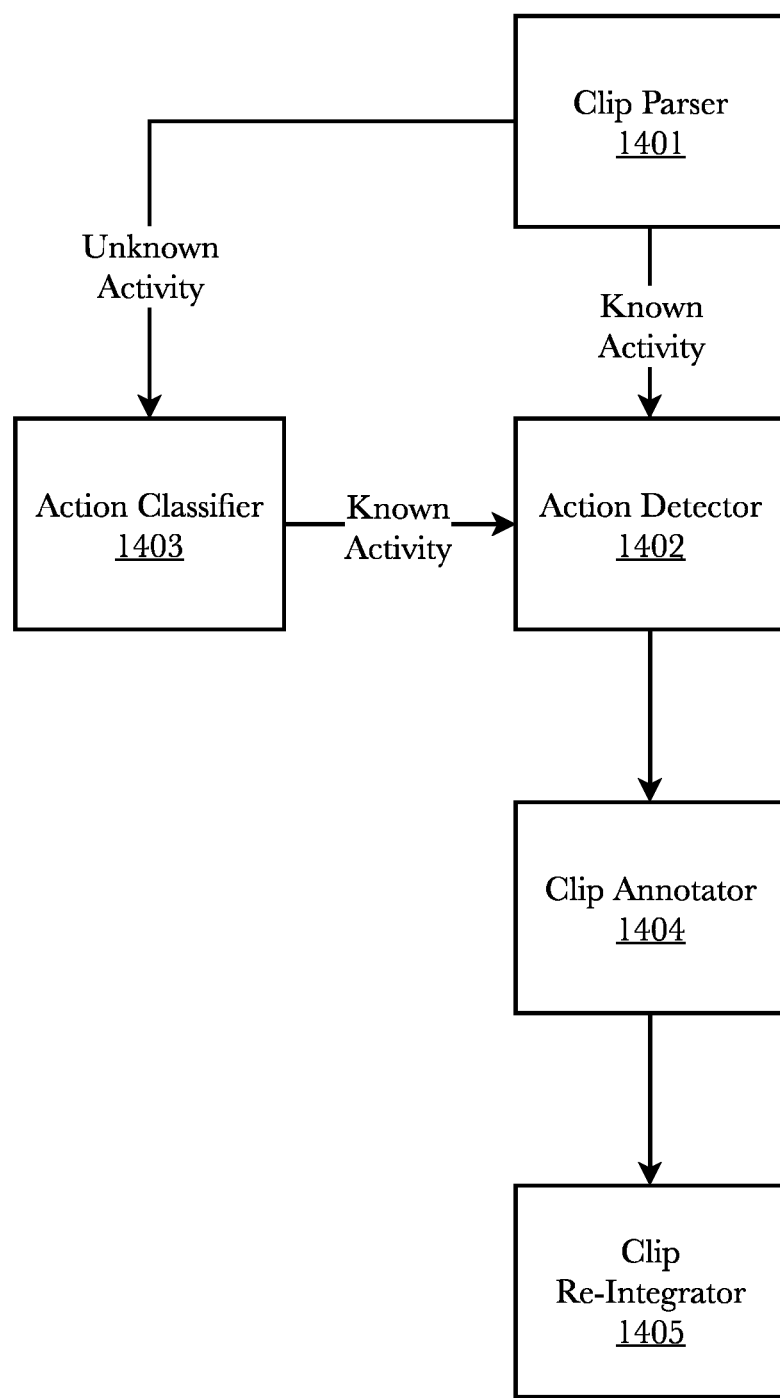
FIG. 14 is a block diagram showing an exemplary system architecture for automated annotation of videos containing depictions of sexual activity.

FIG. 14 is a block diagram showing an exemplary system architecture for automated annotation of videos containing depictions of sexual activity. This exemplary system architecture provides more detail regarding the operation of the video analysis engine 701. In some embodiments, this exemplary system architecture, or a similar one, may be incorporated into the video analysis engine 701 as a component, or as a component of the video parser 801, the metadata processor 803, or the motion translation processor 804. In some embodiments, this system architecture may be distributed among, or substitute for, one or more components of the video analysis engine 701. In some embodiments, this system architecture or it components may exist separately from, but remain accessible to, the video analysis engine 701.

In this exemplary embodiment, a clip parser 1401 parses (i.e., breaks or segments) a video into smaller clips to reduce the scale of the video processing by the machine learning algorithms (i.e., reduces the video to more easily manageable smaller clips of a larger video). Depending on the size of the video, available processing power, and the machine learning algorithm to be used, the clip parser 1401 may reduce the video to any size ranging from the entire video to frame-by-frame clips of the video. Where a video is annotated with known activities (e.g., where the video or segments of the video have been annotated with an indication of the type of activity that is contained therein), the clip parser 1401 may parse the video into clips corresponding to the length of the known activity, as indicated by the annotations. In such cases, the clip parser 1401 forwards the clips of known activity directly to an action detector 1402. Where the video contains depictions of unknown activities, the clip parser will parse the video into uniform sizes (e.g., frame-by-frame, or a certain number of frames representing several seconds or minutes of video), and send the video to an action classifier 1403, which classifies the activities in the video before sending them an known activities to the action detector 1402.

The action classifier 1403 comprises one or more machine learning algorithms that have been trained to classify human actions. Classification of human action is a simpler activity than human action detection. Human action classification involves identification of human objects in the video and some classification of the activity being demonstrated by the human objects (e.g., standing, walking, running, jumping, etc.). Classification does not require a determination of when the action starts, where in the frame the action occurs, or the relative motion of the action; it simply requires that an object in the video be recognized as a person and that the activity of that person be identified.

The action detector 1402 received videos of known sexual activity (i.e., those that have already been classified either manually or using machine learning algorithms), and detects when the action starts, where in the frame the action occurs, or the relative motion of the action. Because the activity in the video is already known, machine learning algorithms may be employed which have been specially-trained for the type of activity depicted in the video. Action detection involves first segmenting the video into objects and backgrounds, identifying human objects in each frame of video, and tracking the movement of those human objects across video frames.

Both action classification and action detection rely on color-based processing of pixels in each frame of the video. Most videos currently available, whether or not depicting sexual activity, are two-dimensional (2D) videos containing color information only (e.g., the RGB color model), from which depth information must be inferred. The additional of depth sensors allows the addition of depth information to the video data (e.g., RGBD color/depth model), which improves human pose estimation but requires specialized sensors that must be used at the time of filming. Due to the processing-intensive nature of analyzing videos using machine learning algorithms, some simplification techniques may be used to reduce the computing power required and/or speed up the processing time. For example, facial recognition algorithms have become widely used, fairly accurate, and can be implemented on computing devices with modest processing power. Thus, for videos where fellatio is known to be the primary sexual activity, facial recognition algorithms may be used as the machine learning component to track the relative position and orientation of the face in the video to indicate the movement component of sexual activity. This greatly reduces the amount of computing power required relative to videos containing unknown sexual activity and/or where whole body human activity must be classified and detected. As there is a limited range of possible sexual activity, and certain sexual activities are more common than others, specially-trained machine learning algorithms can be employed for given types of sexual activity to improve action classification and action detection times and accuracy.

For both action classification and action detection, a variety of machine learning algorithms may be used. For example, as noted above, a convolutional neural network (CNN) may be applied to perform segmentation of each video frame. Other machine learning algorithms or combinations of machine learning algorithms may be employed. For example, a CNN may be employed to extract the features in the video, followed by a long short-term memory (LSTM) algorithm to evaluate the temporal relationships between features. In another example, a three-dimensional CNN (3D CNN) may be employed which can directly create hierarchical representations of spatial and temporal relationships, thus obviating the need to processing through an LSTM. In another example, a two-stream CNN may be used, wherein the first stream of input into the CNN is a set of temporal relationships that are established by a pre-determined set of features, and the second stream is frames from the video. Action classification and/or action detection can be performed by averaging the predictions of the CNN, or by using the output of the CNN for each frame of the video as input to a 3D CNN. Many other variations are possible, and while CNNs are particularly suitable for video processing, other types of machine learning algorithms may be employed.

The clip annotator 1404 associates each video clip with action detection data synchronized with the playback times (or frames) of the video clip, and the clip re-integrator 1405 combines the clips back into the original video received by the clip parser 1401. The annotated video, or just the annotations data from the video, may then be used to generate device control data or may be further processed to extract models of typical sexual activity prior to generating device control data.

Figure 15:
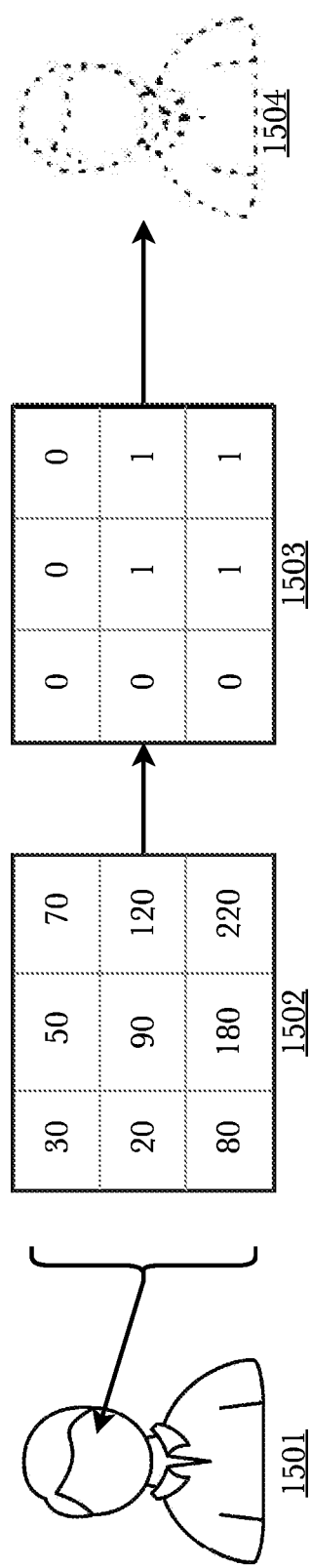
FIG. 15 (PRIOR ART) is a diagram describing the use of the local binary pattern (LBP) algorithm to extract the textural structure of an image for use in object detection.

FIG. 15 (PRIOR ART) is a diagram describing the use of the local binary pattern (LBP) algorithm to extract the textural structure of an image for use in object detection. There are a wide variety of algorithms for extracting data from images and/or video (which is a series of images) for object recognition within the image. The local binary pattern (LBP) algorithm is one of the simplest and easiest to understand, and is therefore used here to demonstrate in general terms how image data is processed to extract certain information. All digital images are composed of pixels, each of which represents the smallest area of viewable information in the image (i.e., each pixel is a "dot" in the image). Each pixel contains information about the color that the dot represents, and the color of the pixel may be either black and white, grayscale, or colored. The representation of the color may be in any number of standard formats (also called color models), with the hexadecimal (HEX), red, green, blue (RBG), and cyan, magenta, yellow, key/black (CMYK) being three of the most common. In this simplified example, the original image 1501 is in 256-bit grayscale, meaning that each pixel in the original image 1501 has a grayscale value of 0-255. The LBP algorithm is applied to each pixel in the original image 1501 by selecting a pixel and comparing the value of that pixel to the value of each surrounding pixel, as shown in the first table of values 1502, in which the selected pixel from the original image 1501 has a value of 90, and the values of the surrounding pixels from top left and going clockwise are 30, 50, 70, 120, 220, 180, 80, and 20. In a next step of the LBP algorithm, for each of the pixels in the first table 1502 is assigned a binary (zero or one) value in a second table 1503, wherein a zero is assigned if the value of the pixel is less than the value of the selected (i.e., center) pixel, and a one is assigned if the value of the pixel is equal to or greater than the value of the selected (i.e., center) pixel. The resulting values are shown in the second table 1503, wherein the pixels with values of 90, 120, 220, and 180 have been assigned a binary value of one, and all of the other pixels have been assigned a value of zero. The values of each of the pixels in the second table 1503 surrounding the selected (i.e., center) pixel are concatenated together in a clockwise manner starting from the top left, resulting in this case in the binary number 00011100. This binary number is then converted back to a decimal number, in this case 28, and this decimal number is substituted in for the value of the selected pixel in the original image 1501, representing a 256-bit grayscale value for the local area in which the selected pixel resides. This process is repeated for all pixels in the original image 1501, resulting in a texturized image 1504 wherein each pixel represents the "texture" of the surrounding pixels from the original image 1501. Many different processing methods can be used on the texturized image to identify features and objects in the texturized image, such division of the image into blocks and extracting histograms of each block, and running the histograms through machine learning algorithms that have been trained to identify features from similar histograms from similar images.

Figure 16:
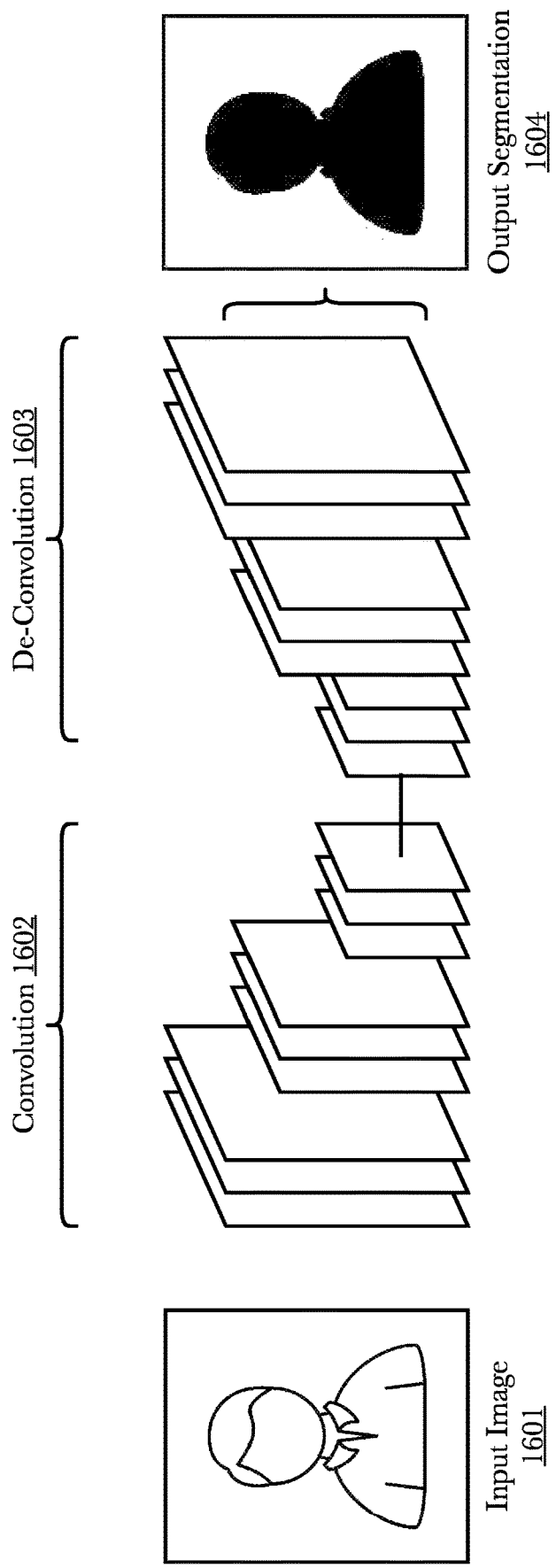
FIG. 16 (PRIOR ART) is a diagram describing the use of a convolutional neural network (CNN) to identify objects in an image by segmenting the objects from the background of the image.

FIG. 16 (PRIOR ART) is a diagram describing the use of a convolutional neural network (CNN) to identify objects in an image by segmenting the objects from the background of the image. Artificial neural networks are computing systems that mimic the function of the biological neural networks that constitute human and animal brains. Artificial neural networks comprise a series of "nodes" which loosely model the neurons in the brain. Each node can pass on a signal to other nodes. The output of each node is some non-linear function of the sum of its inputs, and the probability of a signal being passed to another node depends on the weight assigned to the "edge" between the nodes, which is the connection between the nodes. An artificial neural network finds the correct mathematical relationship between an input and an output by calculating a probability of obtaining the output from the input at each "layer" of mathematical calculations.

Convolutional neural networks are a type of artificial neural network commonly used to analyze imagery that use a mathematical operation called convolution (also called a dot product or cross-correlation) instead of general matrix multiplication as in other types of artificial neural networks. Convolutional neural networks are fully connected, meaning that each node in one layer is connected to every node in the next layer. Each layer of the CNN convolves the input from the previous layer. Each convolutional node processes data only for its receptive field, which is typically a small sub-area of the image (e.g., a 5×5 square of pixels). There may be pooling layers in a CNN which reduce the dimensionality of the data by combining the outputs of node clusters in one layer into a single node in the next layer. Each node in a CNN computes an output value by applying a specific function to the input values coming from the receptive field in the previous layer. The function that is applied to the input values is determined by a vector of weights and a bias. The CNN "learns" by making iterative adjustments to these biases and weights.

In this application of CNNs, an input image 1601 is processed through a CNN in which there are two stages, a convolution stage 1602 and a de-convolution stage 1603, ultimately resulting in an output image 1604 in which objects in the image are segmented (i.e., identified as separate from) the background of the image. In the convolution stage 1602, the image is processed through multiple convolution layers to extract features from the image, and then through a pooling layer to reduce the dimensionality of the data (i.e., aggregation of pixels) for the next round of convolutions. After several rounds of convolution and pooling, the features have been extracted and the data have been reduced to a manageable size. The data are then passed to the de-convolution stage 1603, in which a prediction is made as to whether each pixel or group of pixels represents an object, and passed through several layers of de-convolution before a new prediction is made at a larger level of de-aggregation of the pixels. This process repeats until an output image 1604 is obtained of a similar size as the input image 1601, wherein each pixel of the output image 1604 is labeled with an indication as to whether it represents an object or background.

Figure 17:
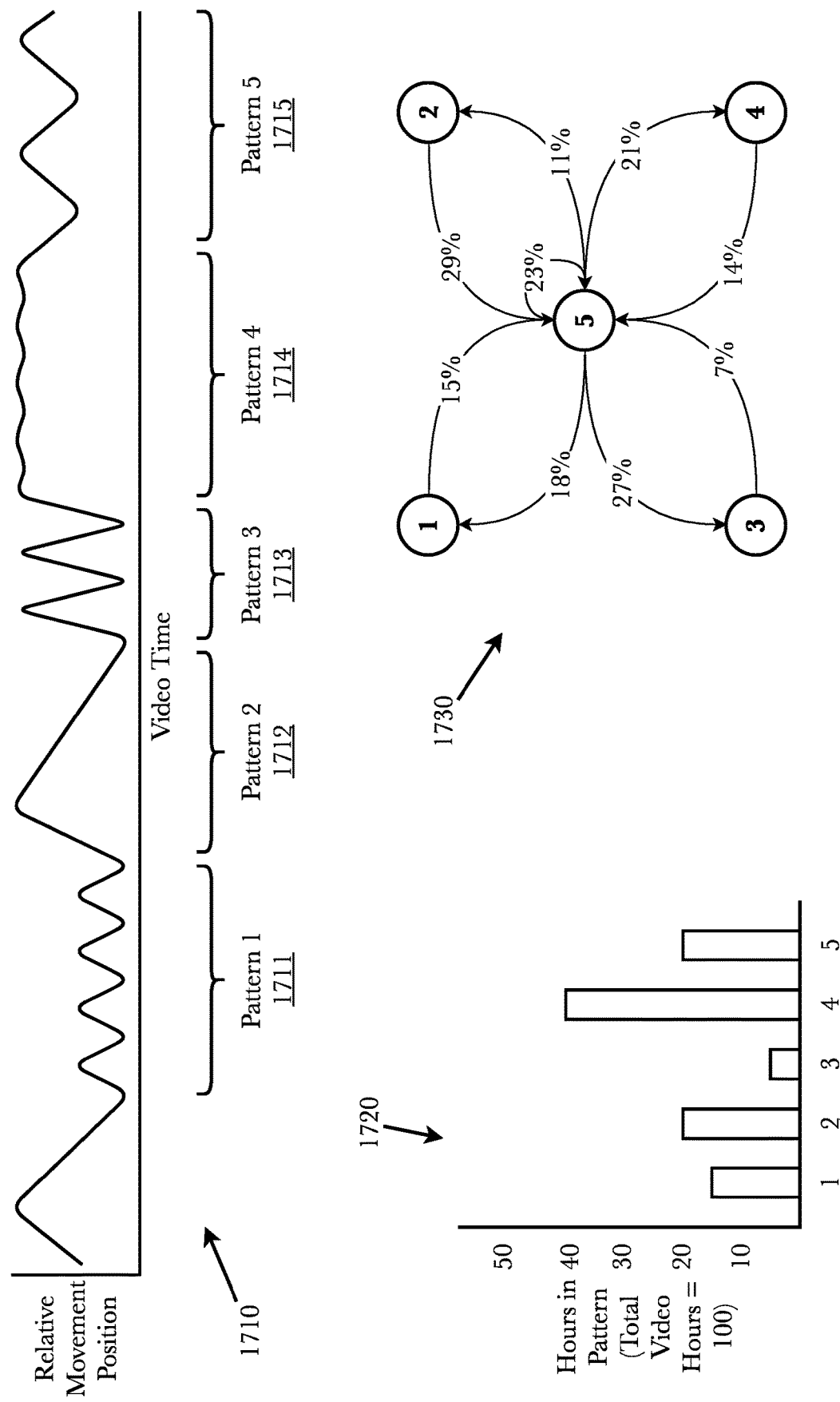
FIG. 17 is a diagram showing exemplary video annotation data collection and processing to develop models of sexual activity sequences.

FIG. 17 is a diagram showing exemplary video annotation data collection and processing to develop models of sexual activity sequences. In a first step, annotation data from videos depicting sexual activity is gathered. The diagram at 1710 shows an exemplary graph created from annotation data from a single video depicting sexual activity. The graph of the annotation data shows the relative position of an object in a single video over time (i.e., movement of the object over time in that video). A number of patterns of movement 1711-1715 can be seen in the graph. When used in conjunction with a single video, the annotation data can be converted directly into device control data for a sexual stimulation device, and the device can be used in synchronization with the video just from the annotation data for that video. However, if models of sexual activity are to be created for use with the sexual stimulation device (e.g., to mimic "typical" sexual activities but without reference to a particular video), additional processing is required to develop models from the annotated data.

To process annotation data to develop models, patterns of movement will ideally be extracted from a larger number of videos. When a machine learning algorithm is fed the annotation data from many such videos, these patterns can be identified across the various videos, and the frequency of these patterns across all videos can be extracted, as shown in the bar chart at 1720. In this bar chart 1720, one hundred total hours of video time was processed through the machine learning algorithm, and the number of hours each pattern of movement 1711-1715 was displayed is shown. For example, Pattern 4 was displayed in a total of 40 hours out of the 100 total hours of video. Machine learning algorithms suitable for this identification of patterns across videos are clustering-type algorithms such as K-means clustering (also known as Lloyd's algorithm), in which movement patterns in the annotation data are clustered into groups containing similar movement patterns. From the clusters, certain types of movement patterns can be identified. For example, in the case of a video depicting fellatio, clusters of movement will show shallow motions around the tip of the penis (e.g., Pattern 4 1714), deep motions around the base of the penis (e.g., Pattern 1), movements along the full length of the penis (e.g., Pattern 3), etc. Such clusters may be visually mapped in 2D or 3D to confirm the consistency and accuracy of the clustering.

Finally, other types of machine learning algorithms may be employed to create models of sexual activity shown in the processed annotation data. In one method, reinforcement learning may be employed to identify the frequency counts of certain patterns of movement, create "states" representing these patterns, and probabilities of transferring from any given state to any other state. An example of such a state diagram is shown at 1730, wherein each state represents one of the patterns of movement 1711-1715, and the lines and percentages indicate the probability of transitioning to a different state. In the diagram at 1730, Pattern 5 1715 is shown as the current state, and probabilities of all possible transitions to and from the current state are shown. In practice, this state diagram 1730 would be expanded to include the probabilities to and from each state to every other state, but this diagram is simplified to show only transitions to and from the current state. From these state transition probabilities, sequences of movement patterns 1711-1715 may be constructed representing models of the "typical" activities shown in the video. If annotation data are processed for selected types of videos (e.g., videos containing certain types of sexual activity, certain actors or actresses, or videos from a certain film studio or director, etc.), the models will be representative of that selected type of video. Alternatively, a wide variety of deep learning algorithms may be used for this process including, but not limited to, dense neural networks, convolutional neural networks, generative adversarial networks, and recurrent neural networks. Each of these types of machine learning algorithms may be employed to identify sequences of the patterns of movement identified in the clustering at the previous stage.

Figure 18:
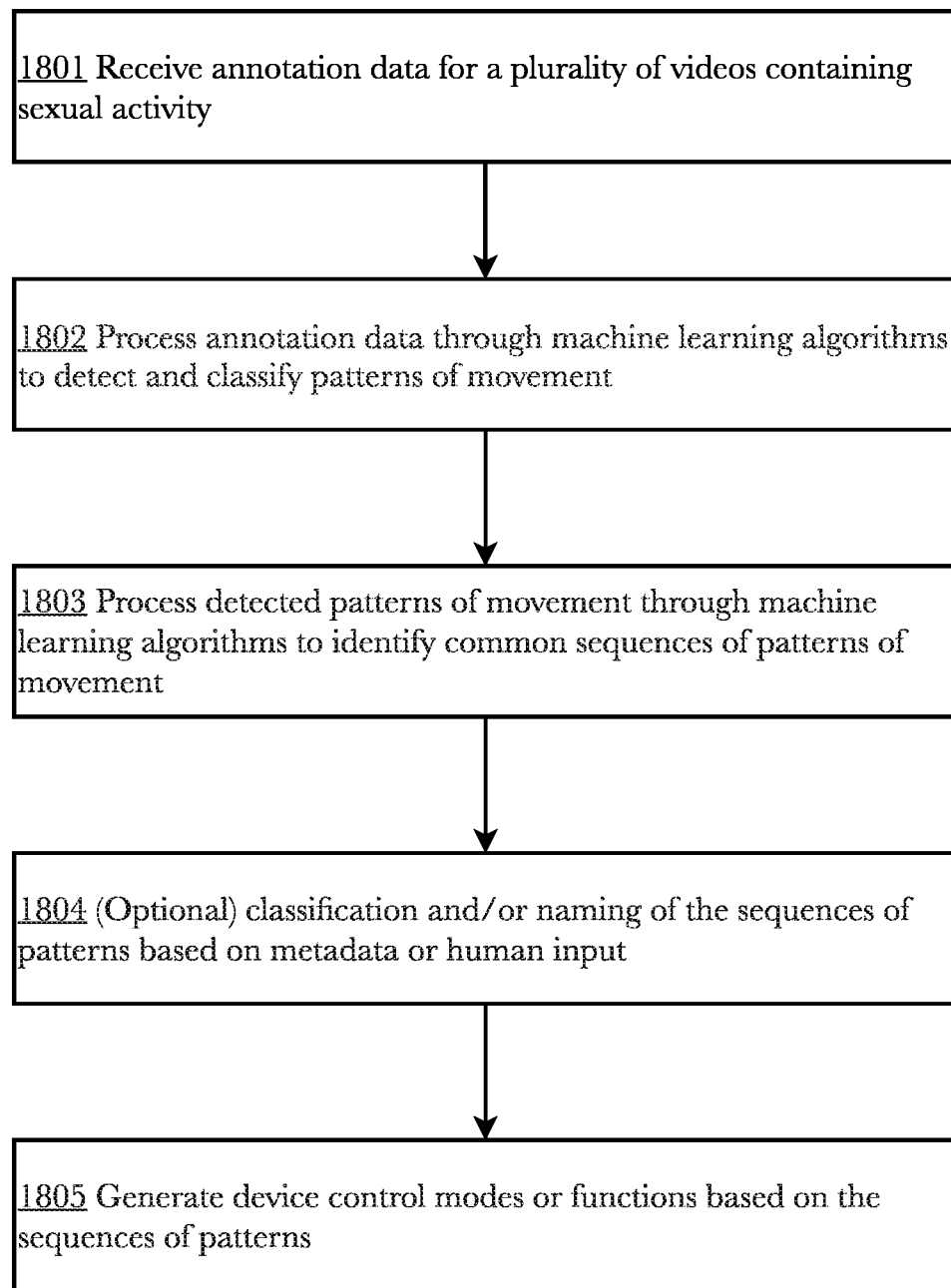
FIG. 18 is a flow diagram showing a method for an exemplary synchronized video control system for sexual stimulation devices.

FIG. 18 is a flow diagram showing a method for developing models of sexual activity sequences from selected videos. In a first step, annotation data are received for a plurality of videos of a particular type (e.g., videos containing certain types of sexual activity, certain actors or actresses, or videos from a certain film studio or director, etc.) 1801. Next, the annotation data are processed machine learning algorithms to detect and classify patterns of movement 1802. Then, the detected patterns of movement are further processed through machine learning algorithms to identify sequences of patterns of movement that are common for that selected type of video 1803, which are then turned into models representative of the types of sexual activity depicted. Optionally, the patterns and sequences of movement may be classified based on metadata associated with the video or based on human input 1804. For example, a particular sequence may be classified as a typical representation of fellatio by a particular adult film star from a certain decade. Lastly, after the models are created, device control modes or functions based on the models may be created 1805 and stored for later use or programmed into the sexual stimulation device.

Figure 19:
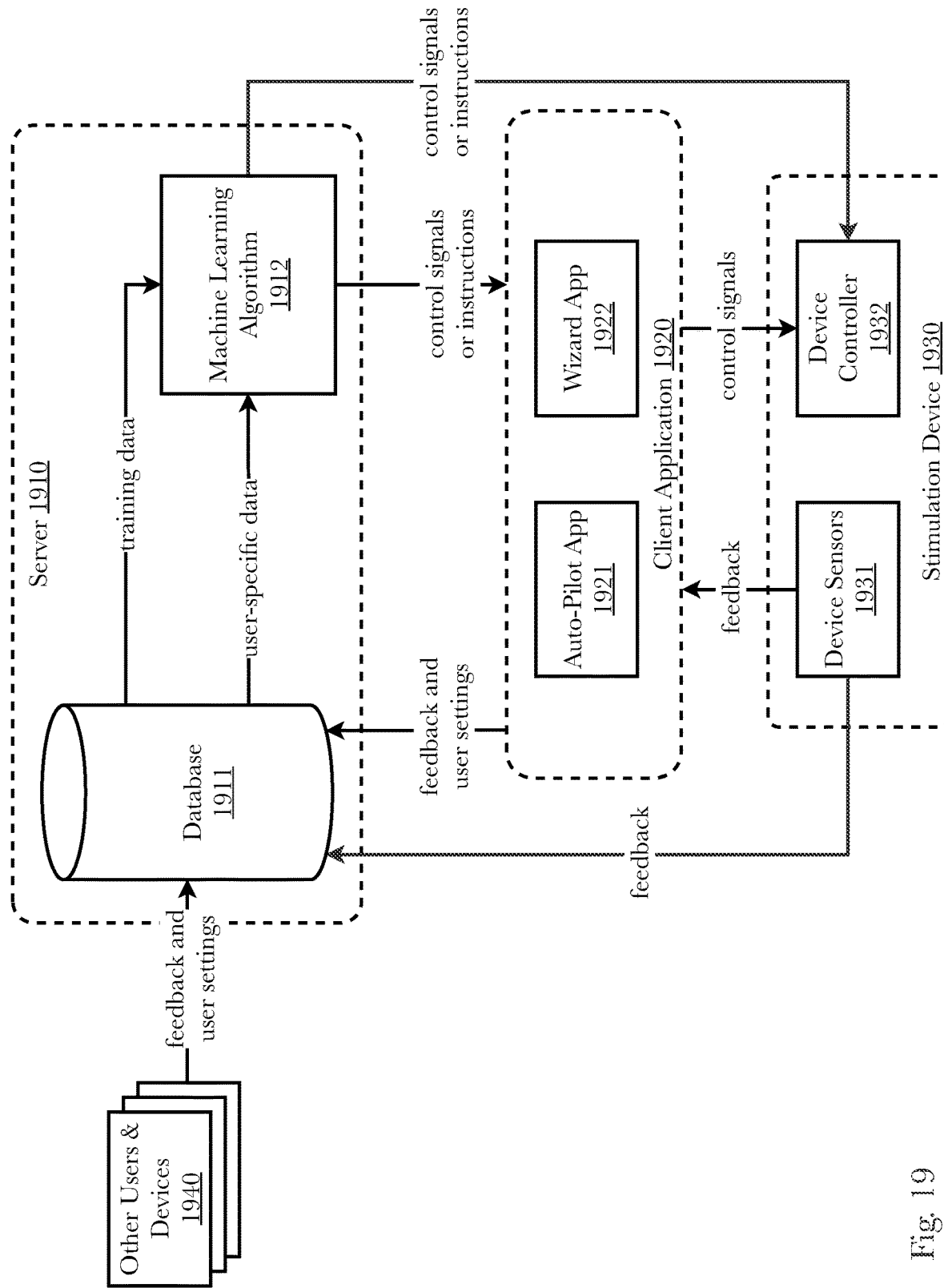
FIG. 19 is an exemplary system architecture diagram for a system for automated control of sexual stimulation devices.

FIG. 19 is an exemplary system architecture diagram for a system for automated control of sexual stimulation devices. In this embodiment, the system comprises a server 1910, a client application 1920, a stimulation device 1930, and data from other users and devices 1940.

The server may be a network-connected, cloud-based, or local server 1910, and comprises a database 1911 for storage of usage data comprising user profiles, user/device feedback, and user/device settings, and a machine learning algorithm 1912 for analysis of the data stored in the database 1911 for generation of automated control signals or instructions. The machine learning algorithm 1912 is trained on the data to identify patterns within the usage data wherein certain characteristics of user profiles are correlated with satisfaction or dissatisfaction with certain aspects of stimulation profiles such as tempo, location, intensity, pressure, and patterns. The usage data may contain user profiles comprising personal information about the user such as age, sex, height, weight, and fitness level; sexual preferences such as straight, gay, bi-sexual, etc.; stimulation preferences such as stimulation tempo/speed, stimulation intensity, location of stimulation, patterns of stimulation; and feedback information such as user ratings, heartrate data from sensors, moisture data from sensors, etc. After training, when a user profile (or one or more characteristics from a user profile) is input into the machine learning algorithm 1912, the machine learning algorithm 1912 generates one or more stimulation profiles (comprising one or more stimulation aspects such as tempo/speed, stimulation intensity, location of stimulation, patterns of stimulation) that correspond with satisfaction based on the characteristics of the user profile input and outputs control signals (or instructions for generating control signals) for stimulation profiles that correspond with satisfaction based on the characteristics of the user profile input. The machine learning algorithm 1912 may periodically or continuously be re-trained based on new data from the client application 1920 (such as, but not limited to, feedback and other changes to the user's profile) and the data from other users and devices 1940 being similarly stored and processed. It should be noted that, while a machine learning algorithm is used in embodiment, the system is not necessarily limited to use of machine learning algorithms and other processes for analysis of the data may be used, including but not limited to modeling and statistical calculations.

The system of this embodiment further comprises a client application 1920, which is a software application operating on a computing device, which may be of any type including but not limited to a desktop computer, tablet, mobile phone, or even a cloud-based server accessible via a web browser. The client application 1920 acts as an interface between the stimulation device 1930 and the machine learning algorithm 1912, relaying feedback from the device to the server 1910 and relaying control signals (or translating instructions into control signals) to the device controller 1932 of the stimulation device 1930. The client application may comprise one or more applications such as the auto-pilot application 1921 and the wizard application 1922. Depending on configuration, the client application may further act as a user interface for operation of, and/or changing settings of, the stimulation device 1930.

In this embodiment, the auto-pilot application 1921 automatically controls the stimulation device 1930 for the user with little or no input from the user. The auto-pilot application stores and retrieves user-specific data for the user of the stimulation device 1930 from a user profile entered into the client application 1920, from sensors on the device (e.g., tumescence sensors, heartrate sensors or heartrate signal receivers, pressure sensors, etc.), and from user interactions with the client application 1920 via a user interface. The data gathered about the user may include such as, but not limited to, where the user prefers to be stimulated, what tempo or speed of stimulation the user prefers, what stimulation patterns the user prefers, and general preferences such as quick stimulation to orgasm, delayed orgasms, multiple edging before orgasm, etc.

The auto-pilot application 1921 provides the user-specific data to the server 1910 and requests control signals (or instructions for control signals) for a stimulation profile that is customized to the user based on the user data. The user-specific data is processed through the trained machine learning algorithm 1912, which selects appropriate stimulation routines and provides control signals or instructions back to the client application for operation of the stimulation device 1930. In some embodiments the control signals or instructions may be sent directly from the machine learning algorithm 1912 directly to the device controller 1932 of the stimulation device 1930. The client application 1920 may be configured to periodically or continuously send updated user-specific data to the server 1910 for processing by the machine learning algorithm 1912 to generate modified or updated control signals or instructions, thus changing and evolving the automated operation of the device based on changed or updated information from the device sensors 1931, client application 1920, or updating/retraining of the machine learning algorithm 1912 based on this user's data and the data from other users and devices 1940 being similarly stored and processed.

In this embodiment, the set-up wizard application 1922 builds an initial personalized stimulation profile from a series of ratings by the user of test stimulations. Completion of the set-up wizard application 1922 process accelerates customization of a stimulation profile for the user by providing a base set of ratings of various aspects of stimulation which can then be processed through the trained machine learning algorithm 1912 to automatically control the stimulation device 1930, as further shown in FIG. 20. After completion of the set-up wizard application 1922, stimulation profiles for the user may continue to evolve from new user-specific data as described above. In some embodiments, the set-up wizard application 1922 and auto-pilot application 1921 operate independently from one another, while in other in other embodiments the set-up wizard application 1922 is the first step in the automated control process, followed by further automation by the auto-pilot application 1921.

In some embodiments, the client application 1920 may exist as an application on a user's mobile phone, and may interface with the stimulation device 1930 via a local network (e.g., WiFi, Bluetooth, etc.). In other embodiments, the client application 1920 may exist as an application on the server 1920 accessible via a user account also residing on the server. In other embodiments, certain components of the server 1910 and client application 1920 may reside on tablet computer or other mobile device, or on the stimulation device 1930 itself (e.g., a copy of the trained machine learning algorithm could reside on a smartphone such that automated generation of control signals can be accomplished without access to the server). In some embodiments, the client application 1920 and/or server components will be integrated into the stimulation device 1930 (e.g., stored in a memory and operable on the device controller 1932) instead of residing on a separate computing device.

The stimulation device 1930 may be any device configured to provide sexual stimulation by any variety of means, including but not limited to, linear stroking, vibration, rotation, heat, electrical stimulation, or combinations of the above. Device sensors 1931 may be any sensor on the device capable of providing data regarding an aspect of sexual arousal, including but not limited to, heartrate sensors, moisture sensors, tumescence sensors, pressure sensors, strain gauges, and length/distance sensors. Further, the device sensors 1931 include devices capable of receiving sensor data from external sensors (e.g., wearable fitness devices that record heart rates) via WiFi, Bluetooth, or other networking technologies. The device controller 1932 is a device capable of operating the stimulation device based on control signals received. The device controller 1932 may be a simple power relay switching device that receives low-powered signals and outputs corresponding power to motors, vibrators, etc., or may be a computing device with a memory, processor, and storage. In the latter case, the device controller 1932 may be configured to receive instructions to generate control signals and generate the control signals, itself. Further, in some embodiments, aspects of the client application and/or machine learning algorithm 1912 may be incorporated into the device controller 1932.

Figure 20:
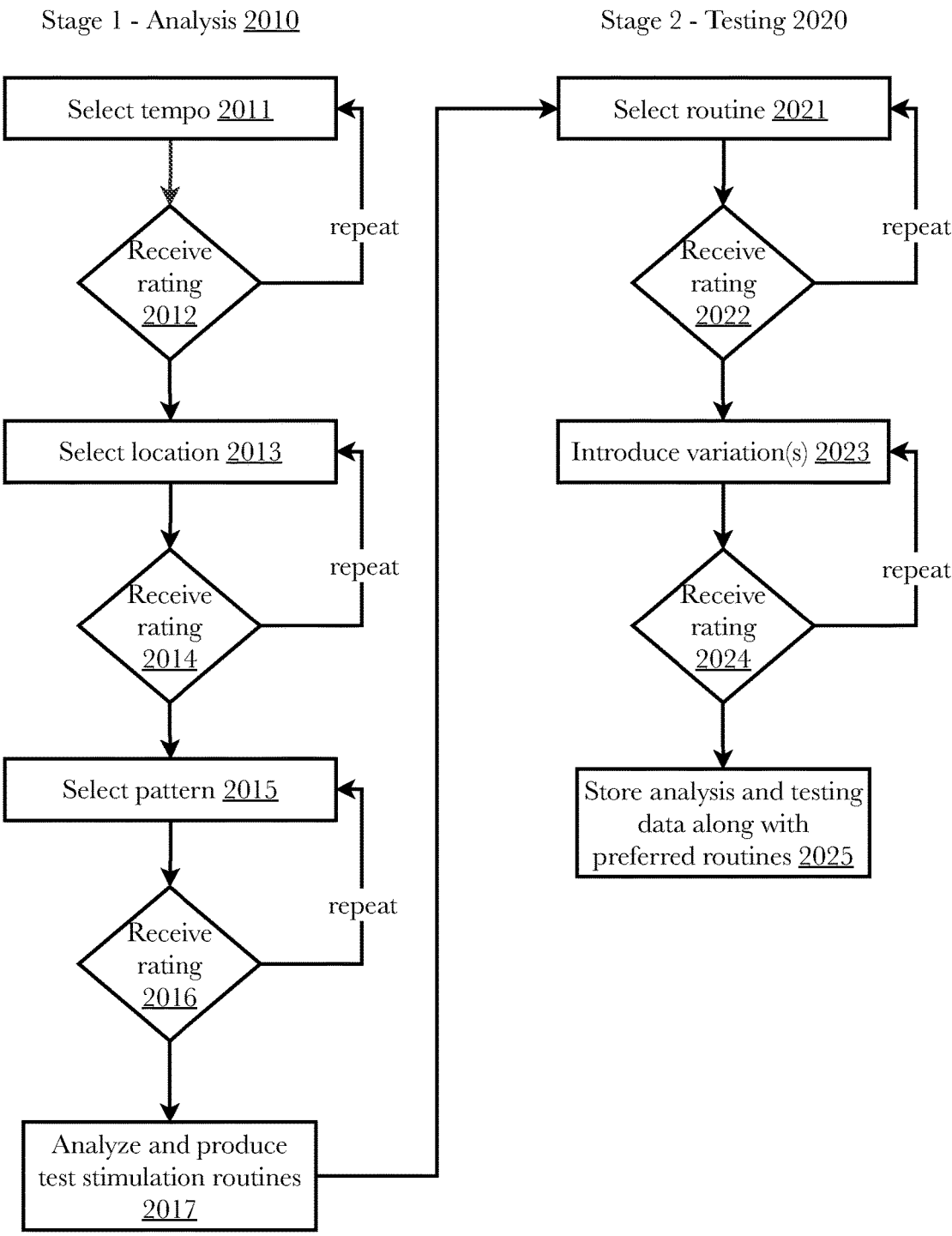
FIG. 20 is an exemplary algorithm for an automated set-up wizard for a system for automated control of sexual stimulation devices.

FIG. 20 is an exemplary algorithm for an automated set-up wizard for a system for automated control of sexual stimulation devices. The set-up wizard application 1922 builds an initial personalized stimulation profile from a series of ratings by the user of test stimulations. Completion of the set-up wizard application 1922 process accelerates customization of a stimulation profile for the user by providing a base set of ratings of various aspects of stimulation which can then be processed through the trained machine learning algorithm 1912 to automatically control the stimulation device 1930. After completion of the set-up wizard application 1922, stimulation profiles for the user may continue to evolve from new user-specific data as described above.

In this embodiment, the set-up wizard application 1922 process has two stages, an analysis stage and a testing stage. At the analysis stage 2010 stimulation selections are made from a set of pre-programmed aspects such as tempo, location, and pattern, and the user's ratings for each selection are used by the machine learning algorithm 1912 to generate a stimulation routine comprising one or more tempos, locations, and patterns of stimulation. At the testing stage 2020, stimulation is performed using the generated stimulation routine, and the generated stimulation routine is refined through ratings by the user and, optionally, introduction of variations deemed likely to improve those ratings. Optionally, the generated stimulation routine may be displayed on a user interface such as that shown in FIG. 21, and additional refinements may be made by manual adjustments to the routine by the user using the user interface.

In this exemplary process, the process begins at the analysis stage 2010 with the system's selection of one or more tempos of stimulation 2011 from a set of pre-programmed (or randomly chosen) and user ratings 2012 for each selected tempo. On each attempt, the tempo is changed and a new rating is obtained. For example, if the system selects a slow tempo, and the user gives it a low rating, the system may select a faster tempo for the next selection and rating. Once a tempo, or range of tempos, is established, the system goes through the same process for location 2013 and user ratings associated with location 2014 using that tempo, and again with patterns of stimulation 2015 and user ratings 2016 based around the established tempo and established location. For a device capable of producing linear stroking motions, the patterns of stimulation may include, but are not limited to, variations in the established tempo, variations in the established location, stopping or starting of stimulation at various timings, and stimulation outside of the established tempo and established location for a period of time before returning to them. The user's ratings of the tempo, location, and patterns of stimulation are processed through the machine learning algorithm 1912 to generate one or more test stimulation routines 2017 for testing. At the testing stage 2020, a routine is selected 2021 from the one or more test stimulation routines 2017 and rated by the user 2022. This process may be repeated for several test stimulation routines 2017. In some cases (for example when only a single test stimulation routine is generated or where the test routines are all rated poorly by the user), the system may introduce variations in one or more of the test routines 2023 in an attempt to increase the user's rating 2024 of that test routine. The variations come from any number of sources, including but not limited to, a list of known variations, variations generated by the machine learning algorithm 1912, and random variation. Once the testing stage 2020 is completed, one or more preferred stimulation routines are stored, along with the analysis and testing data for future use 2025.

Figure 21:
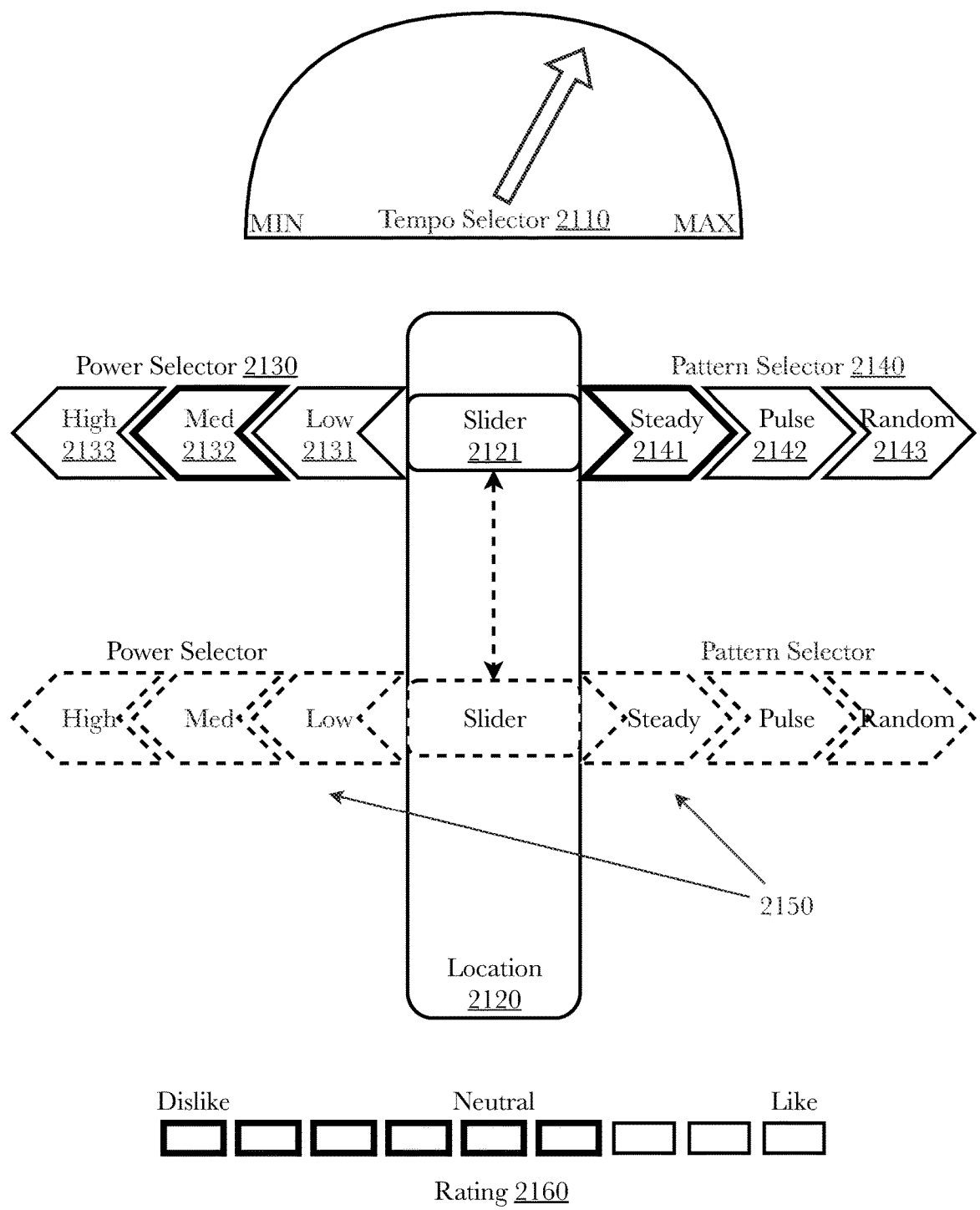
FIG. 21 is an exemplary screenshot of a user interface for viewing, adjustment, and rating of automated control settings for a sexual stimulation device.

FIG. 21 is an exemplary screenshot of a user interface for viewing, adjustment, and rating of automated control settings for a sexual stimulation device. During manual operation of the stimulation device 1930, various aspects of the current stimulation being provided by the stimulation device 1930 are displayed on an appropriate display or computing device, and the controls for each aspect may be adjusted by the user according to preference. During automated operation of the stimulation device 1930, various aspects of the operation of the stimulation device 1930 are displayed, reflecting the current stimulation routine. Each of the aspects displayed can be changed by the user to manually override the current settings, and the manually-overridden settings will be provided to the client application 1930 or server 1910 for adjustment of the current stimulation routine according (and for evolution of that user's preferred stimulation routines). During the set-up wizard application 1922 process, these displays and controls 2110-2160 may be used to adjust and rate the aspect of stimulation under test.

In this example, it is assumed that the current stimulation routine is being displayed on a mobile phone or tablet device with a touch screen, although the system is not so limited. In this screenshot, a tempo selector 2110 is shown with an arrow indicating the current tempo of stimulation on a range from minimum to maximum. The tempo arrow can be moved by the user to override the tempo setting of the current stimulation routine, and the override information will be forwarded to the client application or server 1910 for adjustment of the current stimulation routine and evolution of the user's stimulation preferences over time. A location selector 2120 is shown with an slider 2121 indicating the current location of stimulation (here on a device that provides stimulation using a reciprocal linear motion). The slider 2121 can be moved by the user to override the location setting of the current stimulation routine, and the override information will be forwarded to the client application or server 1910 for adjustment of the current stimulation routine and evolution of the user's stimulation preferences over time. At the location indicated by the slider 2121, a power selector 2130 displays the current power setting for that location and allows the user to adjust the power setting for that location, and a pattern selector 2140 displays the current pattern setting for that location and allows the user to adjust the pattern setting for that location. A different position of the slider is shown at 2150, along with the power selector 2130 and pattern selector 2140 for that different location. A rating bar 2160 is shown at the bottom of the screen, allowing the user to input a rating for the current stimulation.

Figure 22:
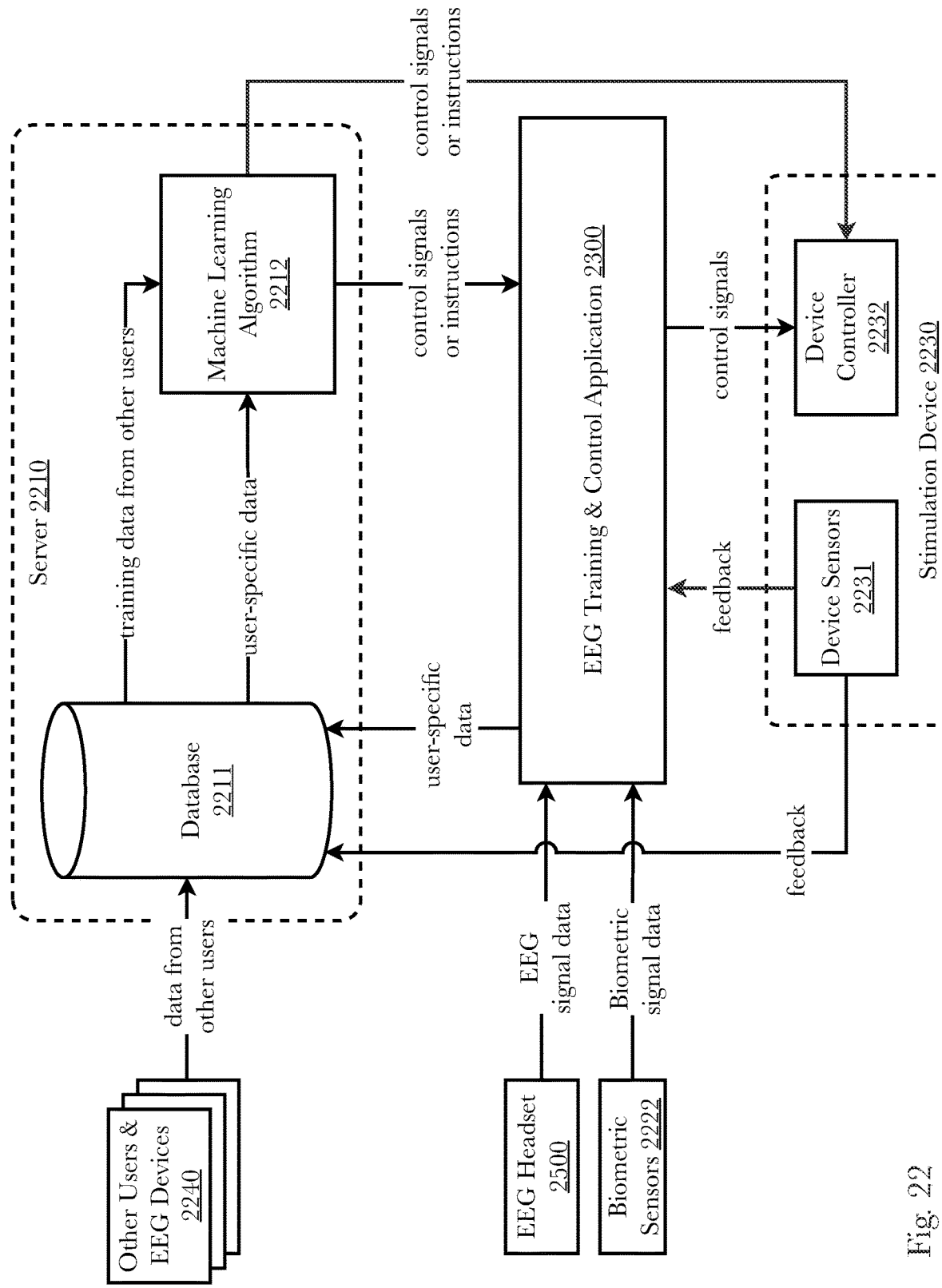
FIG. 22 is an exemplary system architecture diagram for a system for thought-based control of sexual stimulation devices.

FIG. 22 is an exemplary system architecture diagram for a system for thought-based control of sexual stimulation devices. In this embodiment, the system comprises a server 2210, an electroencephalograph (EEG) training and control application 2300, an EEG headset, one or more other biometric sensors, a stimulation device 2230, and data from other users and EEG devices 2240.

The server may be a network-connected, cloud-based, or local server 2210, and comprises a database 2211 for storage of user data comprising EEG brain activity patterns and control setting associations 2211, and a machine learning algorithm 2212 for analysis of the data stored in the database 2211 for generation of thought-based control signals or instructions. The machine learning algorithm 2212 is trained on the data to identify patterns within the usage data wherein certain EEG patterns are correlated with stimulation device controls and/or biometric sensor data. The user data may further contain user profiles comprising personal information about the user such as age, sex, height, weight, and fitness level; sexual preferences such as straight, gay, bisexual, etc.; stimulation preferences such as stimulation tempo/speed, stimulation intensity, location of stimulation, patterns of stimulation; and feedback information such as user ratings, other biometric sensor data such as heartrate data from sensors, moisture data from sensors, etc.; all of which may be incorporated by the machine learning algorithm to better correlate EEG patterns with stimulation device controls for specific users. After training, when an EEG pattern from the EEG headset is input into the machine learning algorithm 2212, the machine learning algorithm 2212 generates one or more control signals or instructions for the stimulation device 2230 based on the associations between EEG patterns and control settings learned by the machine learning algorithm during training. The machine learning algorithm 2212 may periodically or continuously be re-trained based on new data from the electroencephalograph (EEG) training and control application 2300 (such as, but not limited to, new training data acquired as a result of additional EEG training by the user) and the data from other users and EEG devices 2240 being similarly stored and processed. It should be noted that, while a machine learning algorithm is used in embodiment, the system is not necessarily limited to use of machine learning algorithms and other processes for analysis of the data may be used, including but not limited to modeling and statistical calculations. For example, in some embodiments, the machine learning aspect may be bypassed altogether, having the system rely only on EEG pattern/control signal associations from the user-specific training conducted by the EEG training & control application 2300. In other embodiments, a two-stage training algorithm may be used wherein the machine learning algorithm is first trained generically on a large number of users, then re-trained for a particular user using user-specific training data. In some embodiments, control signals for the stimulation device may be based on a combination of non-machine learning algorithm EEG pattern/control signal associations and machine learning algorithm EEG pattern/control signal associations.

The system of this embodiment further comprises a electroencephalograph (EEG) training and control application 2300, which is a software application operating on a computing device, which may be of any type including but not limited to a desktop computer, tablet, mobile phone, or even a cloud-based server accessible via a web browser. The electroencephalograph (EEG) training and control application 2300 acts as an interface between the stimulation device 2230, the machine learning algorithm 2212, and the EEG headset 2500 and other biometric sensors 2222, as well as operating to train the system to make associations between EEG patterns and control signals for a particular user or users. In its role as an interface, the EEG training and control application 2300 relays feedback from the device to the server 2210 and relays control signals (or translates instructions into control signals) to the device controller 2232 of the stimulation device 2230. Details regarding the architecture and operation of the EEG training and control application 2300 are further described below. Depending on configuration, the electroencephalograph (EEG) training and control application 2300 may further act as a user interface for operation of, and/or changing settings of, the stimulation device 2230. In its role as an EEG training application, the EEG training and control application 2300 assigns training tasks to the user, receives EEG signal data comprising measurements of electrical activity in parts of the user's brain from the EEG headset 2500, and associates patterns of EEG signal data with objectives of the training tasks (e.g., think about moving an on-screen control downward, corresponding to a reduction in the speed or intensity of operation of the stimulation device).

In this embodiment, the EEG headset 2500 is worn by a user and sends EEG signal data from electrodes of the EEG headset to the EEG training & control application 2300. The user data may further comprise biometric signals data from other biometric sensors 2222. EEG signal data is a form of biometric data, but other biometric sensors 2222 may be used to provide biometric signal data that is not associated with brain activity, such as external or third-party heartrate monitors that provide heartrate data.

The EEG training and control application 2300 provides the user-specific data comprising EEG patterns, or control associations, or both to the server 2210 and requests control signals (or instructions for control signals) for the stimulation device 2230 based on the user-specific data. During training of the machine learning algorithm, the EEG patterns and control associations are used as a form of labeled training data to train or re-train the machine learning algorithm 2212. After training, the EEG patterns may be processed through the trained machine learning algorithm 2212, which provides control signals or instructions back to the electroencephalograph (EEG) training and control application for operation of the stimulation device 2230. In some embodiments, the EEG patterns are sent to the machine learning algorithm 2212 and processed into control signals in real time or near real time. In some embodiments the control signals or instructions may be sent directly from the machine learning algorithm 2212 directly to the device controller 2232 of the stimulation device 2230. The electroencephalograph (EEG) training and control application 2300 may be configured to periodically or continuously send updated user-specific data to the server 2210 for processing by the machine learning algorithm 2212 to generate modified or updated control signals or instructions, thus changing and evolving the automated operation of the device based on changed or updated information from the device sensors 2231, electroencephalograph (EEG) training and control application 2300, or updating/retraining of the machine learning algorithm 2212 based on the user's data and the data from other users and EEG devices 2240 being similarly stored and processed.

In some embodiments, the electroencephalograph (EEG) training and control application 2300 may exist as an application on a user's mobile phone, and may interface with the stimulation device 2230 via a local network (e.g., WiFi, Bluetooth, etc.). In other embodiments, the electroencephalograph (EEG) training and control application 2300 may exist as an application on the server 2300 accessible via a user account also residing on the server. In other embodiments, certain components of the server 2210 and electroencephalograph (EEG) training and control application 2300 may reside on tablet computer or other mobile device, or on the stimulation device 2230 itself (e.g., a copy of the trained machine learning algorithm could reside on a smartphone such that automated generation of control signals can be accomplished without access to the server). In some embodiments, the electroencephalograph (EEG) training and control application 2300 and/or server components will be integrated into the stimulation device 2230 (e.g., stored in a memory and operable on the device controller 2232) instead of residing on a separate computing device.

The stimulation device 2230 may be any device configured to provide sexual stimulation by any variety of means, including but not limited to, linear stroking, vibration, rotation, heat, electrical stimulation, or combinations of the above. Device sensors 2231 may be any sensor on the device capable of providing data regarding an aspect of sexual arousal, including but not limited to, heartrate sensors, moisture sensors, tumescence sensors, pressure sensors, strain gauges, and length/distance sensors. Further, the device sensors 2231 include devices capable of receiving sensor data from external sensors (e.g., wearable fitness devices that record heart rates) via WiFi, Bluetooth, or other networking technologies. The device controller 2232 is a device capable of operating the stimulation device based on control signals received. The device controller 2232 may be a simple power relay switching device that receives low-powered signals and outputs corresponding power to motors, vibrators, etc., or may be a computing device with a memory, processor, and storage. In the latter case, the device controller 2232 may be configured to receive instructions to generate control signals and generate the control signals, itself. Further, in some embodiments, aspects of the electroencephalograph (EEG) training and control application and/or machine learning algorithm 2212 may be incorporated into the device controller 2232.

Figure 23:
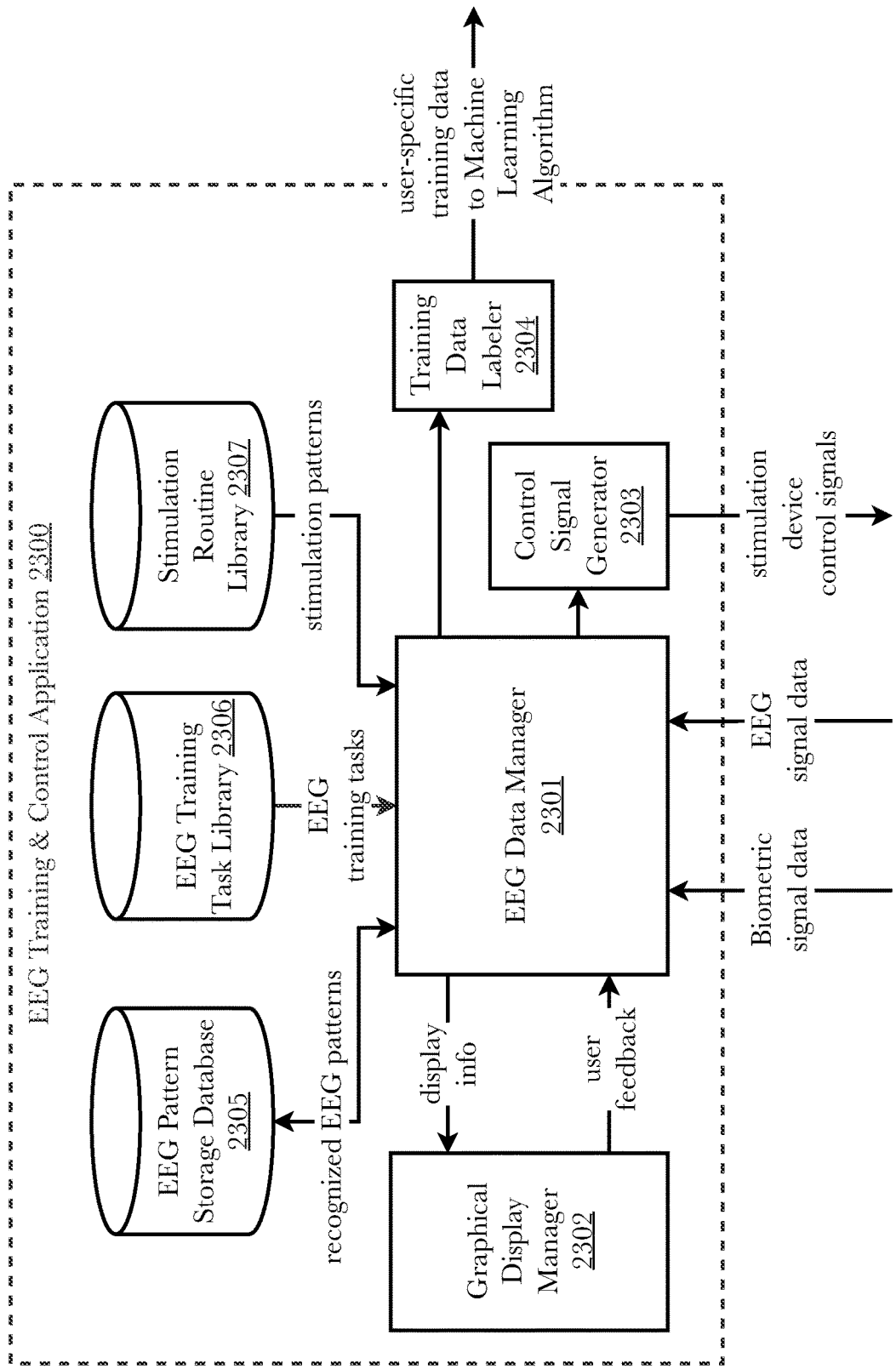
FIG. 23 is an exemplary system architecture diagram for an electroencephalograph training and control application aspect of a system for thought-based control of sexual stimulation devices.

FIG. 23 is an exemplary system architecture diagram for an electroencephalograph training and control application aspect of a system for thought-based control of sexual stimulation devices. The electroencephalograph (EEG) training and control application 2300 is a software application operating on a computing device, which may be of any type including but not limited to a desktop computer, tablet, mobile phone, or even a cloud-based server accessible via a web browser. The EEG training and control application 2300 acts as an interface between the stimulation device 2230, the machine learning algorithm 2212, and the EEG headset 2500 and other biometric sensors 2222, as well as operating to train the system to make associations between EEG patterns and control signals for a particular user or users. In its role as an interface, the EEG training and control application 2300 relays feedback from the device to the server 2210 and relays control signals (or translates instructions into control signals) to the device controller 2232 of the stimulation device 2230. Details regarding the architecture and operation of the EEG training and control application 2300 are further described below. Depending on configuration, the EEG training and control application 2300 may further act as a user interface for operation of, and/or changing settings of, the stimulation device 2230. In its role as an EEG training application, the EEG training and control application 2300 assigns training tasks to the user, receives EEG signal data comprising measurements of electrical activity in parts of the user's brain from the EEG headset 2500, and associates patterns of EEG signal data with objectives of the training tasks (e.g., think about moving an on-screen control downward, corresponding to a reduction in the speed or intensity of operation of the stimulation device). The EEG training and control application 2300 of this embodiment comprises an EEG data manager 2301, a graphical display manager 2302, a control signal generator 2303, a training data labeler 2304, and three databases, an EEG pattern storage database 2305, an EEG training task library 2306, and a stimulation routine library 2307.

Depending on its configuration, the EEG data manager 2301 is responsible for generation of labeled training data to the machine learning algorithm for supervised learning, pass-through of EEG signal data to the machine learning algorithm for unsupervised learning, receipt of control signals from the trained machine learning algorithm based on pass-through of EEG signal data, or generating control signals by direct association of EEG patterns with objectives corresponding to device controls, or any combination of the above. In this embodiment, it is assumed that the EEG data manager is configured to generate EEG pattern/objective pairs either to directly generate control signals itself, or to pass those EEG pattern/objective pairs to the machine learning algorithm for training. In other configurations, however, the EEG data manager may pass through EEG signal data to the machine learning algorithm for unsupervised learning in which the machine learning algorithm identifies the EEG patterns and makes associations with the objectives. In cases involving complex and/or voluminous data such as detecting patterns in EEG signal data, unsupervised learning is often useful in that it can find hidden or difficult-to-identify patterns in the data that might otherwise be missed.

The EEG data manager 2301 retrieves and implements EEG training tasks from the EEG training task library 2306. The training tasks comprise a stimulus such as auditory, visual cues, or sexual stimulation, an objective such as moving a virtual slider displayed on a screen, and instructions for the user to attempt to achieve the objective using some mental image or thought. For example, a training task may involve displaying a task on a visual display using the graphical display manager, wherein the display shows a vertical sliding controller and the instructions may instruct the user to think about moving the vertical sliding controller upward (representing increased speed or intensity of some aspect of the stimulation device) or downward (representing decreased speed or intensity of some aspect of the stimulation device). While the user is performing the task, the EEG headset 2500 detects electrical signals representing brain activity of the user underneath each electrode and forwards those electrical signals as EEG signal data to the EEG data manager 2301. The EEG data manager 2301 receives EEG signal data from the EEG headset 2500 and identifies a pattern of EEG activity from the EEG signal data. The pattern of EEG activity (aka an EEG pattern) may be a spatial pattern (i.e., differences in electrical signals among electrodes spaced across the user's head), a temporal pattern (i.e., changes in the electrical signal in each electrode over time), or both. The EEG data manager 2301 associates the EEG pattern or patterns with an objective of the task (e.g., moving of the vertical control slider downward), creating EEG pattern/objective pairs that can be used either to generate controls for the stimulation device via a control signal generator 2303 or as labeled training data via a training data labeler 2304. The EEG pattern/objective pairs may be stored in the EEG pattern storage database 2305. In some embodiments, new EEG pattern/objective pairs may be compared with stored EEG pattern/objective pairs to confirm, reject, or modify associations.

In some embodiments, the stimulus for some EEG training tasks may comprise stimulation via the stimulation device as a supplement to auditory or visual tasks, or as an alternative thereto. The EEG data manager 2301 may select one or more stimulation routines from a stimulation routine library 2307, apply the stimulation to the user via the stimulation device 2230, and have the user think about an objective related to the stimulation. For example, the EEG data manager 2301 may initiate stimulation at a low speed or intensity, and ask the user to think about increasing the stimulation speed or intensity. In some cases, the objective may simply be free association of the stimulation with certain of the user's thoughts. Similarly to the EEG training for auditory and visual tasks, the EEG data manager 2301 associates the EEG pattern or patterns with an objective of the stimulation (e.g., increasing the speed or intensity of stimulation), creating EEG pattern/objective pairs that can be used either to generate controls for the stimulation device via a control signal generator 2303 or as labeled training data via a training data labeler 2304. The EEG pattern/objective pairs may be stored in the EEG pattern storage database 2305. In some embodiments, new EEG pattern/objective pairs may be compared with stored EEG pattern/objective pairs to confirm, reject, or modify associations.

In some embodiments, the associations may further incorporate biometric signal data from other biometric sensors 2222, creating more complex associations which may be stored as tables, high dimensional vectors, graphs, or other forms of complex relationship storage. In some cases, the user may provide additional user feedback via the graphical display manager 2302 by interacting with the display. Such user feedback may be, for example, indicating a level of concentration the user was able to apply, a mood of the user, or a tiredness level of the user, which user feedback may be used as additional association information.

The more complex the association data between EEG patterns, tasks, feedback, and stimulation routines, the more useful the machine learning algorithm 2212 is in determining relationships between the input data (e.g., EEG signals, biometric signals, user feedback) and the intended outputs (i.e., control of some aspect of the stimulation device).

FIG. 24 is an exemplary algorithm for electroencephalograph data capture and machine learning algorithm training for thought-based control of sexual stimulation devices. This exemplary algorithm comprises three stages, training on curated data 2410, capture of, and training on, user-specific data using visual tasks 2420, and capture of, and training on, user-specific data using stimulation tasks 2430. While in this exemplary algorithm the stages are shown as sequential, in some embodiments these and other stages or training could be used individually or in other combinations.

Stage 1 of this embodiment comprises training the machine learning algorithm generically (i.e., for a typical, unspecified user) using pre-labeled data from other users 2411 who have performed EEG training tasks using their own EEG devices. This pre-labeled training data does not necessarily have to be in the field of control of sexual stimulation devices, and may be pre-labeled training data from control of other devices or performance of other tasks (e.g., biofeedback relaxation routines, mediation, etc.), as long as there is some association in the pre-labeled data between EEG patterns and some objective that could be translated or applied to control of devices.

Stage 2 of this embodiment comprises user-specific EEG training using visual tasks 2420. A visual EEG training task is selected and displayed on a display of a computing device 2421. The training task comprises visual cues with instructions for the user to associate the visual cues with some mental image or thought. For example, the training task may involve displaying a task on a computer screen or other visual display of a computing device, wherein the display shows a vertical sliding controller and the instructions may instruct the user to think about moving the vertical sliding controller upward (representing increased speed or intensity of some aspect of the stimulation device) or downward (representing decreased speed or intensity of some aspect of the stimulation device). While the user is performing the task, an EEG headset 2500 detects electrical signals representing brain activity of the user underneath each electrode and forwards those electrical signals as EEG signal data, which is received and recorded 2422. The visual display is updated with progress of the user in accomplishing the task (for example, where the user's EEG patterns match expected EEG patterns stored in the EEG pattern storage database 2300) or simply updated with an impression of progress designed to encourage the user to continue exhibiting the same EEG patterns 2423. The EEG patterns are associated with the task objective 2424. The pattern of EEG activity (aka an EEG pattern) may be a spatial pattern (i.e., differences in electrical signals among electrodes spaced across the user's head), a temporal pattern (i.e., changes in the electrical signal in each electrode over time), or both. The EEG data manager 2301 associates the EEG pattern or patterns with an objective of the task (e.g., moving of the vertical control slider downward), creating EEG pattern/objective pairs that can be used either to generate controls for the stimulation device 2425 or as labeled training data for use in training a machine learning algorithm 2440. The EEG pattern/objective pairs may be stored in an EEG pattern storage database 2305. In some embodiments, new EEG pattern/objective pairs may be compared with stored EEG pattern/objective pairs to confirm, reject, or modify associations. The process may be repeated until a desired quantity of data is obtained.

Stage 3 of this embodiment comprises user-specific EEG training using stimulation tasks 2430, comprising stimulation via the stimulation device. A stimulation routine is selected from a stimulation routine library 2307, applied to the user via the stimulation device 2230, and the user is asked to think about an aspect of the stimulation or make some other mental association with the stimulation (e.g., an image, feeling, etc.) 2431. For example, the stimulation may be initiated at a low speed or intensity, and the user may be asked to think about increasing the stimulation speed or intensity. Similarly to the EEG training for visual tasks, the EEG pattern or patterns are associated with an objective of the stimulation (e.g., increasing the speed or intensity of stimulation), creating EEG pattern/objective pairs that can be used either to generate controls for the stimulation device 2425 or as labeled training data for use in training a machine learning algorithm 2440. The EEG pattern/objective pairs may be stored in an EEG pattern storage database 2305. In some embodiments, new EEG pattern/objective pairs may be compared with stored EEG pattern/objective pairs to confirm, reject, or modify associations. The process may be repeated until a desired quantity of data is obtained.

The more complex the association data between EEG patterns, tasks, feedback, and stimulation routines, the more useful the machine learning algorithm 2212 is in determining relationships between the input data (e.g., EEG signals, biometric signals, user feedback) and the intended outputs (i.e., control of some aspect of the stimulation device).

Figure 25:
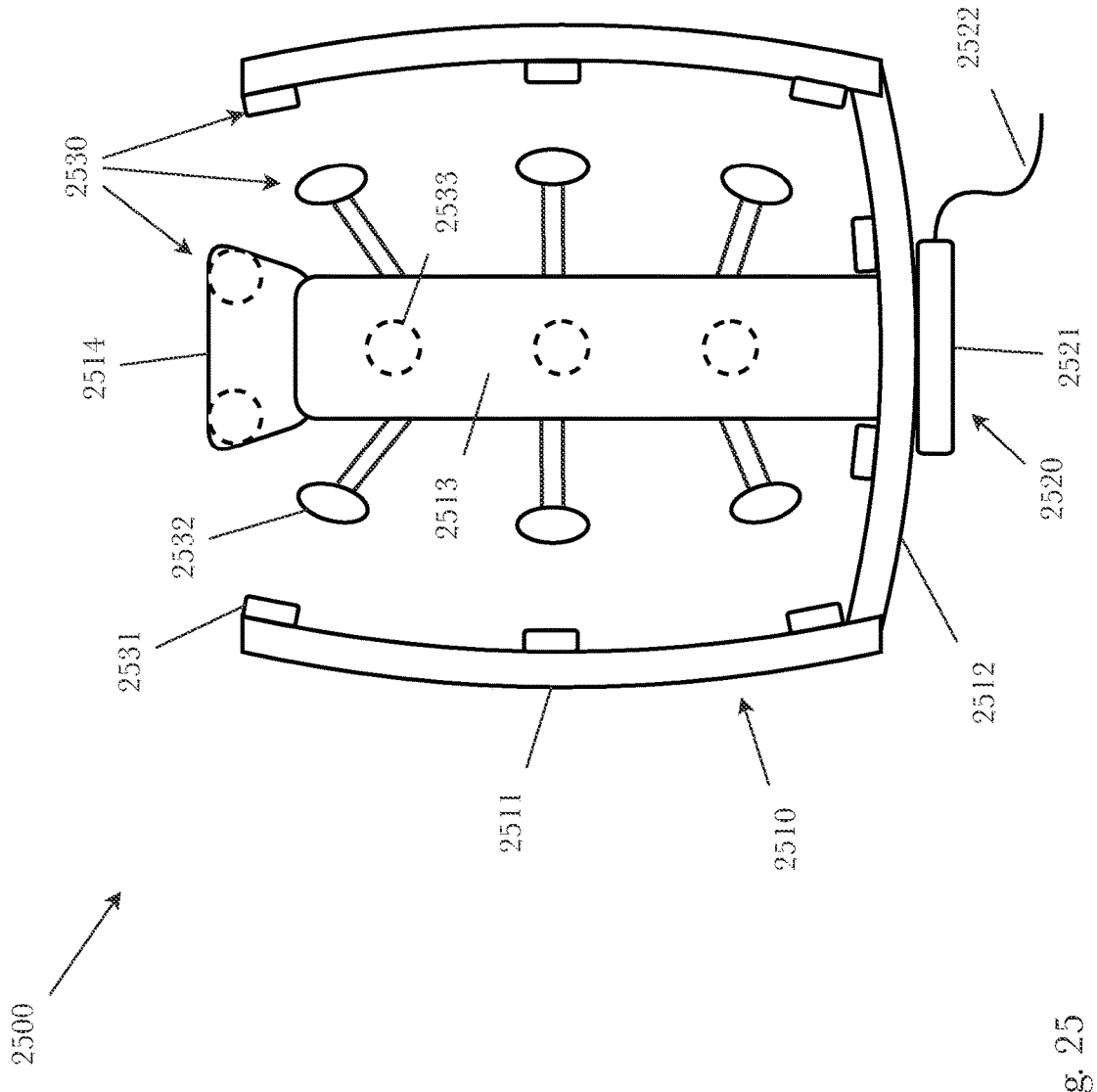
FIG. 25 is an exemplary illustration of an electroencephalograph headset for use in thought-based control of sexual stimulation devices.

FIG. 25 is an exemplary illustration of an electroencephalograph (EEG) headset for use in thought-based control of sexual stimulation devices. An EEG headset 2500 is a device intended to be worn on the head of a person which places electrodes on the person's head for the purpose of measuring electrical signals generated by the brain underneath the location of each electrode. This exemplary illustration shows an EEG headset 2500 in a top-down view (i.e., from above the head of a person wearing the EEG headset).

In this embodiment, the EEG headset 2500 comprises a frame 2510, an interface 2520, and a plurality of electrodes 2530. The frame comprises side rails 2511 configured to rest horizontally along the side of the person's head just above the ears, a rear rail 2522 configured to rest horizontally along the back of the person's head, a top rail 2513 configured to rest horizontally along the top of the person's head, and a forehead extension 2514. The electrodes 2530 in this embodiment are all circular electrodes as shown at ref 2533, but some are shown in oblique perspective 2532 or side perspective 2531 as they progress down the sides of the person's head from the top. The electrodes are configured to be lightly pressed against the person's head while in use, ideally as close to the person's scalp as possible to maximize signal capture. Electrical signals from brain activity received by electrodes are small and will typically be in the 1 microvolt (1 µV) to 10 microvolt (10 µV) range. The electrodes are shown in this diagram in the International 10-20 placement system which is the standardized EEG electrode placement of the International Federation of Clinical Neurophysiology (IFCN). Other electrode placement patterns are possible. Many other arrangements, configurations, materials of the EEG headset are possible, including frameless and controller-less configurations, configurations in which the frame is mesh-based, net-based or strap-based, frameless configurations in which the electrodes are held in place on the head using an adhesive, so long as, when in use, at least one electrode is held on or near the scalp of the person using the EEG headset such that electrical activity in the person's brain underneath the scalp can be received by the electrode and stored or transmitted. In some configurations, the storage and transmission may occur to a computing device on or within the EEG headset, itself.

The interface 2520 is electrically connected to the electrodes, and provides a means for transmission of the electrical signals from the electrodes to other devices. The interface may have a case 2521 containing electronics or may be fully integrated into the frame 2510 of the EEG headset 2500. The interface may contain electronics that receive and convert the signals before transmission (e.g., analog to digital conversion) or may simply pass through the raw electrical signals. The interface may transmit electrical signals via a wired connection 2522 or via a wireless transmitter (not shown).

Figure 26:
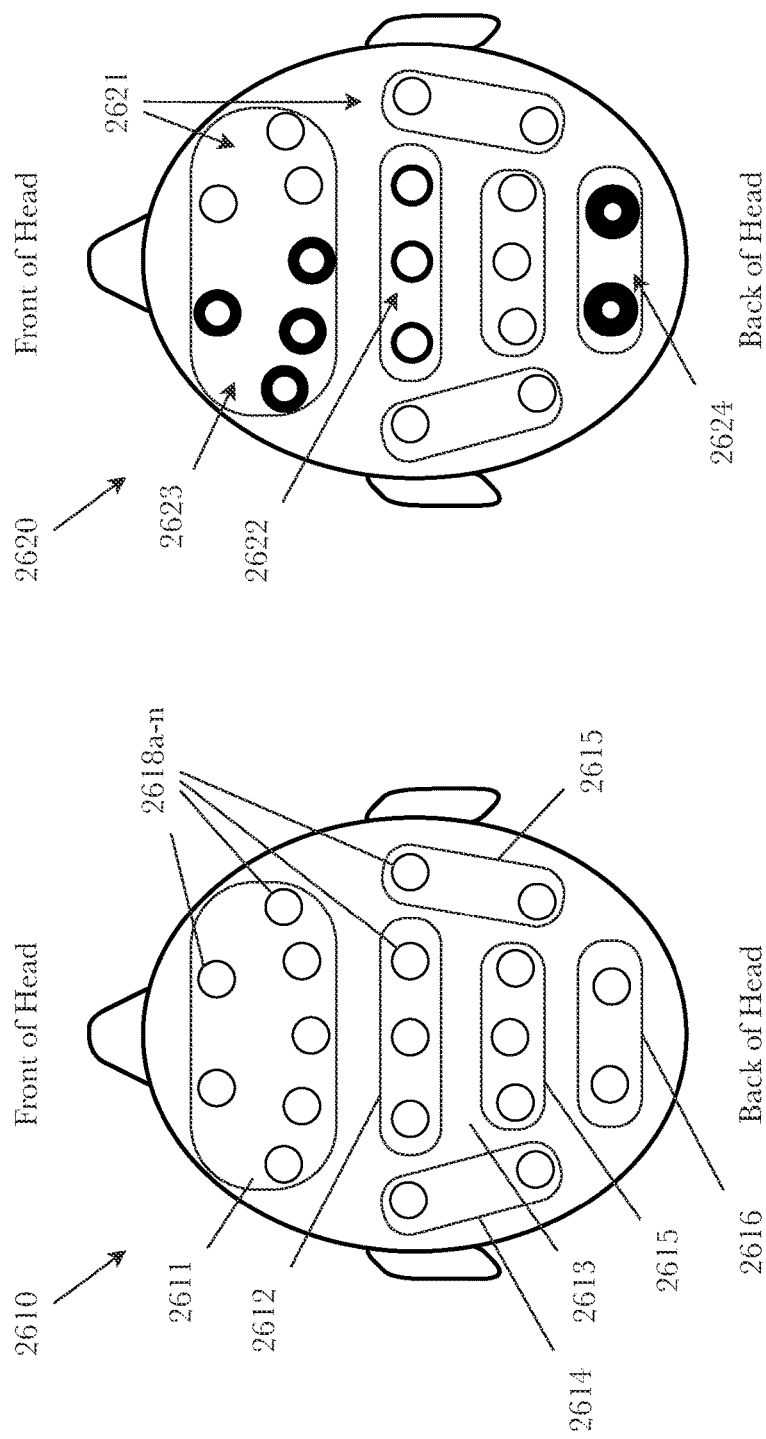
FIG. 26 is an exemplary illustration electroencephalograph sensor placement and data patterns of an electroencephalograph headset for use in thought-based control of sexual stimulation devices.

FIG. 26 is an exemplary illustration electroencephalograph sensor placement and data patterns of an electroencephalograph headset for use in thought-based control of sexual stimulation devices. The electrodes are shown in this diagram in the International 10-20 placement system which is the standardized EEG electrode placement of the International Federation of Clinical Neurophysiology (IFCN). Other electrode placement patterns are possible. Here, the sensors are also shown grouped into functional areas of the brain including the frontal lobe area associated with reasoning, speech, emotions, and problem-solving 2611, mid-brain areas associated with sensorimotor functions 2612 and attention, perception, and processing of sense stimuli 2613, lower brain areas associated with memory and auditory functions 2614, 2615, and rear brain areas associated with visual functions 2616.

The lefthand drawing 2610 shows the orientation of the user's head with electrodes 2618*a-n* placed according to the International 10-20 placement system within the various functional areas 2611-2616. The righthand drawing 2620 shows the same orientation and electrode placement, but illustrates a possible spatial EEG pattern of electrical activity in the user's brain. The darker borders of the electrodes show increased levels of activity in certain areas of the brain such as areas where there is little or no electrical activity 2621, areas where there is low electrical activity 2622, areas where there is a moderate level of electrical activity 2623, and areas where there is a high level of electrical activity 2624. These spatial EEG patterns may be associated with task objectives such as increasing or decreasing the speed or intensity of a controller for a stimulation device. Temporal EEG patterns (i.e., changes in one or more electrodes over time) may also be associated with task objectives.

Figure 27:
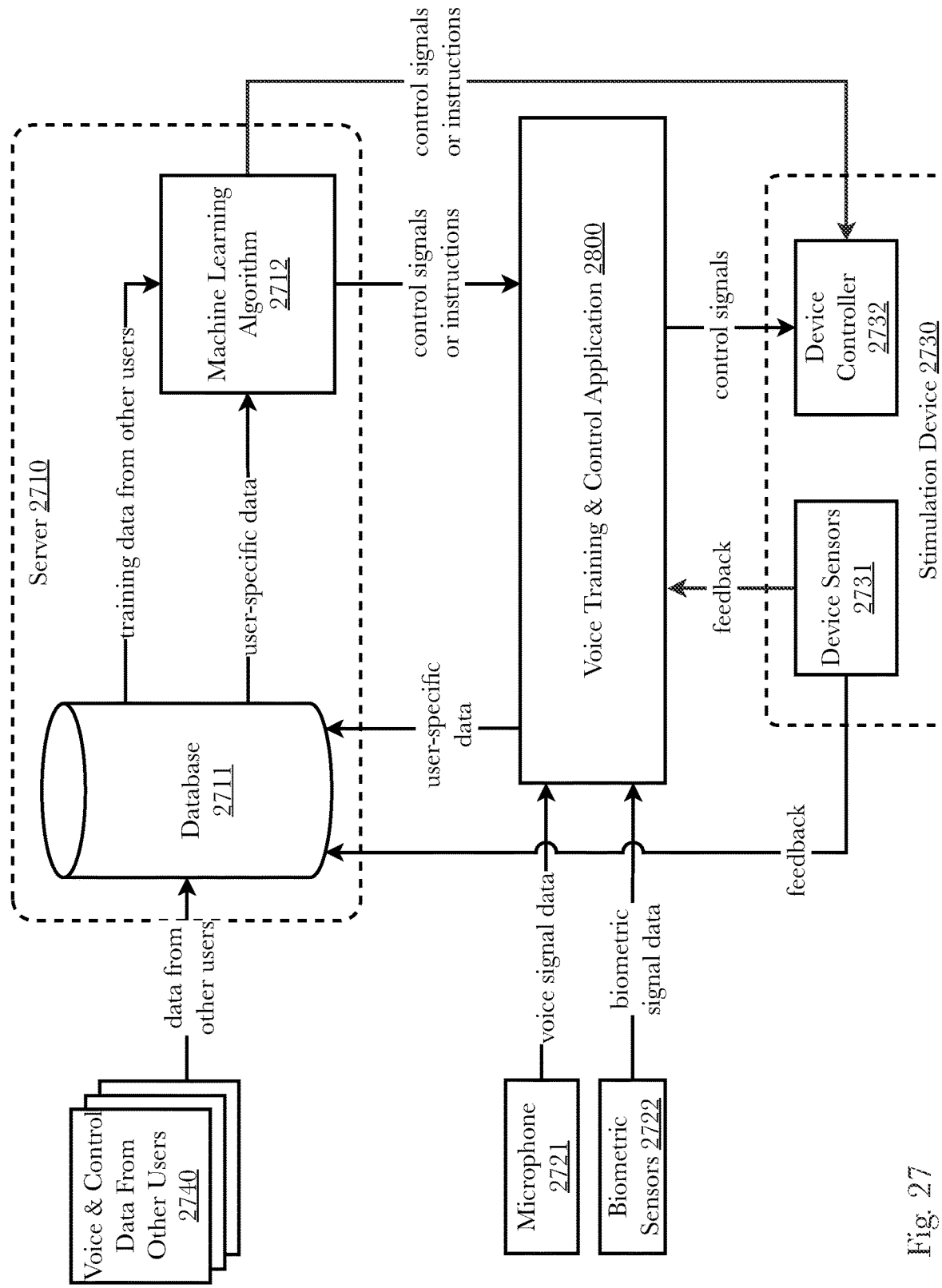
FIG. 27 is an exemplary system architecture diagram for a system for voice-based control of sexual stimulation devices.

FIG. 27 is an exemplary system architecture diagram for a system for voice-based control of sexual stimulation devices. In this embodiment, system comprises a server 2710, a voice training and control application 2800, a microphone 2721, one or more other biometric sensors, a stimulation device 2730, and data from other users and voice devices 2740.

Server 2710 may be a network-connected, cloud-based, or local server 2710, and comprises a database 2711 for storage of user data comprising voice patterns and control setting associations 2711, and a machine learning algorithm 2712 for analysis of data stored in database 2711 for generation of voice-based control signals or instructions. Machine learning algorithm 2712 is trained on data to identify patterns within usage data wherein certain voice patterns are correlated with stimulation device controls and/or biometric sensor data. User data may further contain user profiles comprising personal information about the user such as age, sex, height, weight, and fitness level; sexual preferences such as straight, gay, bi-sexual, etc.; stimulation preferences such as stimulation tempo/speed, stimulation intensity, location of stimulation, patterns of stimulation; and feedback information such as user ratings, other biometric sensor data such as heartrate data from sensors, moisture data from sensors, etc.; all of which may be incorporated by machine learning algorithm 2712 to better correlate voice patterns with stimulation device controls for specific users. After training, when a voice pattern from microphone 2721 is input into machine learning algorithm 2712, machine learning algorithm 2712 generates one or more control signals or instructions for stimulation device 2730 based on associations between voice patterns and control settings learned by machine learning algorithm 2712 during training. The machine learning algorithm 2712 may periodically or continuously be re-trained based on new data from voice training and control application 2800 (such as, but not limited to, new training data acquired as a result of additional voice training by user) and data from other users and voice devices 2740 being similarly stored and processed. It should be noted that, while a machine learning algorithm is used in embodiment, system is not necessarily limited to use of machine learning algorithms and other processes for analysis of data may be used, including but not limited to modeling and statistical calculations. For example, in some embodiments, the machine learning aspect may be bypassed altogether, having system rely only on associations of voice patterns/speech recognition with control signals and/or recognitions by voice training & control application 2800. In other embodiments, a two-stage training algorithm may be used wherein machine learning algorithm 2721 is first trained generically on a large number of users, then re-trained for a particular user using user-specific training data. In some embodiments, control signals for stimulation device 2730 may be based on a combination of non-machine learning algorithm associations of voice patterns/speech recognition with control signals and machine learning algorithm associations of voice patterns/speech recognition with control signals.

The system of this embodiment further comprises a software based voice training and control application 2800 operating on a computing device which may be of any type including but not limited to a desktop computer, tablet, mobile phone, or even a cloud-based server accessible via a web browser. The voice training and control application 2800 acts as an interface between stimulation device 2730, machine learning algorithm 2712, microphone 2721 and other biometric sensors 2722, as well as operating to train system to make associations between voice patterns and control signals for a particular user or users. In its role as an interface, voice training and control application 2800 relays feedback from device to server 2710 and relays control signals (or translates instructions into control signals) to device controller 2732 of stimulation device 2730. Details regarding the architecture and operation of voice training and control application 2800 are further described below. Depending on configuration, voice training and control application 2800 may further act as a user interface for operation of, and/or changing settings of, stimulation device 2730. In its role as a voice training application for machine learning algorithm 2712, voice training and control application 2800 assigns training tasks to user, receives voice signal data from microphone 2721, and associates patterns of voice signal data with objectives of the training tasks (e.g., reduction in the speed or intensity of operation of stimulation device).

In this embodiment, microphone 2721 sends voice signal data to voice training & control application 2800. The user data may further comprise biometric signals data from other biometric sensors 2722. Voice signal data is a form of biometric data, but other biometric sensors 2722 may be used to provide biometric signal data that is not associated with voice signal data, such as external or third-party heartrate monitors that provide heartrate data.

Voice training and control application 2800 provides user-specific data comprising voice patterns/recognized speech, or control associations, or both to server 2710 and requests control signals (or instructions for control signals) for stimulation device 2730 based on user-specific data. During training of machine learning algorithm 2712, voice patterns/recognized speech and control associations are used as a form of labeled training data to train or re-train machine learning algorithm 2712. After training, voice patterns/recognized speech may be processed through trained machine learning algorithm 2712, which provides control signals or instructions back to voice training and control application for operation of stimulation device 2730. In some embodiments, voice patterns/recognized speech are sent to machine learning algorithm 2712 and processed into control signals in real time or near real time. In some embodiments, control signals or instructions may be sent directly from machine learning algorithm 2712 directly to device controller 2732 of stimulation device 2730. Voice training and control application 2800 may be configured to periodically or continuously send updated user-specific data to server 2710 for processing by machine learning algorithm 2712 to generate modified or updated control signals or instructions, thus changing and evolving the automated operation of device based on changed or updated information from device sensors 2731, voice training and control application 2800, or updating/retraining of machine learning algorithm 2712 based on user's data and data from other users and voice devices 2740 being similarly stored and processed.

In some embodiments, voice training and control application 2800 may exist as an application on a user's mobile phone, and may interface with stimulation device 2730 via a local network (e.g., WiFi, Bluetooth, etc.). In other embodiments, voice training and control application 2800 may exist as an application on server 2800 accessible via a user account also residing on server. In other embodiments, certain components of server 2710 and voice training and control application 2800 may reside on tablet computer or other mobile device, or on stimulation device 2730 itself (e.g., a copy of trained machine learning algorithm 2712 could reside on a smartphone such that automated generation of control signals can be accomplished without access to server). In some embodiments, voice training and control application 2800 and/or server components will be integrated into stimulation device 2730 (e.g., stored in a memory and operable on device controller 2732) instead of residing on a separate computing device.

Stimulation device 2730 may be any device configured to provide sexual stimulation by any variety of means, including but not limited to, linear stroking, vibration, rotation, heat, electrical stimulation, or combinations of the above. Device sensors 2731 may be any sensor on device capable of providing data regarding an aspect of sexual arousal, including but not limited to, heartrate sensors, moisture sensors, tumescence sensors, pressure sensors, strain gauges, and length/distance sensors. Further, device sensors 2731 include devices capable of receiving sensor data from external sensors (e.g., wearable fitness devices that record heart rates) via WiFi, Bluetooth, or other networking technologies. Device controller 2732 is a device capable of operating stimulation device based on control signals received. Device controller 2732 may be a simple power relay switching device that receives low-powered signals and outputs corresponding power to motors, vibrators, etc., or may be a computing device with a memory, processor, and storage. In the latter case, device controller 2732 may be configured to receive instructions to generate control signals and generate control signals, itself. Further, in some embodiments, aspects of voice training and control application and/or machine learning algorithm 2712 may be incorporated into device controller 2732.

Figure 28:
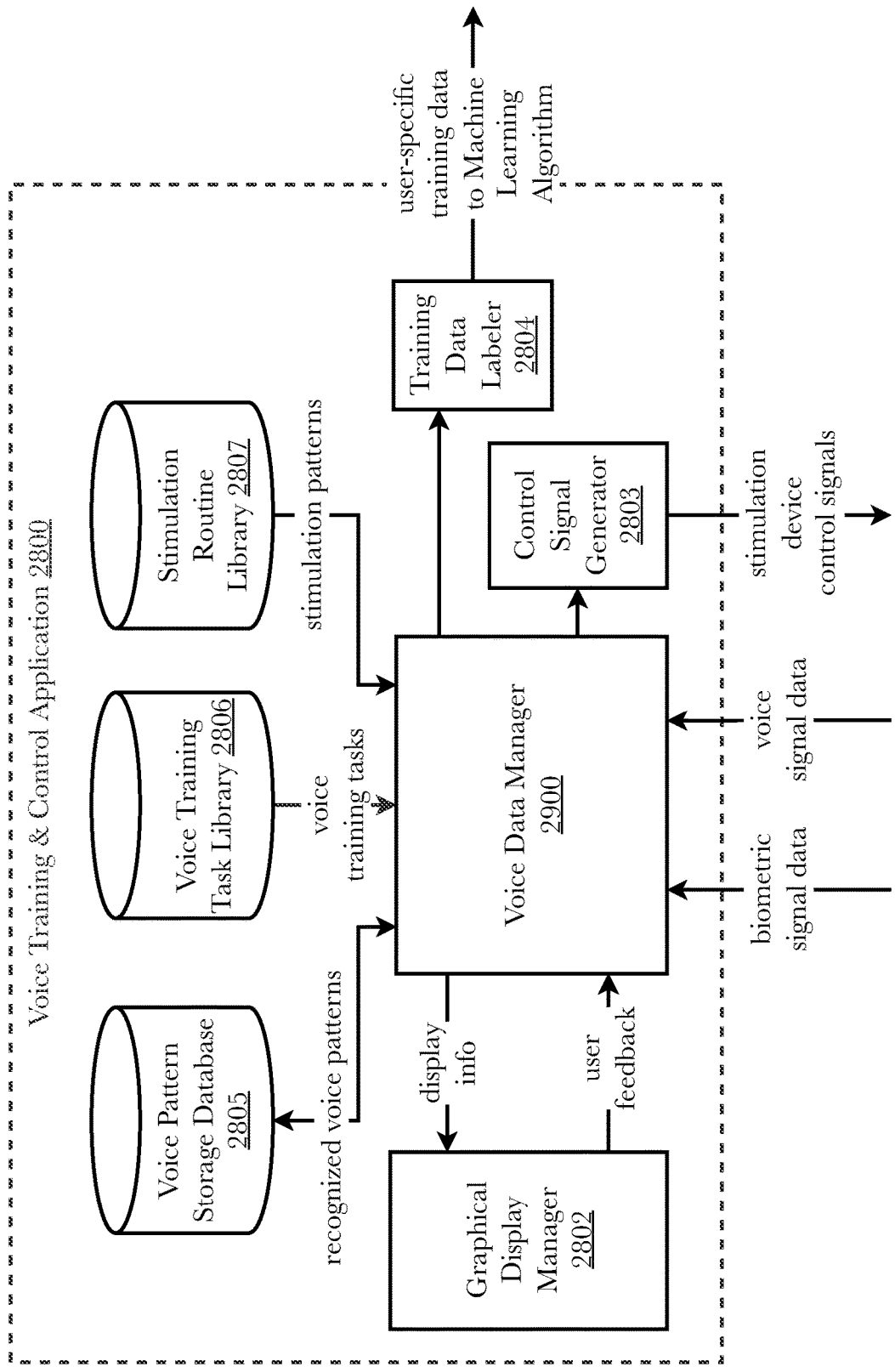
FIG. 28 is an exemplary system architecture diagram for a voice training and control application aspect of a system for voice-based control of sexual stimulation devices.

FIG. 28 is an exemplary system architecture diagram for a voice training and control application aspect of a system for voice-based control of sexual stimulation devices. In this embodiment, voice training and control application 2800 is a software application operating on a computing device, which may be of any type including but not limited to a desktop computer, tablet, mobile phone, or even a cloud-based server accessible via a web browser. Voice training and control application 2800 acts as an interface between stimulation device 2730, machine learning algorithm 2712, and microphone 2721 and other biometric sensors 2722, as well as operating to train system to make associations between voice patterns/recognized speech and control signals for a particular user or users. In its role as an interface, voice training and control application 2800 relays feedback from device to server 2710 and relays control signals (or translates instructions into control signals) to device controller 2732 of stimulation device 2730. Details regarding the architecture and operation of voice training and control application 2800 are further described below. Depending on configuration, voice training and control application 2800 may further act as a user interface for operation of, and/or changing settings of, stimulation device 2730. In its role as a voice training application for machine learning algorithm 2712, voice training and control application 2800 assigns training tasks to user, receives voice signal data from microphone 2721, and associates patterns of voice signal data with objectives of the training tasks (e.g., reduction in the speed or intensity of operation of stimulation device). Voice training and control application 2800 of this embodiment comprises a voice data manager 2900, a graphical display manager 2802, a control signal generator 2803, a training data labeler 2804, and three databases, a voice pattern storage database 2805, a voice training task library 2806, and a stimulation routine library 2807.

Depending on its configuration, voice data manager 2900 is responsible for generation of labeled training data to machine learning algorithm 2712 for supervised learning, pass-through of voice signal data to machine learning algorithm 2712 for unsupervised learning, receipt of control signals from trained machine learning algorithm 2712 based on pass-through of voice signal data, or generating control signals by direct association of voice patterns/recognized speech with objectives corresponding to device controls, or any combination of above. In this embodiment, it is assumed that voice data manager 2900 is configured to generate voice pattern (or recognized speech)/objective pairs either to directly generate control signals itself, or to pass those voice pattern (or recognized speech)/objective pairs to machine learning algorithm 2712 for training. In other configurations, however, voice data manager 2900 may pass through voice signal data to machine learning algorithm 2712 for unsupervised learning in which machine learning algorithm 2712 identifies voice patterns (or recognized speech) and makes associations with objectives. In cases involving complex and/or voluminous data such as detecting patterns in voice signal data, unsupervised learning is often useful in that it can find hidden or difficult-to-identify patterns in data that might otherwise be missed.

Voice data manager 2900 retrieves and implements voice training tasks from voice training task library 2806. Training tasks comprise a stimulus such as auditory, visual cues, or sexual stimulation, an objective such as slowing down or speeding up stimulation, and instructions for user to attempt to achieve objective using a voice command or non-speech vocalization. For example, a training task may involve displaying a task on a visual display using graphical display manager, wherein display asks user to say the word "faster" (representing increased speed or intensity of some aspect of stimulation device) or "slower" (representing decreased speed or intensity of some aspect of stimulation device). While user is performing a task, microphone 2721 detects speech and/or non-speech vocalizations of user and forwards them as voice signal data to voice data manager 2900. The voice data manager 2900 receives voice signal data from microphone 2721 and detects speech or identifies a pattern of voice activity from voice signal data. The pattern of voice activity (aka a voice pattern) may be a frequency pattern, an amplitude pattern, some combination of the two, or some derivative of either or the combination (e.g., a pattern discovered by passing the voice signal data through a filter, algorithm, or function such as a Kalman filter or a Fourier transform). The voice data manager 2900 associates voice pattern (or recognized speech) with an objective of task (e.g., reducing the speed of stimulation), creating voice pattern (or recognized speech)/objective pairs that can be used either to generate controls for stimulation device via a control signal generator 2803 or as labeled training data via a training data labeler 2804. The voice pattern (or recognized speech)/objective pairs may be stored in voice pattern storage database 2805. In some embodiments, new voice pattern (or recognized speech)/objective pairs may be compared with stored voice pattern (or recognized speech)/objective pairs to confirm, reject, or modify associations.

In some embodiments, stimulus for some voice training tasks may comprise stimulation via stimulation device as a supplement to auditory or visual tasks, or as an alternative thereto. The voice data manager 2900 may select one or more stimulation routines from a stimulation routine library 2807, apply stimulation to user via stimulation device 2730, and receive non-speech vocalizations related to stimulation from the microphone. For example, voice data manager 2900 may initiate stimulation at a low speed or intensity. Infrequent or low-amplitude non-speech vocalizations may be associated with the low speed or intensity, and higher-amplitude non-speech vocalizations may be associated with a desire to increase speed or intensity. Similarly to voice training for speech, voice data manager 2900 associates voice patterns of non-speech vocalizations with an objective of stimulation (e.g., increasing speed or intensity of stimulation), creating voice pattern/objective pairs that can be used either to generate controls for stimulation device via a control signal generator 2803 or as labeled training data via a training data labeler 2804. The voice pattern/objective pairs may be stored in voice pattern storage database 2805. In some embodiments, new voice pattern/objective pairs may be compared with stored voice pattern/objective pairs to confirm, reject, or modify associations.

In some embodiments, associations may further incorporate biometric signal data from other biometric sensors 2722, creating more complex associations which may be stored as tables, high dimensional vectors, graphs, or other forms of complex relationship storage. In some cases, user may provide additional user feedback via graphical display manager 2802 by interacting with display. Such user feedback may be, for example, indicating a level of concentration user was able to apply, a mood of user, or a tiredness level of user, which user feedback may be used as additional association information.

The more complex association data between voice patterns, tasks, feedback, and stimulation routines, more useful machine learning algorithm 2712 is in determining relationships between input data (e.g., voice signals, biometric signals, user feedback) and intended outputs (i.e., control of some aspect of stimulation device).

Figure 29:
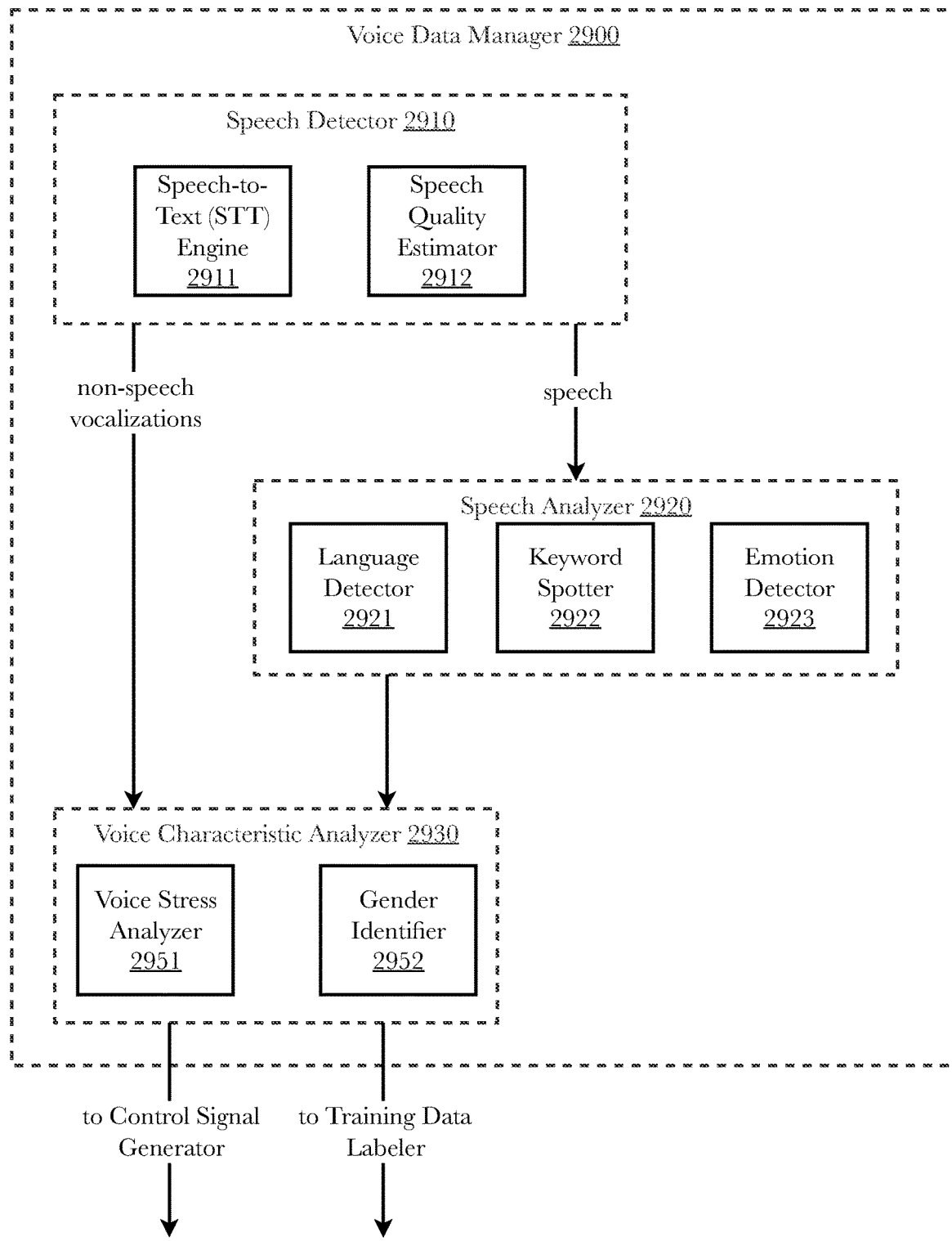
FIG. 29 is an exemplary system architecture diagram for a voice data manager aspect of a system for voice-based control of sexual stimulation devices.

FIG. 29 is an exemplary system architecture diagram for a voice data manager aspect of a system for voice-based control of sexual stimulation devices. Voice data manager 2900 is responsible for detecting and analyzing speech and for analyzing voice characteristics of vocalizations (whether speech or non-speech). In this embodiment, voice data manager 2900 comprises a speech detector 2910, a speech analyzer 2920, and a voice characteristic analyzer 2930.

Speech detector 2910 comprises a speech-to-text engine 2911 and a speech quality estimator 2912. Speech-to-text engine 2911 receives audio (i.e., acoustic sound waves, or sounds, typically from a human voice and comprising speech) from microphone 2721, detects speech within the audio, and transcribes it to text. Speech quality estimator 2912 determines the quality of the detected speech for use by the speech analyzer 2920. Non-speech vocalizations (e.g., sighs, grunts, etc.) within the audio do not contain recognizable speech, and are sent directly to the voice characteristic analyzer 2930. The speech quality estimate may determine the quality of the detected speech using audio quality metrics (e.g., total harmonic distortion, signal to noise ratio, output power, frequency response, etc.) or speech characteristics (e.g., percentage of words recognized, number of unrecognizable words, etc.). Speech quality estimates may determine, for example, whether the detected speech is of sufficient quality to be processed by language detector 2921. Speech-to-text engine 2911 may use a machine learning algorithm to perform speech-to-text detection and transcription.

Speech analyzer 2920 uses the text and quality estimates from speech detector 2910 to identify control commands, expressions related to control commands, and/or emotions that may be relevant to control commands. Speech analyzer comprises a language detector 2921, a keyword spotter 2922, and an emotion detector 2923. Language detector 2921 may process text to identify a language (e.g., matching words and phrases of the text to a database of words and phrases from a plurality of languages to detect which language is being used in the text) or may process audio to identify acoustic characteristics in the audio that match the acoustic characteristics of certain languages. Language detector 2921 may use a machine learning algorithm to perform the matching and detection. Once a language has been detected, keyword spotter 2922 compares the words in the text against a database of keywords for that language to identify either control commands (e.g., "turn vibration down") or speech related to control commands (e.g., "slower"). Emotion detector 2923 analyzes words and phrases in the text (e.g., "that feels good") to determine emotions (e.g., happiness, satisfaction, dissatisfaction, etc.) that may be expressed by the text that are not necessarily control commands, but have some relevance to a control command. Emotion detector 2923 may use a machine learning algorithm to perform emotion detection.

Voice characteristic analyzer 2930 receives audio comprising non-speech vocalizations and the audio of detected speech for purposes of analyzing the voice characteristics of the audio. Voice characteristic analyzer 2930 comprises a voice stress analyzer 2951 and a gender identifier 2952. Voice stress analyzer 2951 analyzes the audio characteristics (pitch, tone, timbre, loudness, etc.) of the vocalizations to determine whether some emotion is being experienced by the person uttering the vocalization. The tonal quality and speech patterns of the human voice change when experiencing emotional situations, whether good or bad. For example, people tend to talk in loud voices when angry and to use shrill or high-pitched voices when feeling scared or panicky. People tend to speak more rapidly when they get excited or nervous, and more slowly and contemplatively when they are calm or being contemplative. Voice stress analyzer 2951 uses these audio characteristics to detect stress (good or bad) in a person's voice. Voice stress analyzer 2951 may use comparative analyses (e.g., comparisons with a database of audio characteristics indicating stress) or may use a machine learning algorithm to perform voice stress analysis. Voice stress can be used to generate control signals. For example, voice stresses indicating excitement or happiness can be used to increase the intensity of stimulation, and voice stresses indicating pain or discomfort can be used to create the intensity of stimulation.

Gender identifier 2952 may be used to identify the gender of the speaker. Men's voices are typically lower in pitch than women's voices. Gender identification may help in the voice stress analysis (e.g., to determine whether the high-pitched voices are elevated male voices or normal female voices) and/or to generate control signals (e.g., in a device with multiple stimulation functions wherein certain stimulation functions are intended for male stimulation and certain functions are intended for female stimulation).

FIG. 30 is an exemplary algorithm for voice data capture and machine learning algorithm training for voice-based control of sexual stimulation devices. This exemplary algorithm comprises three stages, training on curated data 3010, capture of, and training on, user-specific data using voice tasks 3020, and capture of, and training on, user-specific data using stimulation tasks 3030. While in this exemplary algorithm stages are shown as sequential, in some embodiments these and other stages or training could be used individually or in other combinations.

Stage 1 of this embodiment comprises training machine learning algorithm generically (i.e., for a typical, unspecified user) using pre-labeled data from other users 3011 who have performed voice training tasks. This pre-labeled training data does not necessarily have to be in field of control of sexual stimulation devices, and may be pre-labeled training data from control of other devices or performance of other tasks (e.g., biofeedback relaxation routines, mediation, etc.), as long as there is some association in pre-labeled data between voice patterns (or recognized speech) and some objective that could be translated or applied to control of devices.

Stage 2 of this embodiment comprises user-specific voice training using visual tasks 3020. A visual voice training task is selected and displayed on a display of a computing device 3021. The training task comprises visual cues with instructions for user to speak commands and/or make non-speech vocalizations associated with certain intended operation of the device (e.g., speeding up and/or slowing down stimulation). While user is performing the task, a microphone 2721 detects the speech and/or non-speech vocalizations of user and forwards them as voice signal data, which is received and recorded 3027. The visual display is updated with progress of user in accomplishing task (for example, where user's voice patterns and/or recognized speech match expected voice patterns and/or recognized speech stored in voice pattern storage database 2800 or simply updated with a notification of progress (e.g., a notification that a command was recognized) 3028. The voice patterns and/or recognized speech are associated with task objective 3030. The pattern of voice activity (aka a voice pattern) may be a frequency pattern, an amplitude pattern, some combination of the two, or some derivative of either or the combination (e.g., a pattern discovered by passing the voice signal data through a filter, algorithm, or function such as a Kalman filter or a Fourier transform). Voice data manager 2801 associates voice pattern (or recognized speech) with an objective of task (e.g., reducing the speed of stimulation), creating voice pattern (or recognized speech)/objective pairs that can be used either to generate controls for stimulation device via a control signal generator 2803 or as labeled training data via a training data labeler 2804. The voice pattern (or recognized speech)/objective pairs may be stored in voice pattern storage database 2805. In some embodiments, new voice pattern (or recognized speech)/objective pairs may be compared with stored voice pattern (or recognized speech)/objective pairs to confirm, reject, or modify associations. The process may be repeated until a desired quantity of data is obtained.

Stage 3 of this embodiment comprises user-specific voice training using stimulation tasks 3030, comprising stimulation via stimulation device. A stimulation routine is selected from a stimulation routine library 2807, applied to user via stimulation device 2730, and the user is asked to make a mental association with the stimulation (e.g., picturing an image in the mind, thinking about a feeling associated with the stimulation, etc.) 3031. Non-speech vocalizations related to stimulation may be received from microphone and recorded 3032. Additional biometric data and/or user feedback may be received and recorded 3033. Machine learning algorithm them associates patters of voice signal data with the stimulation, biometric signal data, and/or user feedback 3034. For example, voice data manager 2801 may initiate stimulation at a low speed or intensity. Infrequent or low-amplitude non-speech vocalizations may be associated with the low speed or intensity, and higher-amplitude non-speech vocalizations may be associated with a desire to increase speed or intensity. Similarly to voice training for visual tasks, voice pattern or patterns are associated with an objective of stimulation (e.g., increasing speed or intensity of stimulation), creating voice pattern/objective pairs that can be used either to generate controls for stimulation device 3025 or as labeled training data for use in training a machine learning algorithm 3040. The voice pattern (or recognized speech)/objective pairs may be stored in voice pattern storage database 2805. In some embodiments, new voice pattern (or recognized speech)/objective pairs may be compared with stored voice pattern (or recognized speech)/objective pairs to confirm, reject, or modify associations. The process may be repeated until a desired quantity of data is obtained.

The more complex association data between voice patterns, tasks, feedback, and stimulation routines, more useful machine learning algorithm 2712 is in determining relationships between input data (e.g., voice signals, biometric signals, user feedback) and the intended outputs (i.e., control of some aspect of stimulation device).

FIG. 31 shows an exemplary use of a mobile computing device as a biofeedback-based controller for sexual stimulation devices. The use of a mobile computing device 3102 with standard sensors (i.e., not sensors specially designed for collection of biofeedback data) can be advantageous as no specialized hardware is required for control of sexual stimulation devices. In this embodiment, controller is a mobile computing device 3102 such as a smartphone comprising a forward-facing camera 3110, a rearward-facing camera 3111, a light source 3112, and a fingertip sensor 3113. In some embodiments, mobile computing device 3102 may further comprise a motion sensor (e.g., an inertial measurement unit (IMU)) 3103 configured to detect motions of mobile computing device 3102 in three dimensions. This allows for control of sexual devices through natural hand and/or body movements by gripping mobile computing device 3102 and moving it in three dimensional space or by placing mobile computing device 3102 on the body (e.g., on the hips to detect thrusting motions). In some embodiments, mobile computing device 3102 may further comprise a microphone for processing of voice-based controls as described above.

Forward-facing camera 3110 may be used in conjunction with facial recognition software to confirm the identity of the user for security purposes and/or to detect facial expressions of the user as a form of biometric data. Expressions of pleasure (e.g., smiling) or discomfort (e.g., wincing) can be used to adjust the operation of the sexual stimulation device. The system architectures and algorithms described above in relation to thought-based controls using electroencephalographs (FIGS. 22-24 and their associated text) and voice-based controls using microphones (FIGS. 27-31 and their associated text) are equally applicable to generation of control signals using facial expressions with the substitution of facial image data for the EEG or voice data.

Rearward-facing camera 3111 may be combined with light source 3112 to form an optical heart rate sensor. Light source 3112, which in most mobile computing devices 3102 is a light emitting diode (LED), emits a bright light of a known wavelength and is typically placed near rearward-facing camera 3111. Placement of a fingertip across both light source 3112 and rearward-facing camera 3111 causes light of the known wavelength to pass into the fingertip, and a portion of the light to pass through the fingertip to rearward-facing camera 3111. Light passing through the fingertip will change in intensity and wavelength as blood is pumped through the capillaries in the fingertip. Rearward-facing camera 3111 can detect these changes, and a software application mobile computing device 3102 can be programmed to detect the user's heart rate based on the timing and intensity of these changes. In this way, mobile computing device 3102 can be used without specialized hardware as a heart rate monitor to provide biometric data for control of sexual stimulation devices.

Fingertip sensor 3113 may be of several types such as fingerprint detector or galvanic skin response. Many mobile computing devices currently have fingerprint detectors built in, and such devices can provide biometric data to confirm the identity of the user of the device. However, fingertip sensor 3113 could comprise electrodes that allow for measurement of galvanic skin response. While this would require specialized hardware, galvanic skin response is a way to measure emotional and/or physical reactions to stimuli through changes in perspiration. Thus, where fingertip sensor 3113 is a galvanic skin response sensor, responses to stimulation can be measured as changes in perspiration and control signals can be generated, accordingly.

Microphones 3114 are standard equipment on mobile computing devices 3102 and can be used to process voice-based controls as described above (FIGS. 27-31 and their associated text).

In embodiments further comprising a motion sensor 3103, data from motion sensor 3103 may be used to supplement biofeedback data. For example, where mobile computing device 3103 is placed on the hips, hip thrusts and other movements may be used to coordinate stimulation timing with the hip thrusts as an addition to control of stimulation intensity or other stimulation aspects using biofeedback data. As another example, where mobile computing device 3102 is placed on the chest while the users is lying down, movement of the mobile computing device can be used to detect breathing as the chest expands and contracts. Mobile computing device 3102 with its integrated IMU 3103 is configured to detect motions of mobile computing device 3102 in three dimensions, including linear movements 3105 along longitudinal axis 3108 of mobile computing device 3102, tilting motions 3106 away from longitudinal axis 3108 of mobile computing device 3102, and rotational movements 3107 about longitudinal axis 3108 of mobile computing device 3102. In this embodiment, mobile computing device has its own control system (not shown) capable of interfacing with IMU. Inertial measurement units (IMU) are collections of "sensors on a chip" containing built-in accelerometers, gyroscopes, and magnetic field sensors, plus a interfaces for receiving power and interfacing with microcontrollers. Each of sensors are typically three-axis sensors capable of detection of movement with six degrees of freedom (i.e., linear movements in x, y, and z planes, and rotational movement about x, y, and z axes). IMUS are often described as having three axes of detection per sensor (e.g., three axes of detection if just an accelerometer is used, six axes of detection if both an accelerometer and gyroscope are used, etc.). Thus, mobile computing device 3102 is capable of detecting three dimensional motions in any of six possible degrees of freedom.

FIG. 32 shows an exemplary use of a smartwatch or fitness tracker as a biofeedback-based controller for sexual stimulation devices. In this embodiment, controller is a wearable device 3202 such as a smartwatch or fitness tracker comprising an optical heart rate sensor 3214 comprising a light source 3215 and a light detector 3214, and a strap or other means for attaching device to a person or clothing 3204.

In some embodiments, mobile computing device 3102 may further comprise a motion sensor (e.g., an inertial measurement unit (IMU)) 3203, and configured to detect motions of wearable device 3202 in three dimensions. This allows for control of sexual devices through natural hand movements by gripping wearable device 3202 and moving it in three dimensional space or through natural body movements by moving portion of body or clothing to which wearable device 3102 is attached.

In smartwatches and fitness trackers, light source 3215 is combined with light detector 3214 to form an optical heart rate sensor 3214. Light source 3215 in fitness trackers is typically one or more a light emitting diodes (LEDs) that emit a bright light of a known wavelength. Light detector 3216 is a light-sensitive device such as a camera or light-dependent resistor (also known as a photoresistor). In this embodiment, light source 3215 is a plurality of LEDs arranged in a ring around light detector 3216. Attachment of wearable device 3202 on the wrist of a user places both light source 3215 and light detector 3214 in contact with the skin of the user, and causes light of the known wavelength to pass into the skin, and a portion of the light to pass through the skin to light detector 3216. Light passing through the skin will change in intensity and wavelength as blood is pumped through the capillaries in the skin. Light detector 3216 can detect these changes, and a software application in wearable device 3202 can be programmed to detect the user's heart rate based on the timing and intensity of these changes. In this way, wearable device 3202 can be used as a heart rate monitor to provide biometric data for control of sexual stimulation devices.

In embodiments further comprising a motion sensor 3203, data from motion sensor 3203 may be used to supplement biofeedback data. For example, where wearable device 3202 is placed on or against the hips, hip thrusts and other movements may be used to coordinate stimulation timing with the hip thrusts as an addition to control of stimulation intensity or other stimulation aspects using biofeedback data. As another example, where wearable device 3202 is placed on or against the chest while the user is lying down, movement of the mobile computing device can be used to detect breathing as the chest expands and contracts. Wearable device 3202 with its integrated IMU 3103 is configured to detect motions of wearable device 3202 in three dimensions, including linear movements 3205 along longitudinal axis 3208 of wearable device 3202, tilting motions 3206 away from longitudinal axis 3208 of wearable device 3202, and rotational movements 3207 about longitudinal axis 3208 of wearable device 3202. In this embodiment, mobile computing device has its own control system (not shown) capable of interfacing with IMU. Inertial measurement units (IMU) are collections of "sensors on a chip" containing built-in accelerometers, gyroscopes, and magnetic field sensors, plus a interfaces for receiving power and interfacing with microcontrollers. Each of sensors are typically three-axis sensors capable of detection of movement with six degrees of freedom (i.e., linear movements in x, y, and z planes, and rotational movement about x, y, and z axes). IMUS are often described as having three axes of detection per sensor (e.g., three axes of detection if just an accelerometer is used, six axes of detection if both an accelerometer and gyroscope are used, etc.). Thus, wearable device 3202 is capable of detecting three dimensional motions in any of six possible degrees of freedom.

FIG. 33 and FIG. 34 show exemplary integrations of a penile tumescence sensor into a gripper for use as a biometric feedback device. In this embodiment, the biometric feedback sensor is internal to the stimulation device, in contract to the previously-described external biometric feedback sensors. FIG. 33 shows a top-down view 3300 of a tube-shaped or ring-shaped gripper 108 with one or more pressure sensors 3301 affixed to the interior surface of gripper 108, wherein pressure against the sensors by an inserted penis would indicate the level of penile tumescence, which corresponds to sexual arousal. FIG. 34 shows a top-down view 3400 of a tube-shaped or ring-shaped gripper 108 with a strain sensor (also known as a strain gauge) 3401 attached across an opening or gap 3402 in the tube or ring such that increased penile tumescence increases the size of gap 3402, thus putting increased strain on strain gauge 3401 as an measurement of penile tumescence. A plurality of gaps 3402 and/or strain gauges 3401 may be used. Other configurations are possible, and other biometric sensors may be used, either internally to the stimulation device or externally to the stimulation device.

Figure 35:
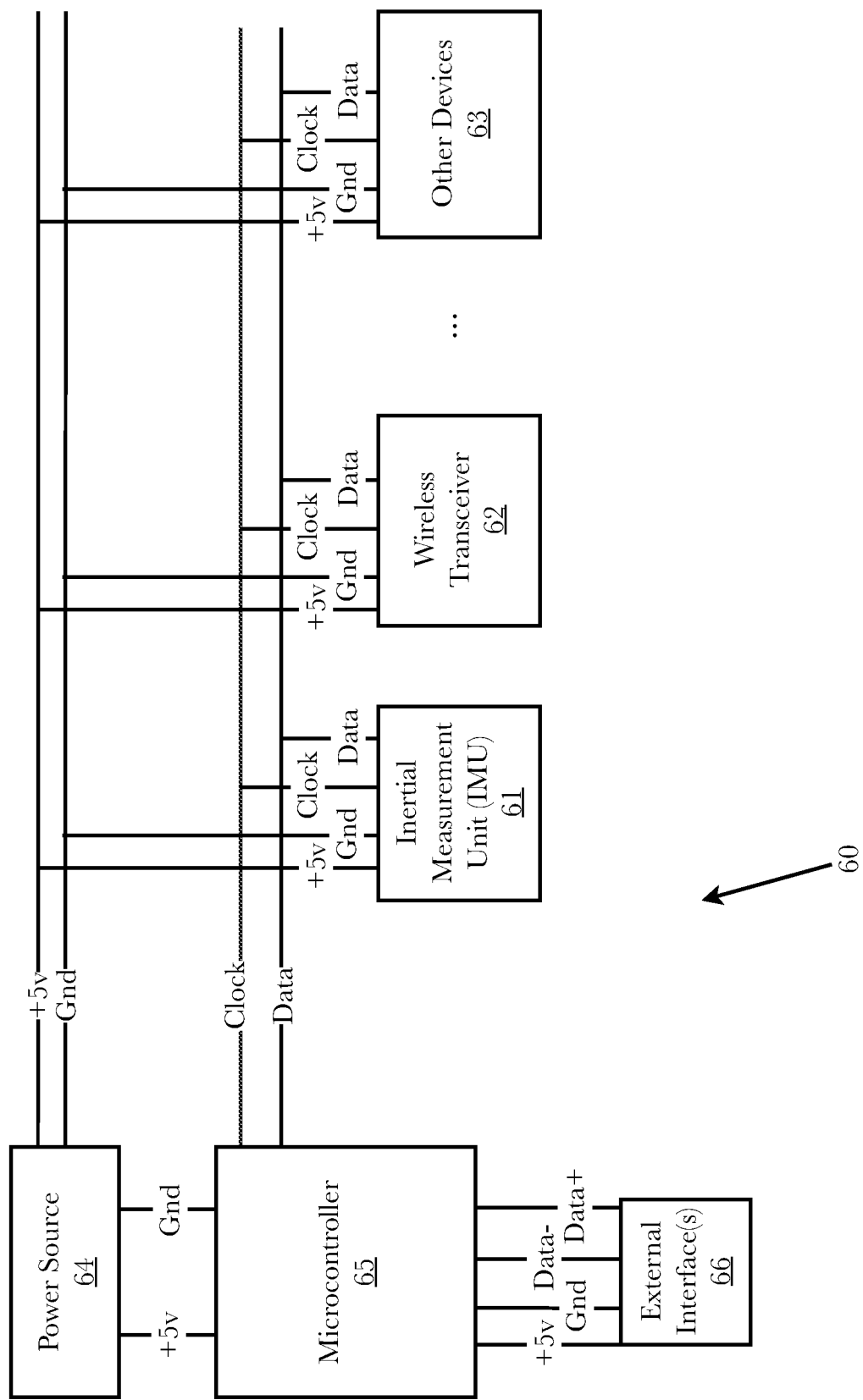
FIG. 35 is an exemplary system architecture diagram for a control system for a biofeedback-based controller for sexual stimulation devices.

FIG. 35 is an exemplary system architecture diagram for a control system for a biofeedback-based controller for sexual stimulation devices. Control system detects manipulation of controller through its sensors and outputs signals corresponding to manipulations either as control signals for a compatible sexual stimulation device or as motion data to be converted into control signals for a compatible sexual stimulation device. In this example, control system 60 comprises a power source 64, a microcontroller 65, an external interface 66, and one or more input/output devices 61-63. The core of control system is a microcontroller 65, which is a small computing device with one or more processors, a memory, communications controllers, and one or more inputs and outputs. Microcontrollers 65 in this type of application are typically pre-programmed for intended use. Microcontroller 65 may have onboard power and/or may be powered by an external power source 64. Microcontroller 65 is used to receive input signals either from sensors 63 or computing devices, such as receiving signals from an inertial measurement unit (IMU) 61. Microcontroller 65 of this example contains an inter-integrated circuit bus (also known as I2C) which allows for fully addressable serial communication with slave devices such as IMU 61, a wireless transceiver 62, or input/output devices 63 using common wires for +5 v and ground (for power), a clock signal, and data. While not required, input/output devices 61-63 may also contain a communications controller allowing for I2C serial communications with microcontroller 65. In this example, microcontroller 65 receives motion data from accelerometers, gyroscopes, magnetometers, and/or or motion sensors in IMU 61, translates motion data into control signals for a compatible sexual stimulation device, and transmits control signals to another compatible sexual stimulation device (or to another computing device for further transmission to compatible sexual stimulation device) via wireless transmitter 62.

Although this example uses I2C serial communications protocol, any addressable communication protocol may be used, including serial and parallel communications protocols, such as serial to peripheral interface (SPI), universal asynchronous receiver-transmitter (UART), etc. In some embodiments, direct pinouts from microcontroller 65 may be used instead of addressable communications protocols.

Operation of sexual stimulation device via motion sensing controller can be done locally based on a wired or wireless connection between controller and device, or remotely based on connection between the controller and device through a local area network (LAN), wide area network (WAN), or via the Internet. Thus, the user of the controller and the user of the device may be the same person or different persons, and if different persons, may be co-located or remote from one another. Further, in some embodiments, there may be either multiple controllers controlling a single sexual stimulation device, a single controller controlling multiple sexual stimulation devices, or multiple controllers controlling multiple sexual stimulation devices.

Figure 36:
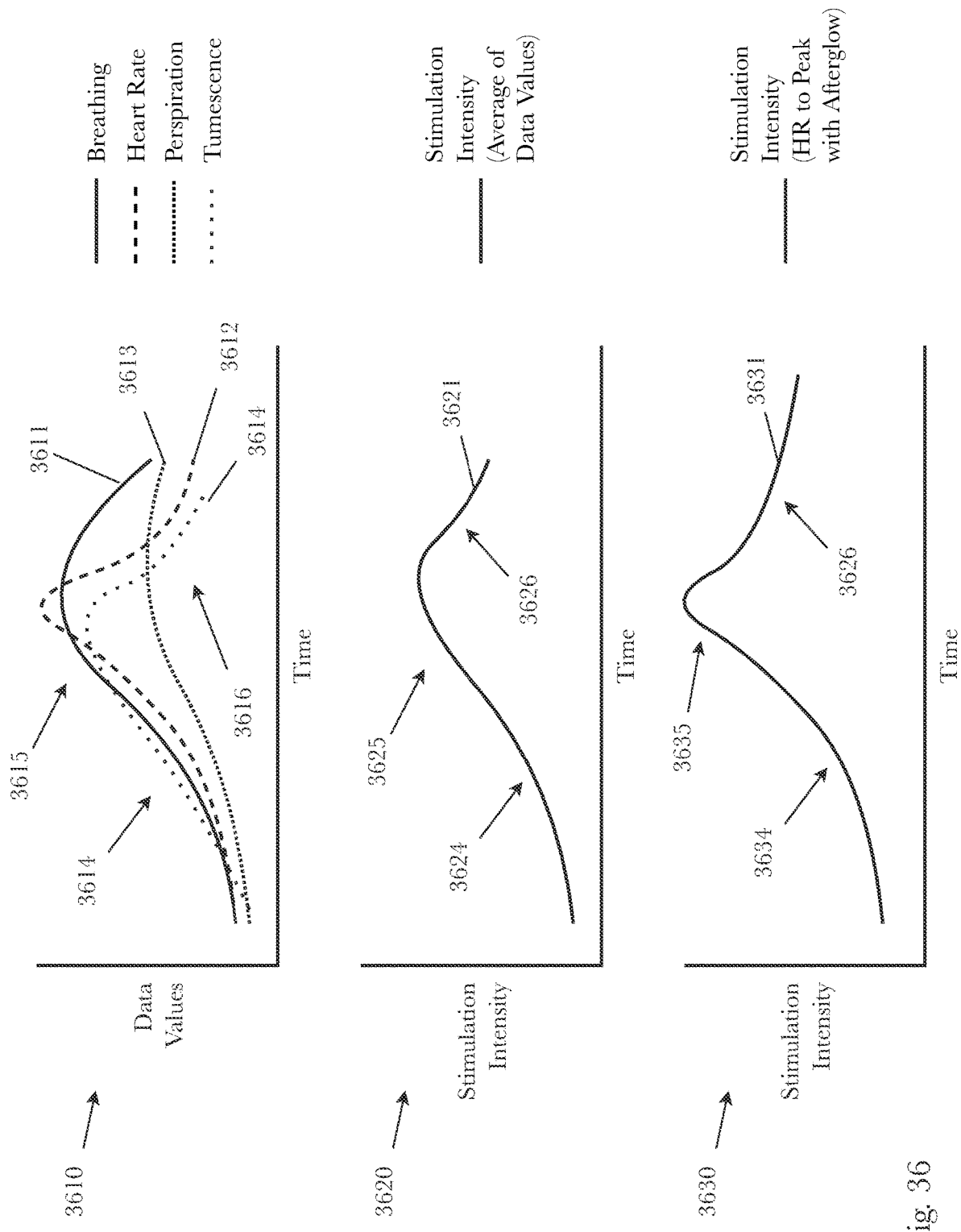
FIG. 36 is an example of the use of biometric data to generate control signals for a biofeedback-based controller for sexual stimulation devices.

FIG. 36 is an example of the use of biometric data to generate control signals for a biofeedback-based controller for sexual stimulation devices. The chart at 3610 shows biometric data values on the y-axis received over time on the x-axis. In this example, four types of biometric data are received, a respiratory (breathing) rate 3611 shown by the solid line, a heart rate 3612 shown by the dashed line, a perspiration level 3613 shown by the close-dotted line, and a penile tumescence level indicated by the sparse-dotted line 3614. Data values for these four biometric indicators are shown as increasing during an excitement and/or plateau phase 3614 of sexual stimulation, peaking at a climax stage (i.e., orgasm) 3615, and decreasing during a resolution phase 3616, in accordance with the standard model of the human sexual response cycle.

The chart at 3620 shows an example of control of sexual stimulation device based on biometric data with stimulation intensity on the y-axis and time on the x-axis. In this case the stimulation intensity shown as a solid line 3621 is an average of the data values for the four types of biometric data shown in 3610. The stimulation intensity is increased during the excitement and/or plateau phase 3624, peaks at a climax stage (i.e., orgasm) 3625, and is decreased during the resolution phase 3626, all corresponding to the average of the exemplary biometric data values of breath rate 3611, heart rate 3612, and perspiration 3613.

The chart at 3630 shows another example of control of sexual stimulation device based on biometric data with stimulation intensity on the y-axis and time on the x-axis. In this case the stimulation intensity shown as a solid line 3636 is an admixture of the data values for the four types of biometric data shown in 3610. The stimulation intensity is increased during the excitement and/or plateau phase 3636 in accordance with the heart rate 3614, peaks at a climax stage (i.e., orgasm) 3635 as a weighted average dominated by the heart rate 3614 and penile tumescence, and is decreased during the resolution phase 3616 as an afterglow (a feeling of sexual satisfaction following orgasm) represented by a heightened average of the exemplary biometric data values of breath rate 3611 and perspiration 3613.

Note that while simple averages are used herein as examples for clarity, control of sexual stimulation devices based on biometric data is not so limited, and many algorithms may be used to determine control signals based on biometric data.

Figure 37:
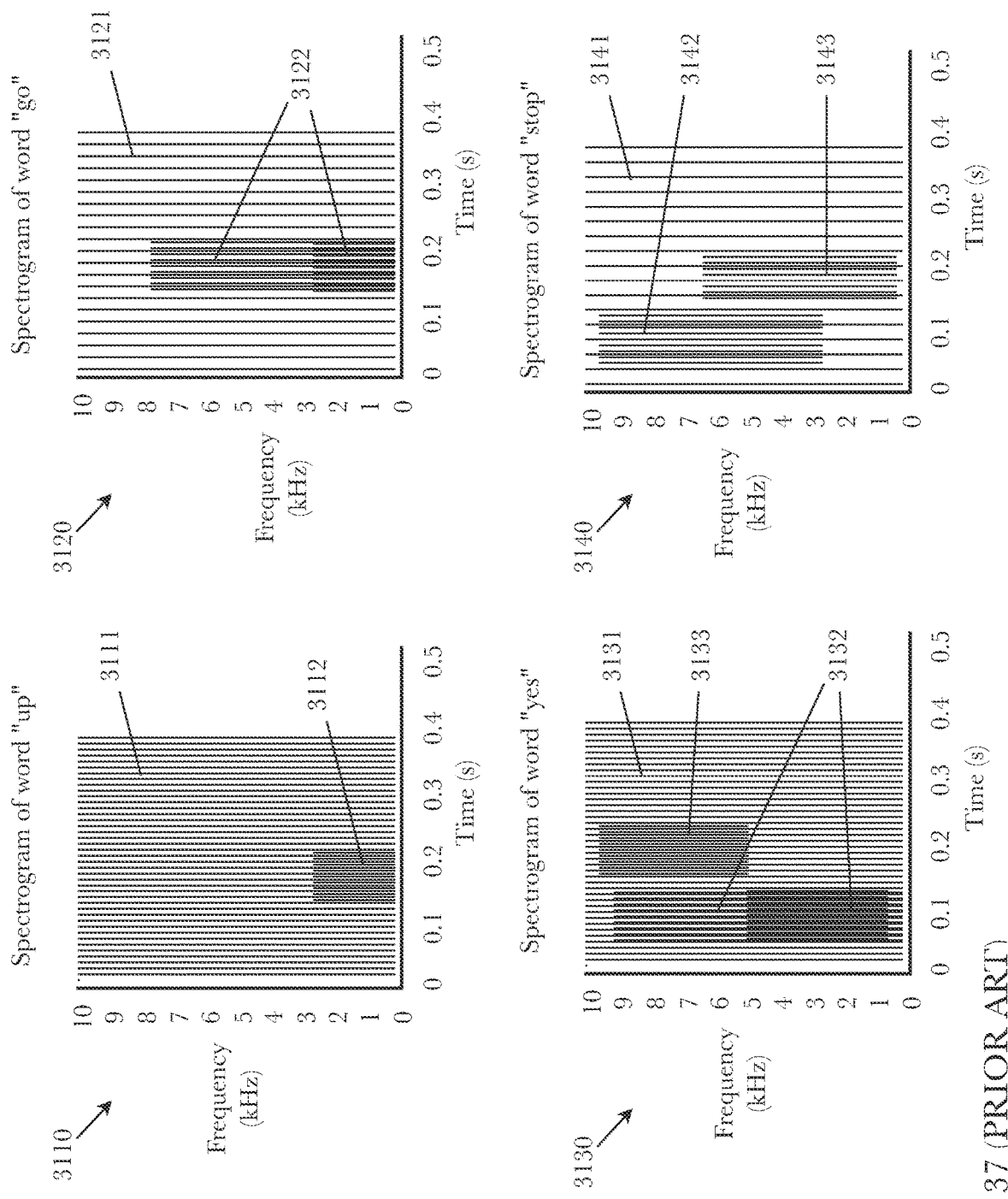
FIG. 37 (PRIOR ART) is a diagram showing exemplary spectrograms of certain words as used in automated speech recognition.

FIG. 37 (PRIOR ART) is a diagram showing exemplary spectrograms of certain words as used in automated speech recognition. Automated speech recognition technology (also called automated speech recognition technology) uses spectrogram analysis to recognize speech within audio. A spectrogram is a visual representation of the spectrum of frequencies of a signal as it varies with time, typically with the y-axis representing frequencies from roughly zero to 10 kHz and the x-axis representing time in fractions of a second. The data underlying the spectrogram is processed through machine learning algorithms trained to recognize patterns representing certain words and phrases. Here, spectrograms for the words "up," "go," "yes," and "stop" are shown.

In the spectrogram of the word "up" 3110, there is a diffuse, largely uniform background pattern across all frequencies 3111 with a moderate signal in the 0 to 2.5 kHz frequencies between 0.1 s and 0.2 s 3112.

In the spectrogram of the word "go" 3120, there is a very diffuse, largely uniform background pattern across all frequencies 3121 with a strong signal in the 0 to 2.5 kHz frequencies and a moderate signal in the 2.5 kHz to 8 kHz frequencies between 0.1 s and 0.2 s 3122.

In the spectrogram of the word "yes" 3130, there is a diffuse, largely uniform background pattern across all frequencies 3131 with a strong signal in the 0 to 5 kHz frequencies and a moderate signal in the 5 kHz to 9 kHz frequencies between 0.05 s and 0.15 s 3132, and a moderate signal in the 5 kHz to 9.5 kHz frequencies between 0.15 s and 0.25 s 3133.

In the spectrogram of the word "stop" 3140, there is a very diffuse, largely uniform background pattern across all frequencies 3141 with a moderate signal in the 3 kHz to 9 kHz frequencies between 0.05 s and 0.15 s 3142, and a moderate signal in the 0.5 kHz to 6.5 kHz frequencies between 0.15 s and 0.25 s 3143.

These patterns are recognizable by humans, but it can be hard to distinguish between similar patterns reliably, and recognition is slow. Trained machine learning algorithms are applied to automatically make fine distinctions between similar patterns on a near-real-time basis in audio files and streaming audio.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 38:
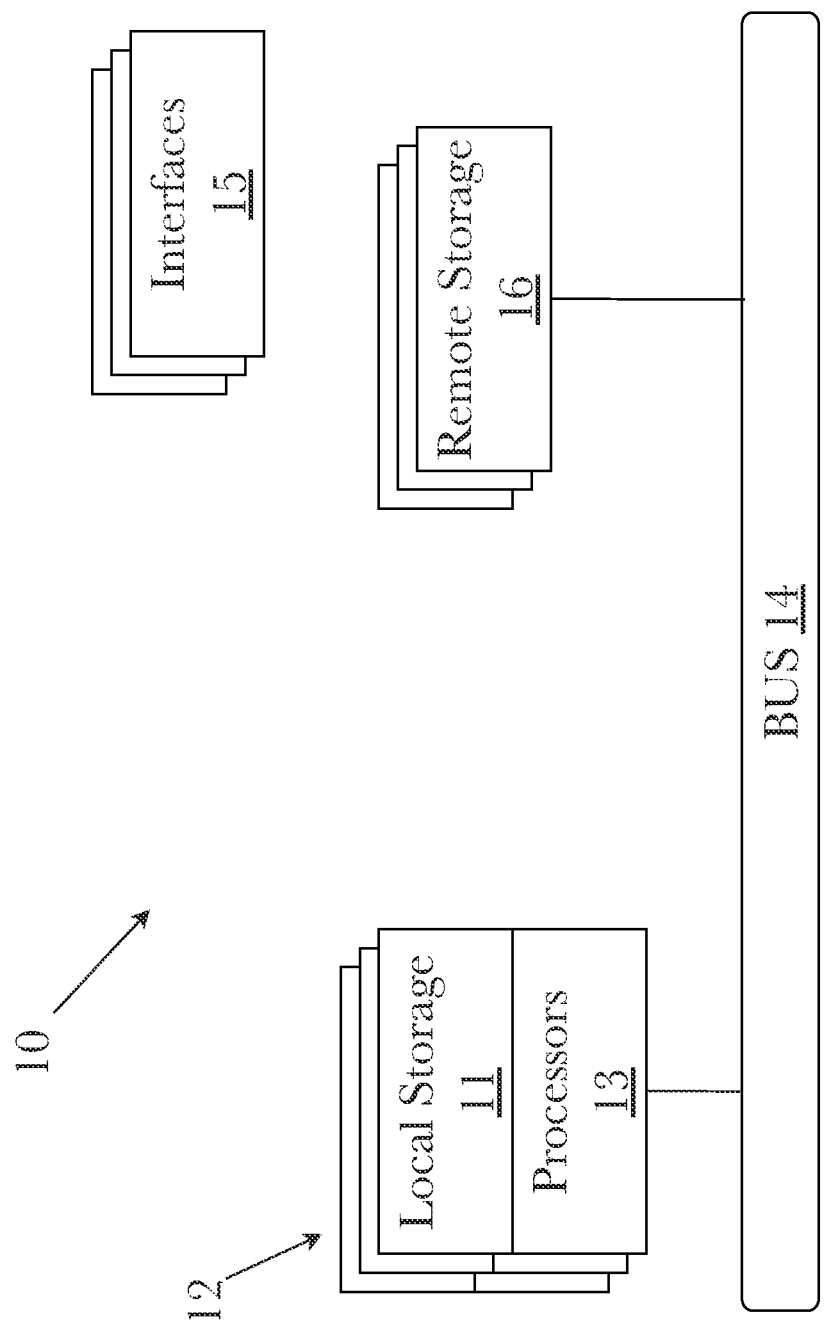
FIG. 38 is a block diagram illustrating an exemplary hardware architecture of a computing device.

Referring now to FIG. 38, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 38 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 39:
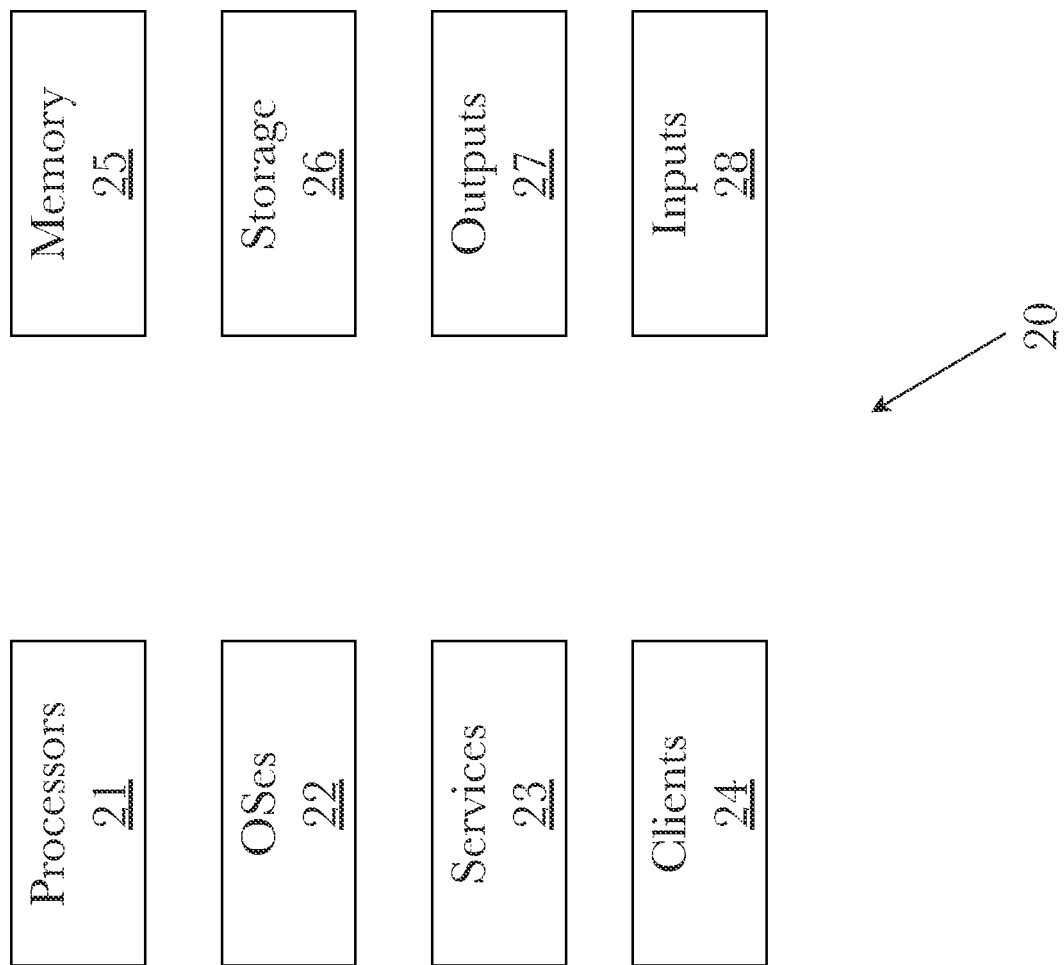
FIG. 39 is a block diagram illustrating an exemplary logical architecture for a client device.

In some aspects, systems may be implemented on a standalone computing system. Referring now to FIG. 39, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 38). Examples of storage devices 26 include flash memory, magnetic hard drive, CD-ROM, and/or the like.

Figure 40:
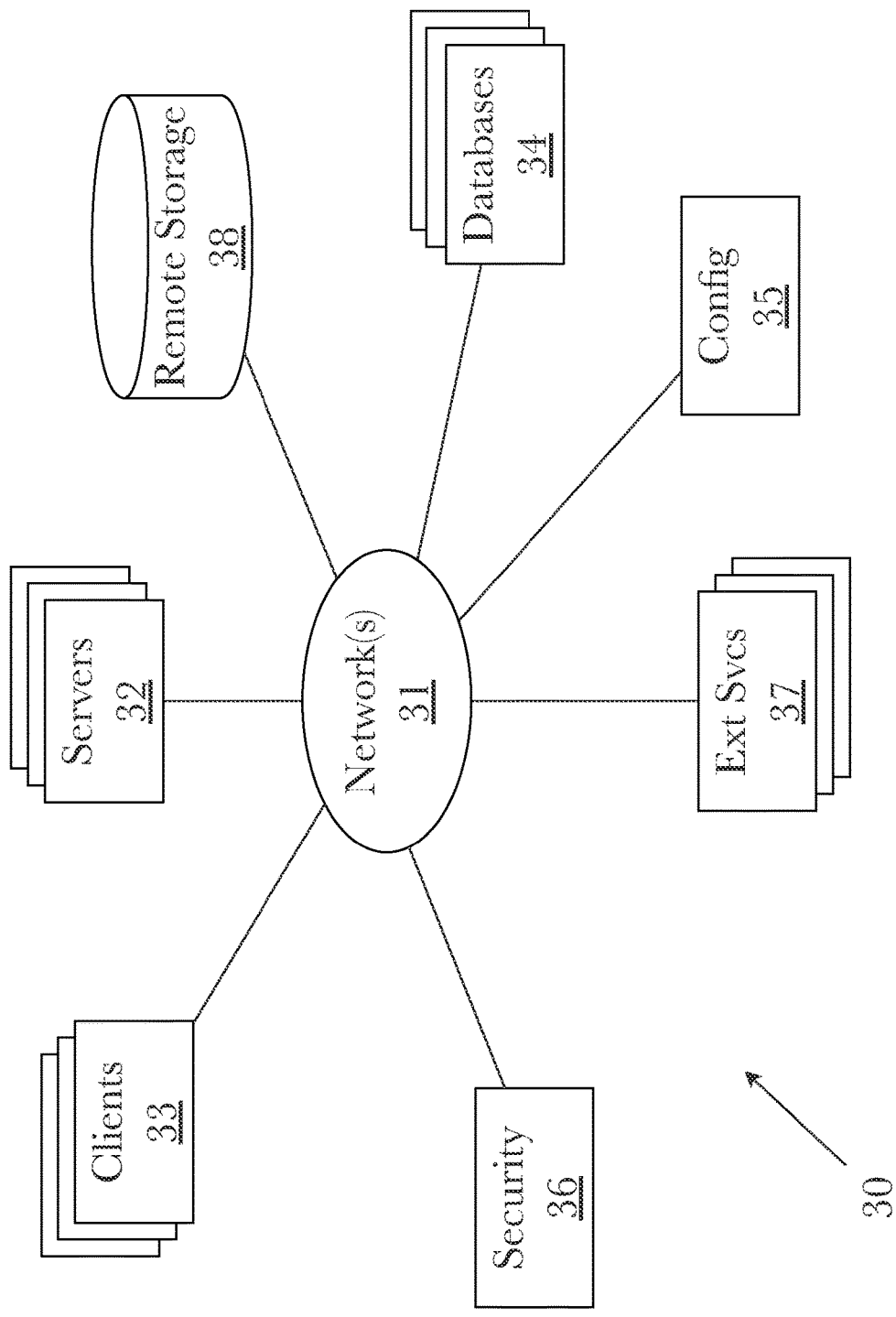
FIG. 40 is a block diagram showing an exemplary architectural arrangement of clients, servers, and external services.

In some aspects, systems may be implemented on a distributed computing network, such as one having any number of clients and/or servers. Referring now to FIG. 40, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 39. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 39 when needed to obtain additional information, or to refer to additional data concerning a particular call. Communications with external services 39 may take place, for example, via one or more networks 31. In various aspects, external services 39 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 39 deployed on one or more of a particular enterprise's or user's premises. In addition to local storage on servers 32, remote storage 40 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 40 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 38 and configuration systems 37. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 38 or configuration system 37 or approach is specifically required by the description of any specific aspect.

Figure 41:
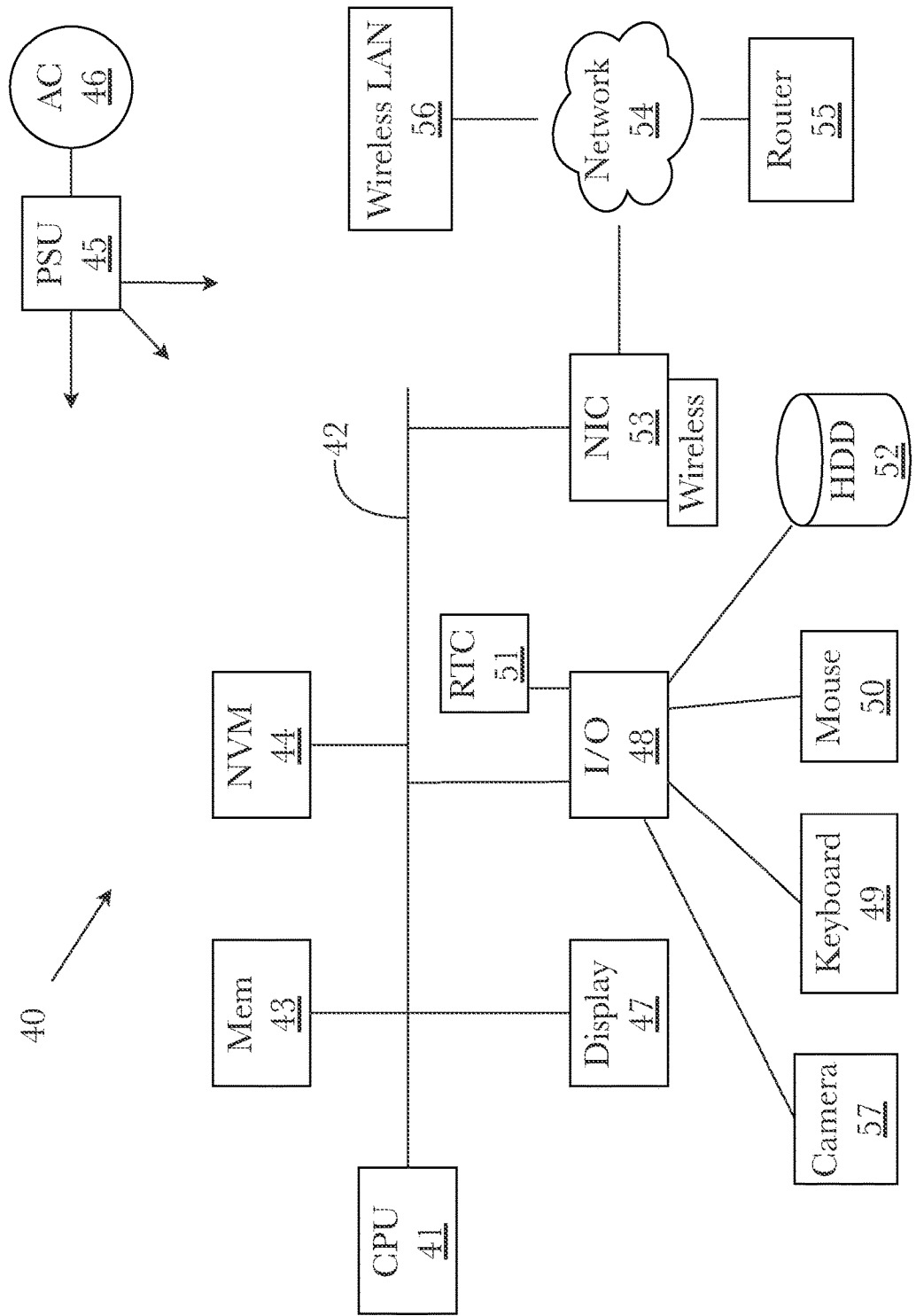
FIG. 41 is another block diagram illustrating an exemplary hardware architecture of a computing device.

FIG. 41 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. An adaptive speech system for sexual stimulation devices, comprising:
a computing device comprising a memory and a processor;
a microphone connected to the computing device and configured to receive audio and transmit the audio to the computing device;
a speech detector comprising a first plurality of programming instructions stored in the memory which, when operating on the processor, causes the computing device to:
receive the audio via the microphone;
perform automated speech recognition to detect speech in the audio;
match the detected speech to one or more commands for a sexual stimulation device; and
send the one or more commands to a control signal generator;
a voice data manager comprising a second plurality of programming instructions stored in the memory which, when operating on the processor, causes the computing device to determine an association between the speech and a stimulation objective based on a plurality of speech/objective pairs; and
the control signal generator comprising a third plurality of programming instructions stored in the memory which, when operating on the processor, causes the computing device to:
receive the one or more commands from the speech detector;
generate a control signal for the sexual stimulation device corresponding to the one or more commands;
receive the association and adjust the control signal based on the association; and
output the adjusted control signal for use in operating the sexual stimulation device.

2. The system of claim 1, wherein the computing device is incorporated into the sexual stimulation device.

3. The system of claim 2, wherein the microphone is incorporated into the sexual stimulation device.

4. The system of claim 1, further comprising a biometric sensor connected to the computing device and configured to receive biometric data and transmit the biometric data to the computing device; wherein
the voice data manager is further configured to receive the biometric data from the biometric sensor and further adjust the control signal based on the biometric data prior to outputting the adjusted control signal for use in operating the sexual stimulation device.

5. The system of claim 4, wherein the biometric sensor is an external heart rate monitoring device connected to the computing device.

6. The system of claim 4, wherein the computing device is a mobile phone connected wirelessly to the sexual stimulation device and wherein the biometric sensor is incorporated into the mobile phone.

7. The system of claim 4, wherein the computing device is a mobile phone connected wirelessly to the sexual stimulation device and wherein the biometric sensor is an external heart rate monitoring device connected to the mobile phone.

8. The system of claim 4, further comprising a machine learning algorithm operating on the computing device which is configured to automatically determine the adjustment to the control signal using the one or more commands and the biometric data as inputs.

9. The system of claim 1, wherein the computing device is a mobile phone connected wirelessly to the sexual stimulation device.

10. The system of claim 9, wherein the microphone is incorporated into the mobile phone.

11. A method for adaptive speech of sexual stimulation devices, comprising the steps of:
using speech detector software operating on a computing device comprising a memory and a processor to:
receive audio via a microphone connected to the computing device and configured to receive the audio and transmit the audio to the computing device;
perform automated speech recognition to detect speech in the audio;
match the detected speech to one or more commands for a sexual stimulation device; and send the one or more commands to a control signal generator application operating on the computing device;

using a voice data manager application operating on the computing device to determine an association between the speech and a stimulation objective based on a plurality of speech/objective pairs; and using the control signal generator application operating on the computing device to:

receive the one or more commands from the speech detector software;

generate a control signal for the sexual stimulation device corresponding to the one or more commands;

receive the association and adjust the control signal based on the association; and output the adjusted control signal for use in operating the sexual stimulation device.

12. The method of claim 11, wherein the computing device is incorporated into the sexual stimulation device.

13. The method of claim 12, wherein the microphone is incorporated into the sexual stimulation device.

14. The method of claim 11, wherein:

a biometric sensor connected to the computing device and configured to receive biometric data and transmit the biometric data to the computing device; and the voice data manager is further configured to receive the biometric data from the biometric sensor and further adjust the control signal based on the biometric data prior to outputting the adjusted control signal for use in operating the sexual stimulation device.

15. The method of claim 14, wherein the biometric sensor is an external heart rate monitoring device connected to the computing device.

16. The method of claim 14, wherein the computing device is a mobile phone connected wirelessly to the sexual stimulation device and wherein the biometric sensor is incorporated into the mobile phone.

17. The method of claim 14, wherein the computing device is a mobile phone connected wirelessly to the sexual stimulation device and wherein the biometric sensor is an external heart rate monitoring device connected to the mobile phone.

18. The method of claim 14, further comprising the step of using a machine learning algorithm operating on the computing device to automatically determine the adjustment to the control signal using the one or more commands and the biometric data as inputs.

19. The method of claim 11, wherein the computing device is a mobile phone connected wirelessly to the sexual stimulation device.

20. The method of claim 19, wherein the microphone is incorporated into the mobile phone.

* * * * *